(12) United States Patent
Tsujimoto

(10) Patent No.: US 7,125,114 B2
(45) Date of Patent: Oct. 24, 2006

(54) RECORDING MEDIUM DISCRIMINATING METHOD AND RECORDING APPARATUS

(75) Inventor: Takuya Tsujimoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/111,955

(22) Filed: Apr. 22, 2005

(65) Prior Publication Data

US 2005/0185553 A1    Aug. 25, 2005

Related U.S. Application Data

(62) Division of application No. 10/610,872, filed on Jul. 2, 2003, now Pat. No. 6,984,034.

(30) Foreign Application Priority Data

Jul. 10, 2002    (JP) .............................. 2002-201469

(51) Int. Cl.
*B41J 2/01*    (2006.01)
(52) U.S. Cl. ..................... 347/105; 347/14; 347/101; 358/1.1; 358/1.6
(58) Field of Classification Search ................ 347/5, 347/16, 19, 101, 105, 14; 358/1.1, 1.6; 428/195, 428/32.1
See application file for complete search history.

(56) References Cited

U.S. PATENT DOCUMENTS

| 5,109,236 | A |   | 4/1992 | Watanabe et al. | |
| 5,925,889 | A | * | 7/1999 | Guillory et al. | 356/446 |
| 6,520,614 | B1 |  | 2/2003 | Kaneko | 347/14 |
| 2002/0186385 | A1 |  | 12/2002 | Richards | 358/1.6 |
| 2003/0137679 | A1 | * | 7/2003 | Nakazawa et al. | 358/1.6 |
| 2003/0202214 | A1 |  | 10/2003 | Akita et al. | 382/108 |
| 2004/0008869 | A1 |  | 1/2004 | Tsujimoto | |

FOREIGN PATENT DOCUMENTS

| EP | 0 911 699 | 4/1999 |
| JP | 2-138805 | 5/1990 |
| JP | 9-40227 | 2/1997 |
| JP | 11-101744 | 4/1999 |
| JP | 11-271037 | 10/1999 |
| JP | 2001-260425 | 9/2001 |
| JP | 2001-337496 | 12/2001 |
| JP | 2002-27242 | 1/2002 |
| JP | 2003-212390 | 7/2003 |

* cited by examiner

*Primary Examiner*—Manish S. Shah
(74) *Attorney, Agent, or Firm*—Fitzpatrick, Cella, Harper & Scinto

(57) ABSTRACT

Discrimination of the type of a recording medium with high accuracy is obtained by using the intensity of a specular reflection light from the recording medium and a feature of the recording medium surface derived from an image of the recording medium surface as discrimination parameters. In particular, the accuracy in discrimination between plain paper and ink-jet coated paper and between photographic glossy paper and a glossy film is improved. Also, the type of the recording medium is discriminated based on a detected value of the intensity of the specular reflection light from the recording medium and a parameter representing surface conditions of the recording medium which is derived from an image information made up of a plurality of pixels corresponding to a predetermined area of the recording medium surface.

4 Claims, 38 Drawing Sheets

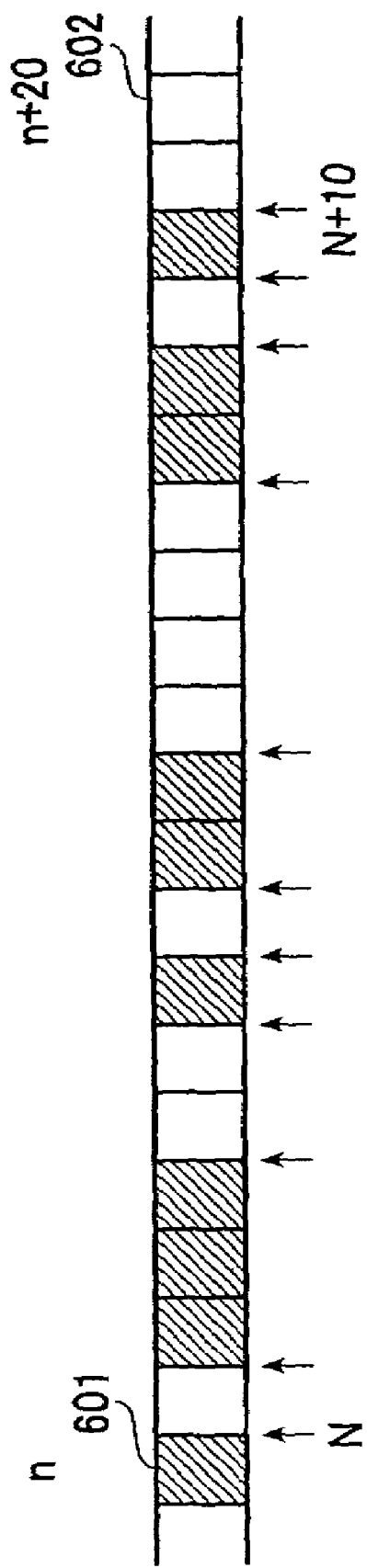

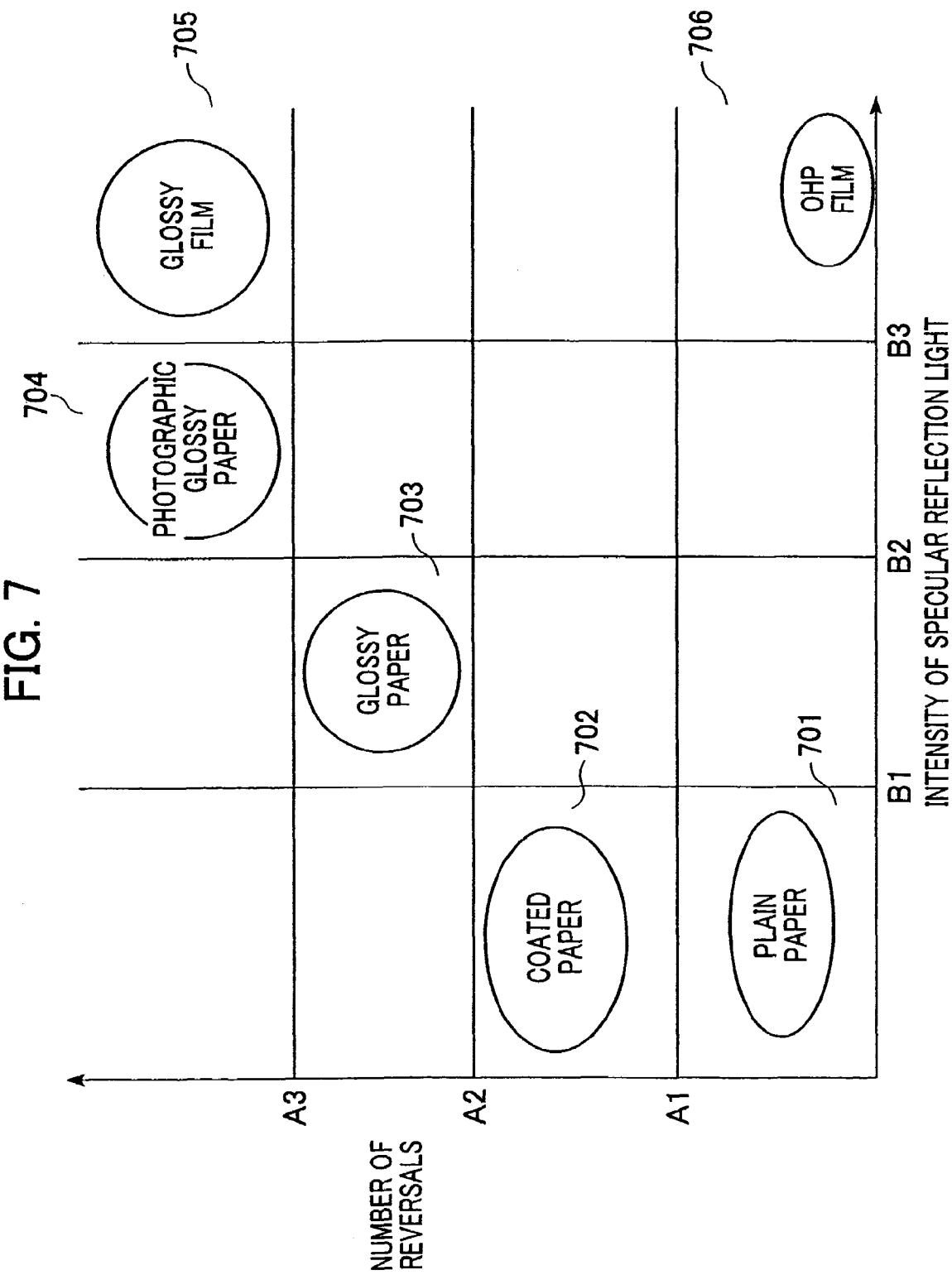

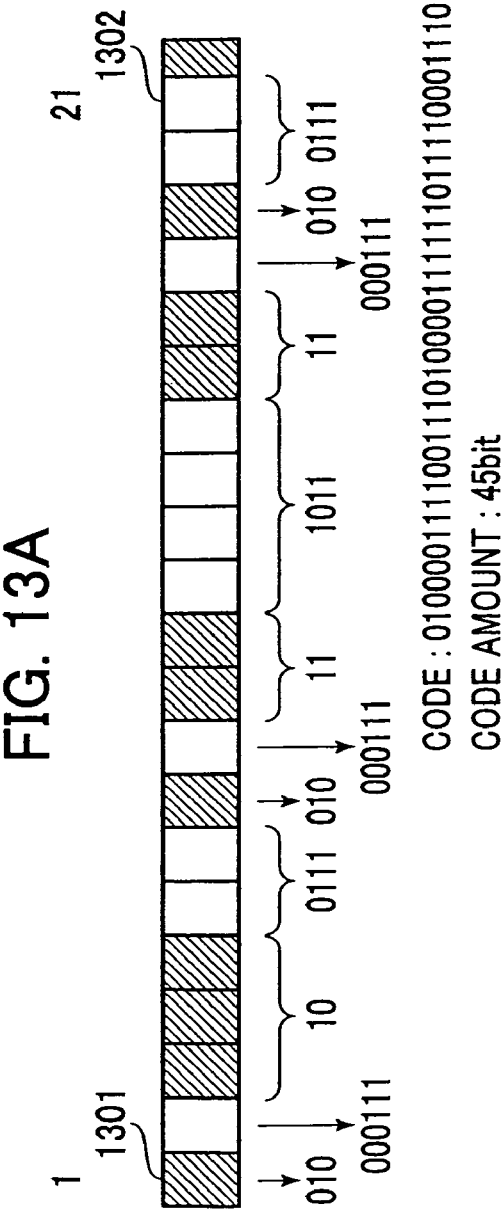

RECORDING MEDIUM DISCRIMINATING METHOD AND RECORDING APPARATUS

This application is a division of application Ser. No. 10/610,872 filed Jul. 2, 2003 now U.S. Pat. No. 6,984,034.

BACKGROUND OF THE INVENTION

1. Field of the Invention

The present invention relates to a recording medium discriminating method for discriminating the type of a recording medium, a recording apparatus having a function of discriminating the type of a recording medium, a program for executing the discrimination as to the type of a recording medium, and a storage medium storing the program. More particularly, the present invention relates to a technique for discriminating the type of a recording medium from image information regarding a surface of the recording medium.

2. Description of the Related Art

Hitherto, various types of output devices, such as electrophotographic, wired-dot, and ink-jet devices, have been practiced as output devices of printing systems in which a color image is formed by attaching colored toners or inks to a recording surface of a recording medium and then ejecting the recording medium having the color image recorded thereon.

Of those output devices, the ink-jet device has garnered a lot of attention because such a device directly ejects inks from a recording head to the recording medium. This device, thus, requires fewer number of steps to form an image on the recording medium than other devices, and has additional advantages such as a low running cost, being suitable for color recording, and it produces less noise during the recording operation. For these reasons, the ink-jet device has received attention in a variety of markets ranging from business to domestic fields. Recently, many recording apparatuses (printers), facsimile machines, and copying machines have been practiced using output devices of the ink-jet type.

It is generally known that various types of recording media are employed in an ink-jet recording apparatus. The types of recording media include plain paper, typically used regardless of the recording scheme, ink-jet coated paper (including a postcard dedicated for ink-jet printing, such as a New Year's card having the postcard size) in which a coating agent, e.g., silica, is applied to the recording surface of the recording medium for suppressing ink blurring and improving color development. Other recording media include: glossy paper and glossy film, which have a glossy appearance on the recording surface of the recording medium similar to photographic paper for glossy print, and which are used for forming photographs and images; an OHP film for a transparent document; transfer paper for transferring an image to a cloth, e.g., using an iron to transfer the image to a T-shirt, after recording the image on the recording medium; and a back print film in which a back surface of the recording medium serves as a recording surface. Thus, there are various types of recording media including others that are familiar to users.

In the ink-jet recording apparatus, because permeability and fixity of ink differ depending on the coating agent applied to the surface of the recording medium, recording conditions for obtaining a good recorded image differ depending on the type of the recording medium. As a result, before the recording process begins, the user must select or enter the type of recording medium on which the image is to be recorded into the system and must set a recording mode suitable for the recording medium. In so doing, if the user erroneously sets the type of the recording medium and the recording mode by mistake, a recording image having the quality demanded by the user cannot be obtained in some cases. To avoid the troublesome operation required by the user and the possibility of a false setting, a device for automatically discriminating the type of the recording medium and then selecting and setting an optimum recording mode has been created. This automatic setting of a suitable recording mode for the type of the recording medium is needed in not only the ink-jet recording apparatus, but also in other types of recording apparatuses.

FIG. 35 shows one example of a method for discriminating the type of the recording medium. With this method, a light is illuminated from a light source to a recording medium, and a reflected light from a surface of the recording medium is detected by an optical sensor using a photoelectric transducer to measure the intensity of the reflected light. Referring to FIG. 35, a light source 3501 illuminates a light at an angle θ of incidence (arbitrary value) to a recording medium 3504 of which type is to be determined. A light receiving device 3502 for measuring the intensity of a specular reflection light receives a light that has been reflected at an angle θ of reflection equal to the angle θ of incidence at which the light was illuminated from the light source 3501. Because the intensity of the specular reflection light changes depending on a gloss of the recording medium surface, the gloss of the recording medium can be confirmed by measuring the intensity of the specular reflection light. Further, a light receiving device 3503 receives a light having diffusely reflected at an angle different from the angle θ of incidence, at which the light was illuminated from the light source 3501, (e.g., a light having reflected at a right angle relative to the recording medium in FIG. 35), for measuring the intensity of a diffuse reflection light. Because the intensity of the diffuse reflection light changes depending on the whiteness of the recording medium surface, the whiteness of the recording medium can be confirmed by measuring the intensity of the diffuse reflection light. The light source 3501 and the light receiving device 3502 receiving the specular reflection light are set in a layout such that the specular reflection light having reflected from the recording surface of the recording medium 3504 subjected to illumination from the light source 3501 can be received by the light receiving device 3502. Likewise, the light source 3501 and the light receiving device 3503 receiving the diffuse reflection light are set in a layout such that the diffuse reflection light having reflected from the recording surface of the recording medium 3504 subjected to illumination from the light source 3501 can be received by the light receiving device 3503. By comparing values of the intensity of two reflected lights thus obtained with corresponding values of the intensity of two reflected lights measured in advance for each type of the recording medium to be used, the type of the recording medium is discriminated.

Japanese Patent Laid-open No. 11-271037 discloses an image forming method and an image forming apparatus for forming a high-quality image without regard to the type of the recording medium used and surface roughness thereof. In the disclosed method and apparatus, surface roughness is detected by measuring, as three-dimensional image information, an intensity distribution of a reflected light from a recording medium obtained when a light from a light source is illuminated to the recording medium, and then converting the detected information into a fractal dimension, i.e., one-dimensional information. A toner amount is then controlled to be matched with the surface roughness of the recording medium.

Also, the assignee of the present application has previously proposed a discriminating device and a discriminating method in which, with a system employing a plurality of light receiving devices, the type of the recording medium is discriminated based on a gloss of the recording medium surface and fiber orientation of the recording medium surface. With this method, the fiber orientation of the recording medium surface is detected from a variation in intensity of diffuse reflection light sensed by the plurality of light receiving devices.

The related art described above, however, has problems as follows.

FIG. 36 shows the relationships of various types of recording media versus the intensity of the specular reflection light and the intensity of the diffuse reflection light. In FIG. 36, numeral 3601 represents a distribution region of plain paper in terms of the intensity of the specular reflection light and the intensity of the diffuse reflection light. Likewise, numerals 3602, 3603, 3604, 3605 and 3606 represent distribution regions of ink-jet coated paper, glossy paper, photographic glossy paper, a glossy film, and an OHP film, respectively. As seen from FIG. 36, it is difficult to accurately discriminate plain paper and ink-jet coated paper from the relationships between the recording media and two reflected-light components, i.e., the specular reflection light and the diffuse reflection light.

The intensity of the specular reflection light representing the gloss of the recording medium is given a value corresponding to the surface roughness so long as the recording medium is formed of the same material (although the intensity of the specular reflection light is indirectly affected by not only a surface layer, but also an intermediate layer). Accordingly, the intensity of the specular reflection light can be used as a parameter for discriminating the type of the recording medium. However, because various types of recording media are formed of a variety of different materials, there is a possibility that different types of recording media in fact provide values of the intensity of the specular reflection light comparable to each other. Such a case is confirmed, by way of example, with plain paper and ink-jet coated paper. Ink-jet coated paper has a higher smoothness (which is increased as the recording medium has a flatter and smoother surface) than plain paper, and therefore it provides a greater intensity of the specular reflection light if the recording medium is formed of the same material. However, light diffusion by the ink-jet coated paper is increased with the presence of a pigment, e.g., silica, applied to its surface. As a result, the value of the intensity of the specular reflection light from the ink-jet coated paper is comparable to or slightly smaller than that of the plain paper.

Further, many types of plain paper and ink-jet coated paper provide close values of the intensity of the diffuse reflection light that represents whiteness of the recording medium. The reason is that users prefer recording media having a high degree of whiteness, which make black characters appear more tightly and provide a better color tint of a photographic image. In the past, placing a coat of calcium carbonate on the recording medium surface has been avoided for the problem that calcium carbonate scrapes a fusing roller used in an image forming apparatus employing the electrophotographic technique, such as a copying machine. Recently, however, calcium carbonate has been widely coated because of increased durability of the fusing roller. The coating of calcium carbonate is effective in increasing the whiteness of the recording medium, but it becomes difficult to discriminate plain paper having high whiteness because of a coating of calcium carbonate from ink-jet coated paper.

Thus, in a conventional system employing reflection optical sensors for measuring the intensity of the specular reflection light and the intensity of the diffuse reflection light, it is difficult to discriminate plain paper and ink-jet coated paper from each other. This leads to a serious problem in an ink-jet recording apparatus in which recording conditions, such as the amount of ejected ink and the number of scans, i.e., passes, of a recording head for recording a one-line image differ depending on the type of the recording medium. In the above-mentioned two types of recording media, particularly, a significant difference exists in the recording conditions and hence a serious image quality problem results as well.

Also, in electrophotographic recording apparatuses other than the ink-jet recording apparatus, if users mistakenly place ink-jet coated paper instead of plain paper in a cassette storing the recording medium, there is a risk that the recording medium will wrap around the fusing roller and cause a paper jam. In other words, the necessity of accurately discriminating various types of recording media for ink-jet printing, which are widely put into the market, is a problem not restricted to the field of ink-jet recording apparatuses.

To solve the above-mentioned problem, the inventors have studied as a method of discriminating plain paper and ink-jet coated paper from each other with high accuracy, a method wherein the features of the surface roughness and the surface shape of a recording medium are obtained from image information regarding a surface of the recording medium by using an image sensor, as shown in FIG. 37, and then discriminating the type of the recording medium. Here, the surface roughness implies a feature regarding the magnitude of unevenness of the recording medium surface, and the surface shape implies a feature regarding the period of unevenness of the recording medium surface.

FIG. 37 is a schematic view showing a sensor system for discriminating the type of the recording medium by using the image sensor.

Referring to FIG. 37, a light source 3701 illuminates a light at an angle θ of incidence (arbitrary value) to a recording medium 3703 of which type is to be discriminated. Also, an image sensor 3702 creates image information regarding a surface of the recording medium from a component of diffuse reflection light having reflected at an angle different from the angle θ of incidence at which the light was illuminated from the light source 3701 (in FIG. 37, a light having reflected at a right angle relative to the recording medium). The light source 3701 and the image sensor 3702 are set in a layout such that the diffuse reflection light having reflected from the recording surface of the recording medium 3703 subjected to illumination from the light source 3701 can be received by the image sensor 3702.

By comparing parameters representing surface conditions of the recording medium obtained from the image information resulting from the above-described sensor system with corresponding parameters measured in advance and representing surface conditions of the recording medium of the type which is to be used, the type of the recording medium is discriminated. FIG. 38 shows the relationships of various types of recording media versus a brightness difference and an average value of brightness. Those relationships are obtained when employing, as two examples of the parameters representing surface conditions of the recording medium, the brightness difference, i.e., the difference between maximum and minimum values of brightness in image information comprising a plurality of pixels, and the average value of the brightness. Numeral 3801 represents a distribution region of plain paper. Likewise, numerals 3802, 3803, 3804, 3805 and 3806 represent distribution regions of ink-jet coated paper, glossy paper, photographic glossy paper, a glossy film, and an OHP film, respectively. As seen from FIG. 38, it is possible to discriminate plain paper and ink-jet coated paper based on the plotted relationship.

With the above-described system using the image sensor, plain paper and ink-jet coated paper, which have been usually employed for recording in the past, can be discriminated from each other. However, it is difficult to discriminate several types of recording media used in high quality image recording.

More specifically, while attention has been recently focused on photographic glossy paper, which is a recording medium capable of recording an image with a quality comparable to that of a photograph printed on photographic paper, and on a glossy film using white PET, etc. as a base, it is difficult to accurately discriminate those two types of recording media because both recording media have high gloss values. The reason is that, as a result of various improvements in recording an image with a quality comparable to that of a photograph printed on photographic paper, photographic glossy paper has a higher smoothness than conventional glossy paper, thus the glossy film and the photographic glossy paper have similar physical properties, such as surface roughness and surface shape.

SUMMARY OF THE INVENTION

With the view of overcoming the above-mentioned problems in the related art, the present invention is intended to discriminate the type of a recording medium with high accuracy. Particularly, it is an object of the present invention to provide a recording medium discriminating method capable of discriminating plain paper, ink-jet coated paper, and a recording medium having a high gloss, i.e., a glossy film or photographic glossy paper, with high accuracy. Other objectives of the present invention include providing a recording apparatus having a function of discriminating the type of a recording medium, a program for executing the discrimination as to the type of a recording medium, and a storage medium storing the program.

The present invention provides a recording medium type discriminating method for discriminating the type of a recording medium comprising a step of creating image information indicating surface conditions of the recording medium, wherein the image information contains information for each of a plurality of pixels corresponding to a predetermined area of a recording medium surface; a step of detecting a gloss level of the recording medium surface; a step of obtaining, from the image information, a parameter regarding the surface conditions of the recording medium; and a step of discriminating the type of the recording medium based on the gloss level and the parameter regarding the surface conditions of the recording medium.

Also, the present invention provides a recording medium type discriminating method for discriminating the type of a recording medium comprising: a step of creating image information indicating surface conditions of the recording medium, wherein the image information contains information for each of a plurality of pixels corresponding to a predetermined area of a recording medium surface and brightness information for each of the plurality of pixels; a step of detecting a gloss level of the recording medium surface; and a step of discriminating the type of the recording medium based on the gloss level and a parameter obtained from the brightness information.

Further, the present invention provides a program for causing a computer to execute a process for discriminating the type of a recording medium, the program comprising program codes for executing a step of creating image information indicating surface conditions of the recording medium, wherein the image information contains information for each of a plurality of pixels corresponding to a predetermined area of a recording medium surface and brightness information for each of the plurality of pixels; a step of detecting a gloss level of the recording medium surface; and a step of discriminating the type of the recording medium based on the gloss level and a parameter obtained from the brightness information.

Still further, the present invention provides a computer-readable storage medium storing a program to discriminate the type of a recording medium, the storage medium storing an image information creating module for creating image information indicating surface conditions of the recording medium, wherein the image information contains information for each of a plurality of pixels corresponding to a predetermined area of a recording medium surface and brightness information for each of the plurality of pixels; a detecting module for detecting a gloss level of the recording medium surface; and a discriminating module of discriminating the type of the recording medium based on the gloss level and a parameter obtained from the brightness information.

In addition, the present invention provides a recording apparatus for recording an image on a recording medium, which is fed by a feed unit in accordance with recording data, wherein the apparatus comprises: an image information creating unit for creating image information indicating surface conditions of the recording medium fed by the feed unit, wherein the image information contains information for each of a plurality of pixels corresponding to a predetermined area of a recording medium surface and brightness information for each of the plurality of pixels; a detecting unit for detecting a gloss level of the recording medium surface; and a discriminating unit for discriminating the type of the recording medium based on the gloss level and a parameter obtained from the brightness information.

According to the present invention having the features set forth above, the following advantages are obtained.

The parameters required for discriminating the type of the recording medium are obtained from both the intensity of the specular reflection light from the recording medium to be detected and the image information of the arbitrary small area of the recording medium surface. The type of the recording medium is discriminated based on these obtained parameters. Therefore, the type of the recording medium can be discriminated with higher accuracy than is possible with the conventional methods of discriminating the type of the recording medium by using a reflection optical sensor or an image sensor. In particular, the accuracy in discriminating between plain paper and ink-jet coated paper and between photographic glossy paper and a glossy film can be improved. Accordingly, it becomes possible to discriminate most types of recording media selectable by a printer driver, and hence it is possible to provide an environment capable of properly selecting and setting various recording conditions without requiring users to perform troublesome operations.

Also, by employing an image sensor, an image of the recording medium surface can be produced through a measurement made on only one point, and therefore the need of moving the recording medium or the image sensor is no longer essential. As a matter of course then, there is no longer a need for a mechanical mechanism for moving the recording medium or the image sensor.

In addition, the accuracy in discriminating between photographic glossy paper and a glossy film can be improved by employing the intensity of the specular reflection light.

Further objects, features and advantages of the present invention will become apparent from the following description of the preferred embodiments with reference to the attached drawings.

BRIEF DESCRIPTION OF THE DRAWINGS

FIG. 6 is a representation for explaining the number of times each pixel value is reversed between 0 and 1 after the binary coding in the first embodiment.

FIG. 7 is a discrimination map showing the relationships of various types of recording media versus the number of reversals (of pixel values) and the intensity of a specular reflection light in the first embodiment.

FIGS. 13A and 13B are representations for explaining run-length encoding and a code amount in the second embodiment.

DESCRIPTION OF THE PREFERRED EMBODIMENTS (First Embodiment)

A first embodiment implementing the present invention will be described below in detail with reference to the drawings. Each of the elements shown in block outline in the figures is well known per se, and a specific type of construction is not critical to carrying out the invention or to a disclosure of the best mode for carrying the invention.

Figure 1:
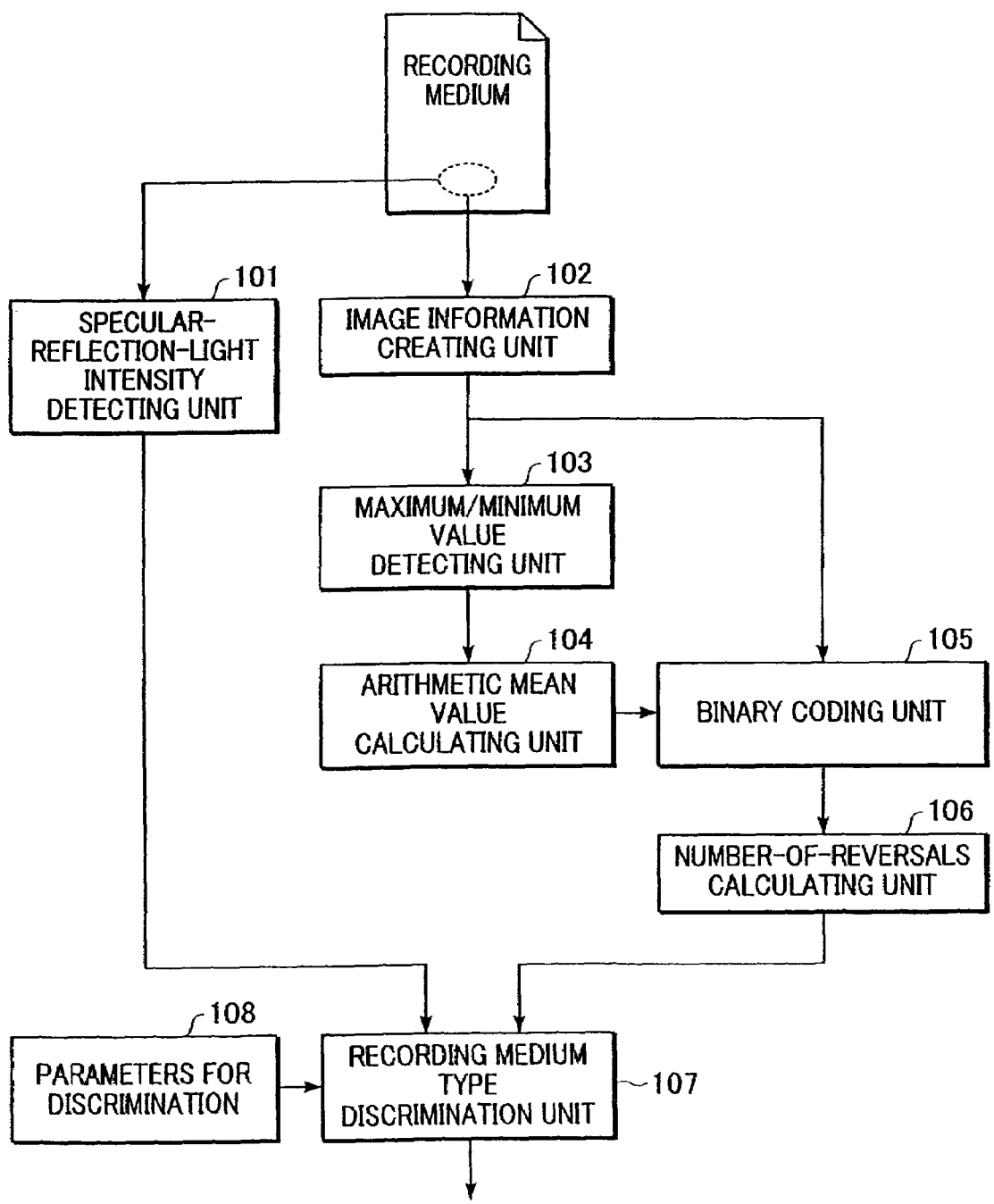
FIG. 1 is a functional block diagram showing a recording medium discriminating method according to a first embodiment of the present invention.

FIG. 1 is a functional block diagram showing a recording medium discriminating method according to a first Referring to FIG. 1, a specular-reflection-light intensity detecting unit 101 detects the intensity of one component of reflected light from a surface of a recording medium, which is illuminated by a light source, i.e., the intensity of a specular reflection light having reflected at an angle of reflection equal to an angle of incidence is detected. embodiment of the present invention.

An image information creating unit 102 creates image information from an arbitrary small area of the recording medium surface. An image created by the image information creating unit 102 is made up of a plurality of pixels each having a brightness value larger than a one-bit value. It is here assumed that the image is a set of pixels having 8-bit brightness information. In this context, each pixel may have or may not have color information of RGB. The image of the arbitrary small area may be a one- or two-dimensional image. Also, a new image may be re-formed so that only a particular area of an originally obtained image is used for discrimination of the recording medium. In this embodiment, it is assumed that image information is created from a component of diffuse reflection light, and each of the pixels constituting an image has no color information, but has only brightness information. One example of a layout of an optical sensor used in this embodiment for measuring the specular reflection light and creating the image information will be described later with reference to FIG. 2. Details of a function of creating the image information in the image information creating unit 102 will be described later with reference to FIG. 3.

A maximum/minimum value detecting unit 103 detects, from the image information made up of a plurality of pixels and obtained in the image information creating unit 102, maximum and minimum values of brightness by referring to brightness values of the pixels. The pixels subjected to the detection of brightness values are all or a part of the pixels constituting the above-mentioned image of the small area used for the discrimination of the recording medium.

An arithmetic mean value calculating unit 104 calculates an arithmetic mean value of the maximum and minimum brightness values obtained in the maximum/minimum value detecting unit 103 (i.e., a value resulting from adding the maximum and minimum values and dividing the sum by two).

A binary coding unit 105 codes the image information obtained in the image information creating unit 102 into binary values by employing, as a threshold, the arithmetic mean value obtained in the arithmetic mean value calculating unit 104. A number-of-reversals calculating unit 106 calculates the number of times the pixel values, i.e., 0 and 1, are reversed, from the binary image (also called binary data) obtained in the binary coding unit 105. Details of the calculation of the number of reversals of pixel values will be described later with reference to FIG. 6.

A recording medium type discrimination unit 107 discriminates the type of the recording medium. The type of the recording medium is discriminated by both the intensity of the specular reflection light obtained in the specular-reflection light intensity detecting unit 101 and the number of reversals of pixel values obtained in the number-of-reversals calculating unit 106. The discrimination of the type of the recording medium is performed using parameters 108 for discrimination, which are derived from a discrimination map prepared in advance and which shows the relationships of various types of recording media versus the intensity of the specular reflection light and the number of reversals of pixel values. Details of a method for discriminating the type of the recording medium will be described below. Numeral 108 denotes parameters for discrimination, which are used in discriminating the type of the recording medium in the recording medium type discrimination unit 107, i.e., thresholds decided based on distributions measured for the various types of recording media.

Thus, the process flow comprises the steps of detecting the intensity of the specular reflection light from the recording medium, calculating the number of reversals of pixel values from the image information of the arbitrary small area of the recording medium surface, and then discriminating the type of the recording medium based on those results.

Figure 2:
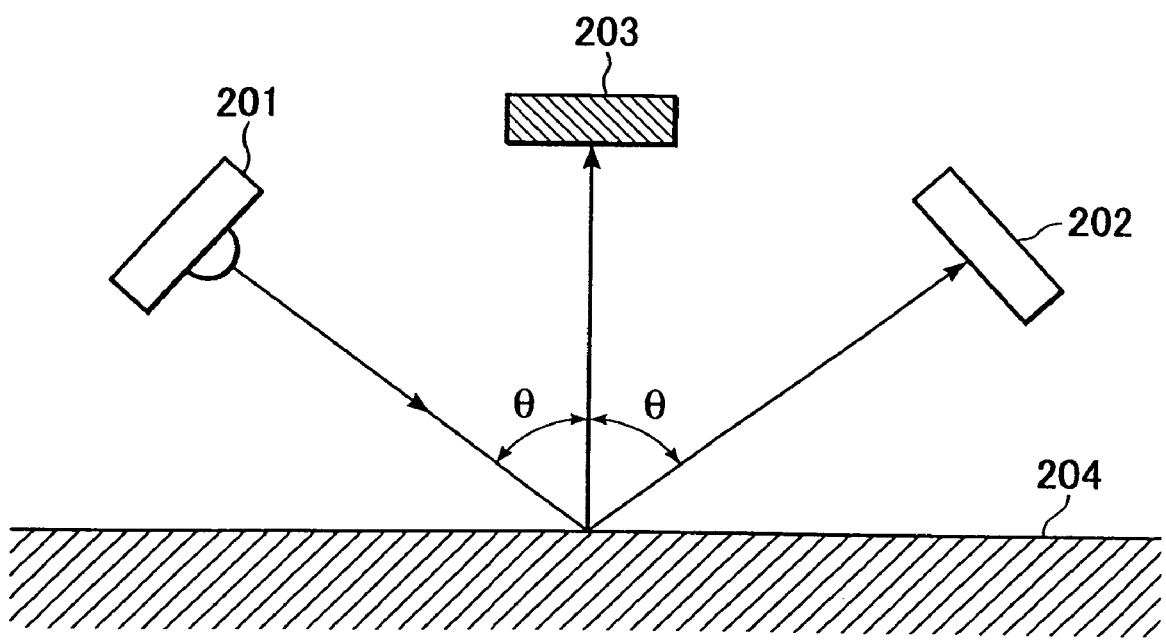
FIG. 2 is a schematic view showing a layout of a sensor for measuring a reflected light in the first embodiment.

FIG. 2 is a schematic view showing one example of the layout of a sensor section for measuring the reflected light in FIG. 1.

A light source 201 illuminates a light at an angle θ of incidence to a recording medium 204 of which type is to be discriminated. The angle θ of incidence is an arbitrary value. In this embodiment, however, when the feature of the recording medium is obtained from an image of the recording medium surface as described later, the features of each type of the recording medium appear more noticeably by setting the angle θ of incidence to a larger value. The reason is that setting the angle θ of incidence to a larger value makes shadows more apparent as the unevenness of the recording-medium surface increases, whereby a pattern of light and dark more clearly appears in the image and a brightness difference is produced. In other words, the angle θ of incidence is preferably set such that a pattern of light and dark in the image representing a brightness difference more noticeably appears. A light receiving device 202 receives a light having reflected at an angle θ of reflection equal to the angle θ of incidence at which the light was illuminated from the light source 201. The light source 201 and the light receiving device 202 receiving the specular reflection light are set in a layout such that the specular reflection light having reflected from the recording surface of the recording medium 204 subjected to illumination from the light source 201 can be received by the light receiving device 202. Another light receiving device 203 receives a light having diffusely reflected at an angle different from the angle θ of incidence at which the light was illuminated from the light source 201, (e.g., a light having reflected at a right angle relative to the recording medium in FIG. 2). The light source 201 and the light receiving device 203 receiving the diffuse reflection light are set in a layout such that the diffuse reflection light having reflected from the recording surface of the recording medium 204 can be received by the light receiving device 203. Numeral 204 denotes a recording medium of which type is to be discriminated. Though not shown in FIG. 2, lenses for use in illuminating and focusing systems are also provided.

Figure 3:
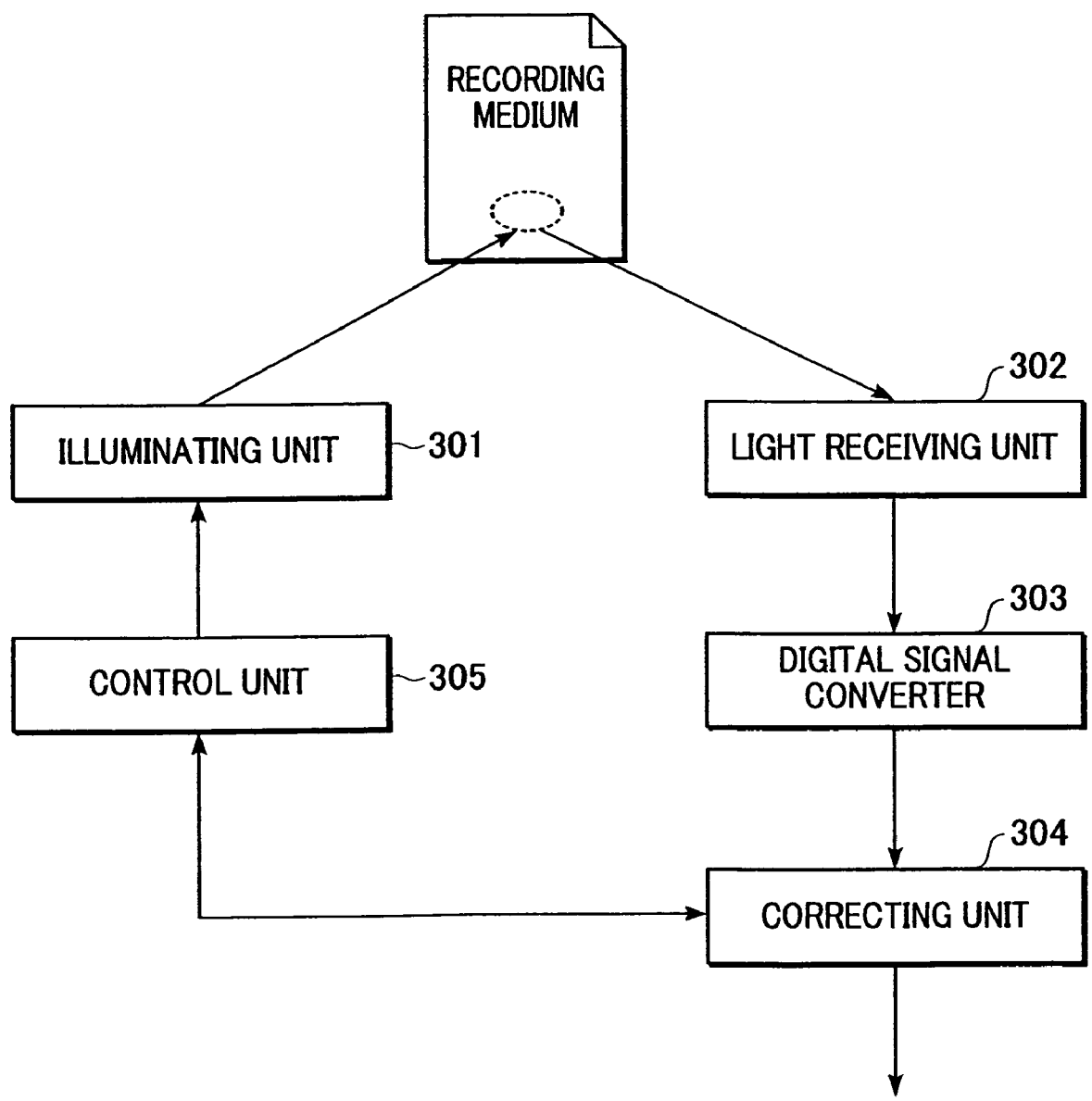
FIG. 3 is a functional block diagram of an image information creating unit in the first embodiment.

FIG. 3 is a functional block diagram of the image information creating unit 102 shown in FIG. 1.

An illuminating unit 301 illuminates the recording medium surface. In practice, the illuminating unit 301 comprises a light source, e.g., an LED, and an illumination lens. A light receiving unit 302 receives a reflected light from the recording medium surface. The light receiving unit 302 is constituted by an image sensor, an area sensor such as a CCD or CMOS, or a line sensor, and it comprises a plurality of light receiving devices.

A digital signal converter 303 is constituted by an A/D converter for converting analog signals from the light receiving unit 302, as an assembly of the plurality of light receiving devices, into digital signals for each pixel. A correcting unit 304 corrects the signals from the digital signal converter 303. The correction includes, for example, shading correction of the light source and correction for suppressing variations among the pixels. Another example is a process for converting a bit length of the digital signal outputted from the digital signal converter 303 into a smaller value.

A control unit 305 comprises a CPU, logics, etc. for executing various controls of the image information creating unit 102, such as the illuminating unit 301 and the correcting unit 304. The control unit 305 first controls the illuminating unit 301 to illuminate the recording medium surface, and then controls the light receiving unit 302 to receive a reflected light from the recording medium surface and to output a measured value. Subsequently, the digital signal converter 303 is controlled to convert the measured value, which is in the form of an analog signal for each pixel in the reflected light received by the light receiving unit 302, into a digital signal. Further, the control unit 305 controls the correcting unit 304 to execute various corrections to the digital signal. A subsequent process is performed using image information that is outputted from the correcting unit 304 and is constituted as brightness information for each of a plurality of pixels. At this time, a process of restricting an image area to be processed, for which the light receiving unit 302 can create the image information, may be additionally provided.

Figure 4:
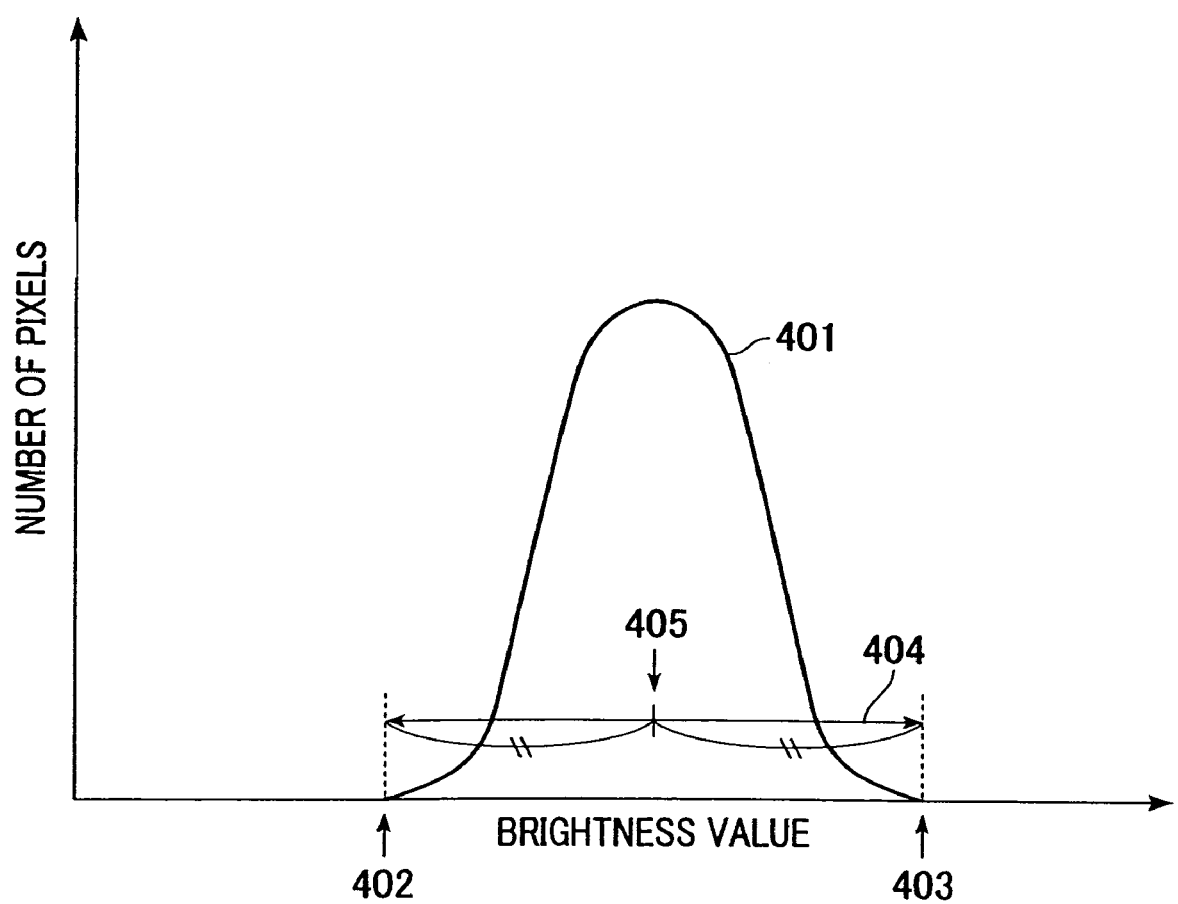
FIG. 4 is a histogram showing the relationship between the number of pixels and a brightness value for an image in the first embodiment.

FIG. 4 is a histogram showing the relationship between the number of pixels and a brightness value for an image. The horizontal axis represents the brightness value, and the vertical axis represents the number of pixels having respective brightness values.

Numeral 401 denotes a histogram of the pixels constituting the image information in terms of brightness. The histogram ideally exhibits a normal distribution, as shown, when measuring an image made up of a number of pixels not smaller than a certain value. Numeral 402 denotes a minimum of the brightness values of the pixels constituting the image information. Numeral 403 denotes a maximum of the brightness values of the pixels constituting the image information. Numeral 404 denotes a difference between the maximum and minimum brightness values of the pixels constituting the image information. Numeral 405 denotes a value at which the brightness difference 404 is divided into two equal parts, i.e., an arithmetic mean value of the maximum and minimum brightness values. In this embodiment, the arithmetic mean value is used as a threshold for the binary coding. In the following description of the present invention, the values denoted by 404 and 405 will be referred to as "brightness difference" and "arithmetic mean value", respectively.

Figure 5A:
FIGS. 5A and 5B show, by way of example, an image showing surface conditions of a recording medium and an image obtained after binary coding in the first embodiment, respectively.
Figure 5B:
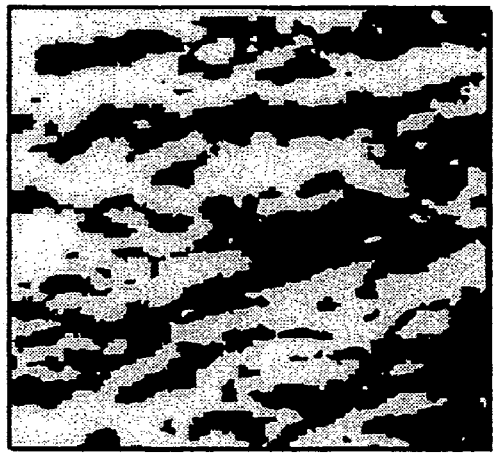

FIGS. 5A and 5B respectively show examples of images obtained before and after the binary coding executed in the binary coding unit 105 shown in FIG. 1.

FIG. 5A is an image of a photograph before the binary coding obtained when the image information is created from plain paper. Note that an image of the recording medium surface obtained in the image information creating unit 102 is constituted by multi-value brightness information. Also, since image contrast is in fact not as clear as shown in FIG. 5A, the illustrated image is adjusted in contrast for easier understanding. FIG. 5B shows an image obtained after binary-coding the image shown in FIG. 5A by employing, as a threshold, the arithmetic mean value 405 obtained in the arithmetic mean value calculating unit 104. Thus, the image after the binary coding is provided as a collection of pixels having information of one of a possible two values, i.e., white or black (data 1 or 0).

FIG. 6 is a representation for explaining the number of times each pixel value is reversed between 0 and 1 after the binary coding in the number-of-reversals calculating unit 106 shown in the first embodiment. As shown in FIG. 6, a one-dimensional linear image is obtained as a target image for processing, and the image after the binary coding is constituted by an array of white and black pixels. The white and black pixels are in fact pixels each having a value of 0 or 1. (Although this embodiment is described in connection with, by way of example, the case in which the black pixel has a value of 0 and the white pixel has a value of 1, the white and black pixels may be given values in a different way, such that the white pixel has a value of 0 and the black pixel has a value of 1).

Numeral 601 denotes a pixel at a certain position in an image after the binary coding. The pixel 601 is a black pixel and has a value of 0. A pixel on the right side of the pixel 601 is a white pixel. Subsequently, as shown, a black pixel, a black pixel, a black pixel, a white pixel, a white pixel, and so on continue. Numeral 602 denotes a pixel at the 20-th position counted from the pixel 601 at a certain position. The pixel 602 is a white pixel and has a value of 1.

The white and black pixels (values of 1 and 0) after the binary coding are reversed from one to the other at points indicated by arrows shown in FIG. 6. Thus, each arrow indicates a change from the black pixel to the white pixel (from 0 to 1) or a change from the white pixel to the black pixel (from 1 to 0). Assuming that the number of reversals before the pixel 601 is (N−1), since the pixel value is reversed 11 times between the pixels 601 and 602, the number of reversals before the pixel 602 is (N+10). The number of reversals of pixel values in the target image is calculated in such a way and is employed as a parameter for discriminating the type of the recording medium.

In this embodiment of the present invention, two kinds of features of the recording medium surface are obtained as parameters, and the type of the recording medium is discriminated based on these parameters. By measuring the intensity of the specular reflection light described above, the feature regarding the magnitude of unevenness of the recording medium surface is obtained. Also, by measuring the number of reversals of pixel values corresponding to changes in brightness information in accordance with an array of successive pixels, the feature regarding the period of unevenness of the recording medium surface is obtained. Herein, the magnitude of unevenness of the recording medium surface is referred to as a "smoothness or gloss feature", and the period of unevenness of the recording medium surface is referred to as a "surface shape feature".

A manner of discriminating the type of the recording medium based on those two features will be described below.

FIG. 7 is a discrimination map showing the relationships of various types of recording media versus the number of reversals of pixel values and the intensity of the specular reflection light. Values denoted by A1 to A3 and B1 to B3 in FIG. 7 are used as the parameters 108 for discrimination shown in FIG. 1. Circular regions in FIG. 7 each represent a set of points corresponding to the measured results, and discrimination areas are defined by dividing a map plane as shown based on the circular regions.

Numeral 701 represents an area in which the recording medium under measurement is discriminated to be plain paper. Numeral 702 represents an area in which it is discriminated to be ink-jet coated paper. Numeral 703 represents an area in which it is discriminated to be glossy paper. Numeral 704 represents an area in which it is discriminated to be photographic glossy paper. Numeral 705 represents an area in which it is discriminated to be a glossy film. Numeral 706 represents an area in which it is discriminated to be an OHP film.

In FIG. 7, the vertical and horizontal axes representing the number of reversals of pixel values and the intensity of the specular reflection light are each divided by three points to define four areas for each axis. However, an area used for discriminating the recording medium is not necessarily limited to a rectangular shape. Also, the areas corresponding to values of the number of reversals not larger than A1 and sandwiched between the plain paper discrimination area 701 and the OHP film discrimination area 706 are not allocated as areas used for discriminating the recording medium. Those areas can also be used as an area in which the recording medium is discriminated to be plain paper, or an area in which the recording medium is discriminated to be an OHP film. Stated otherwise, while it is required that, in each of the circular regions shown in FIG. 7, the recording medium be discriminated to be a particular type of recording medium, discrimination in other areas can be performed in a flexible manner.

A description is now briefly made of tendencies in the features of six types of recording media which are to be discriminated in this embodiment, and in the relationships of the various types of recording media versus the intensity of the specular reflection light and the number of reversals of pixel values. The six types of recording media are plain paper (LC-301; made by Canon Inc.), ink-jet coated paper (HR-101s; made by Canon Inc.), glossy paper (GP-301; made by Canon Inc.), photographic glossy paper (PR-101; made by Canon Inc.), a glossy film (HG-201; made by Canon Inc.), and an OHP film (CF-102).

Table 1, given below, lists results obtained by measuring a gloss (specular gloss) of a surface of each recording medium using a glossmeter (Precise Glossmeter GM-26D; made by Murakami Color Research Laboratory, Co., Ltd.). The angle of reflection in the measurement was 60 degrees.

TABLE 1

|  | Plain paper | Coated paper | Glossy paper | Photographic glossy paper | Glossy film | OHP film |
|---|---|---|---|---|---|---|
| Gloss (%) | 3.7 to 5.0 | 2.4 to 4.0 | 20.4 | 51.3 | 88.1 | 121.7 |

Table 2, given below, lists results obtained by measuring surface roughness of each type of recording medium with a non-contact surface shape measuring device (three-dimensional laser interferometer New View 5000; made by ZYGO)

TABLE 2

|  | Plain paper | Coated paper | Glossy paper | Photographic glossy paper | Glossy film | OHP film |
|---|---|---|---|---|---|---|
| Mean roughness Ra (μm) | 2.75 to 3.20 | 1.19 | 0.21 | 0.08 | 0.05 | 0.15 |
| Maximum roughness Rmax (μm) | 28.9 to 33.5 | 21.9 | 16.0 | 1.05 | 0.83 | 10.9 |

Plain paper is a general recording medium that is also used in copying machines, etc. Pulp fibers making up the plain paper appear on a paper surface. As listed in Table 2, there is a tendency that the magnitude of unevenness of the plain paper is larger than those of the other types of recording media, and the unevenness is reflected as inconsistencies in brightness in the created image information. Such a tendency results in a low gloss level. Further, changes in asperities resulting from the unevenness are more moderate than those in the other recording media and are related to a larger period of the unevenness. In addition, more moderate changes in asperities are related to fewer numbers of reversals of pixel values in the image after the binary coding.

Ink-jet coated paper is a recording medium formed by coating a pigment, e.g., silica, on a surface of plain paper. Though depending on an amount of the coated pigment, the pigment is generally coated so as to fill recesses in surface unevenness caused by pulp fibers. Therefore, the unevenness of the ink-jet coated paper is smaller than that of the plain paper, resulting in a smaller surface roughness and a shorter period of the unevenness. This leads to a tendency that the number of reversals of pixel values increases. The gloss level of the ink-jet coated paper is comparable to or lower than that of the plain paper.

Glossy paper is a recording medium formed by coating several layers of an ink accepting substance on a surface of paper serving as a base. An alumina-based pigment or a PVA-based swelling resin is used as an ink accepting layer that constitutes a surface layer of the recording medium. The glossy paper has a smaller magnitude of unevenness than the plain paper and the ink-jet coated paper, and thus it has a higher smoothness and a higher gloss level. The period of unevenness of the glossy paper is also smaller than that of the plain paper and the ink-jet coated paper. This leads to a tendency that the number of reversals of pixel values increases.

Photographic glossy paper is a recording medium formed by processing the photographic glossy paper in a manner similar to the above-mentioned glossy paper. In addition, various improvements are performed on a paper surface to realize an image quality and weatherability comparable to those of a photograph printed on photographic paper. The photographic glossy paper has a smaller magnitude of unevenness than the glossy paper, and thus it has a higher smoothness and a higher gloss level. As a result, there is a tendency that the photographic glossy paper provides a slightly higher number of reversals of pixel values than the glossy paper.

A glossy film is a recording medium formed by coating an ink accepting layer on a surface of a film that is made of, e.g., white PET, which serves as a base. The glossy film has a smaller magnitude of unevenness than the glossy paper, and thus it has a higher smoothness and a higher gloss level. Also, the smoothness of the glossy film is slightly higher than that of the photographic glossy paper. The reason is that unevenness (smoothness) of a material used as the base affects the unevenness of the recording medium surface. More specifically, comparing the glossy film using a film as the base to the photographic glossy paper using paper as the base, the glossy film uses a material having a higher smoothness as the base, and thus exhibits a slightly higher smoothness. Further, the gloss level of the glossy film tends to be slightly higher than that of the photographic glossy paper. The reason is that, when measuring the intensity of the specular reflection light, the specular reflection light contains not only a light reflected by the recording medium surface, but also a light reflected by a base or face of the recording medium, which increases the gloss level. Moreover, there is a tendency that the glossy film provides a slightly higher number of reversals of pixel values than the glossy paper.

An OHP film is a recording medium formed by coating an ink accepting layer on a surface of a transparent film serving as a base. In this embodiment, the OHP film that was measured was coated with a fine powder of silica in order to prevent the film from sticking. Because the specific nature of the OHP film is such that it has a higher smoothness than the glossy film, the surface roughness of the OHP film should be smaller than that of the glossy film. However, actual measurement provided a result that the OHP film had a larger surface roughness due to the coarse particles of the silica. Also, since the light illuminated from the light source may pass through the recording medium without being reflected by the recording medium surface, the brightness value obtained from a reflected light, which is measured as a component of diffuse reflection light, is very small and the brightness difference is hardly noticeable. Hence, the brightness value is hardly changed and the number of reversals of pixel values is also reduced. Further, since most of the light reflected by the recording medium surface is a component of specular reflection light, the gloss level of the OHP film tends to be higher than those of the other types of recording media.

The above-described relationships of the various types of recording media versus the intensity of the specular reflection light, the brightness difference and the number of reversals of pixel values are summarized in Table 3 given below.

TABLE 3

| | Plain paper (a) | Coated paper (b) | Glossy paper (c) | Photo-graphic glossy paper (d) | Glossy film (e) | OHP film (f) |
|---|---|---|---|---|---|---|
| Specular reflection light intensity | low | low | medium | high | higher than (d) | higher than (d) |
| Number of reversals | small | medium | large | larger than (c) | larger than (c) | hardly appreciable |

As described above, each type of recording medium has features represented by the gloss level obtained from the intensity of the reflected light from the recording medium and by surface conditions indicative of the period and the unevenness of the recording medium surface. In this embodiment, those features are reflected in two parameters, i.e., the intensity of the specular reflection light (gloss) and the number of reversals of pixel values, which are then used for the discrimination. As a result, the discrimination between the plain paper and the ink-jet coated paper, which has been difficult when discriminating using the intensity of the specular reflection light, i.e., the glossy as the only discrimination parameter, can be made with higher accuracy by utilizing the number of reversals of pixel values as well. Also, the discrimination between the photographic glossy paper and the glossy film, which has been difficult when the only discrimination parameter is the parameter obtained from the image information, e.g., the number of reversals of pixel values, can reliably be made by using the intensity of the specular reflection light as a discrimination parameter as well.

In the present invention, while the type of the recording medium is discriminated by confirming the features of the recording medium in advance, and then comparing the features with the corresponding parameters, it is important that the gloss level and the surface shape also be used for the discrimination.

An improvement in the accuracy of the above-described discrimination is greatly affected by both the size of the area referred to for the discrimination and the number of pixels (resolution) making up an image of the area. Therefore, a description is now made of the number of pixels and the pixel pitch. The number of pixels used for the discrimination is not less than 50, and the pixel pitch used for the discrimination is not larger than 50 µm (resolution is not less than 500 dpi). To realize the discrimination at a certain level of reliability, however, it is preferable that the number of pixels be not less than 100 and the pixel pitch be not larger than 20 µm (resolution be not less than 1200 dpi). Note that the above-mentioned conditions are not necessarily required in order to realize the discrimination. Further, the required number of pixels and the pixel pitch vary depending on not only conditions of an optical system (sensitivity of the sensor for measuring the reflected light, etc.), but also on the recording medium of which type is to be discriminated.

Figure 8:
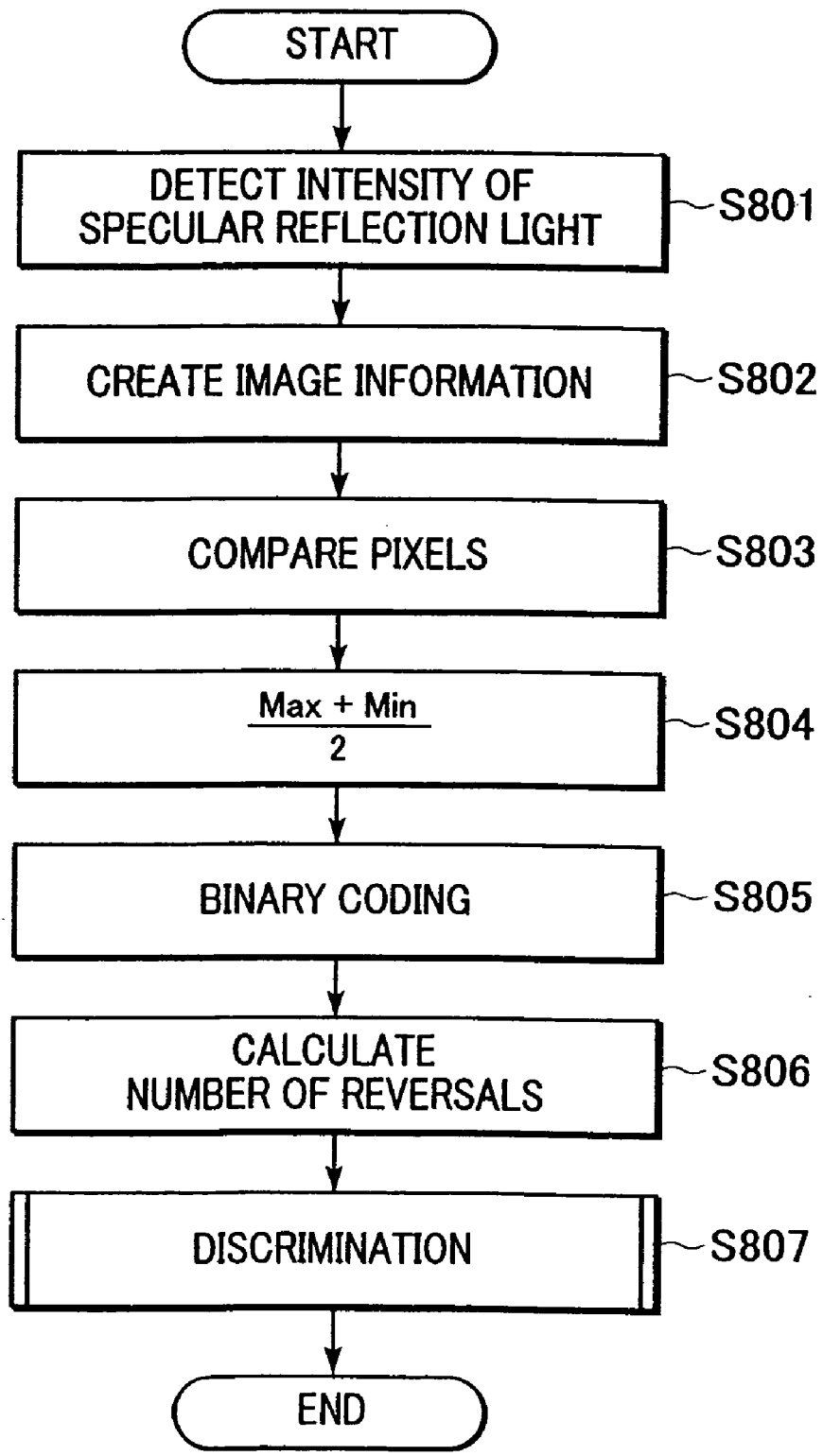
FIG. 8 is a flowchart showing a flow of a recording medium type discrimination process in the first embodiment.

FIG. 8 is a flowchart showing a flow of a recording medium type discrimination process in this first embodiment.

In step 801 (S801), the intensity of the specular reflection light is detected. In step S802, image information is created. In step S803, pixels are compared with each other based on the image information obtained in step S802. Specifically, maximum and minimum brightness values are detected. In step S804, an arithmetic mean value of the maximum and minimum brightness values detected in step S803 is calculated. In step S805, binary coding is executed using, as a threshold, the arithmetic mean-value calculated in step S804. In step S806, the number of reversals of pixel values, i.e., 0 and 1, is calculated from an image obtained after the binary coding. In step S807, the type of the recording medium is discriminated based on the intensity of the specular reflection light obtained in step S801 and the number of reversals of pixel values obtained as a feature variable in step S806.

In the flowchart of the recording medium type discrimination process shown in FIG. 8, the intensity of the specular reflection light is detected in step S801, i.e., at the beginning of the process flow. However, it is only required that the intensity of the specular reflection light be detected before the type of the recording medium is discriminated in step S807.

Figure 9:
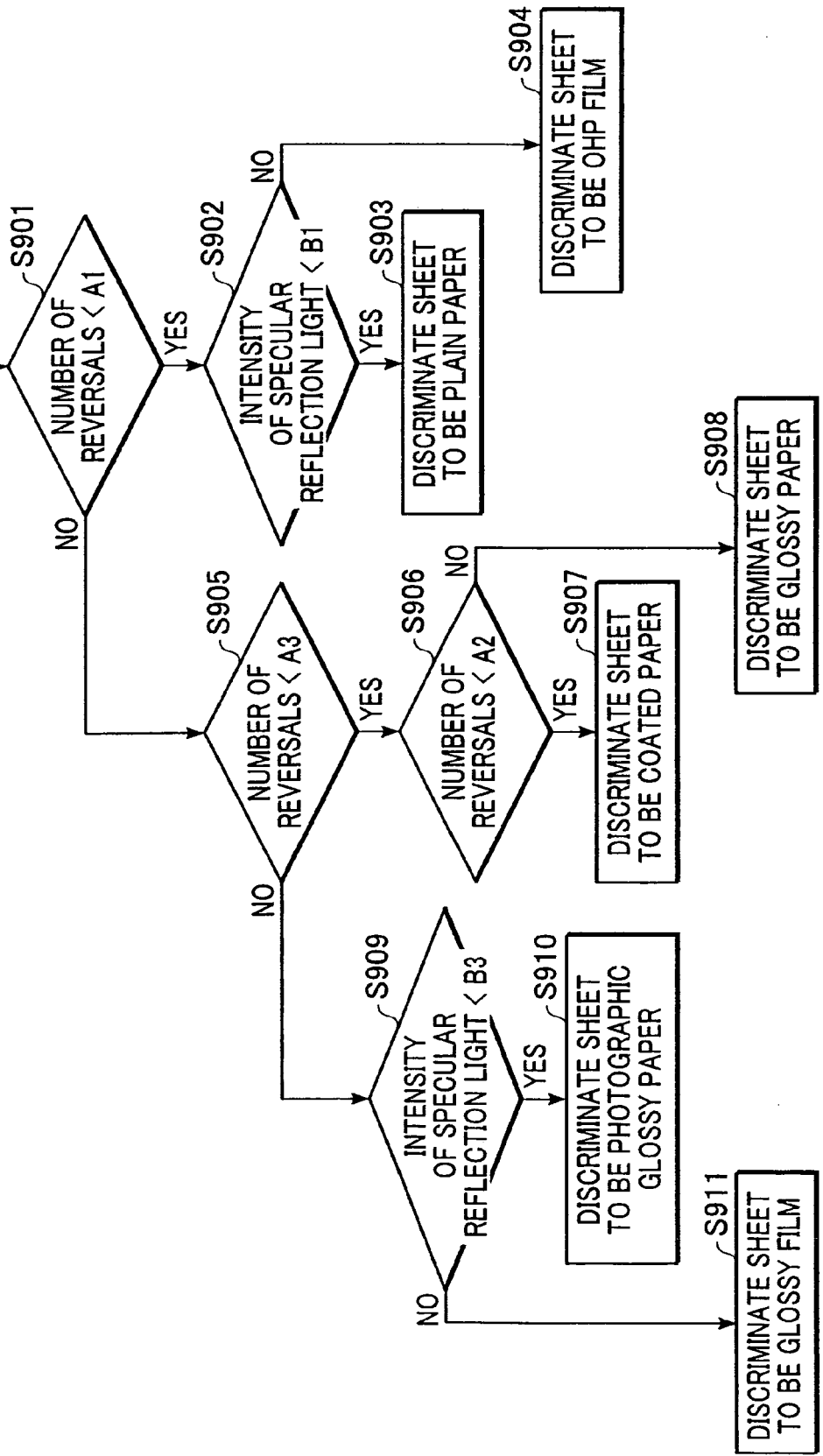
FIG. 9 is a flowchart showing a process flow for discrimination of the type of the recording medium in the first embodiment.

FIG. 9 is a flowchart showing a process flow for discrimination of the type of the recording medium in step S807 shown in FIG. 8.

Based on the discrimination map shown in FIG. 9, the type of the recording medium is discriminated using the two obtained parameters as follows. For this discussion, assume that the values A1, A2, A3, B1, B2 and B3 used in the following description satisfy relationships given below. B1, B2 and B3 are values representing the intensity of the specular reflection light and satisfy a relationship of B1<B2<B3. Also, A1, A2 and A3 are values representing the number of reversals of pixel values and satisfy a relationship of A1<A2<A3.

In step 901 (S901), it is determined whether the number of reversals is smaller than A1. If the number of reversals is smaller than A1, the process flow advances to step S902, and if not, the process flow advances to step S905.

In step S902, it is determined whether the intensity of the specular reflection light is smaller than B. If the intensity of the specular reflection light is smaller than B1, the process flow advances to step S903, and if not, the process flow advances to step S904. Note that, in step S902, the parameter B1 used for discriminating the type of the recording medium may be replaced by B2 or B3.

In step S903, the type of the recording medium is discriminated to be plain paper. In step S904, the type of the recording medium is discriminated to be an OHP film.

In step S905, it is determined whether the number of reversals is smaller than A3. If the number of reversals is smaller than A3, the process flow advances to step S906, and if not, the process flow advances to step S909.

In step S906, it is determined whether the number of reversals is smaller than A2. If the number of reversals is smaller than A2, the process flow advances to step S907, and if not, the process flow advances to step S908. Note that, in step S906, the parameter A2, which represents the number of reversals and is used for discriminating the type of the recording medium, may be replaced by the parameter B1, which represents the intensity of the specular reflection light.

In step S907, the type of the recording medium is discriminated to be ink-jet coated paper. In step S908, the type of the recording medium is discriminated to be glossy paper.

In step S909, it is determined whether the intensity of the specular reflection light is smaller than B3. If the intensity of the specular reflection light is smaller than B3, the process flow advances to step S910, and if not, the process flow advances to step S911.

In step S910, the type of the recording medium is discriminated to be photographic glossy paper. In step S911, the type of the recording medium is discriminated to be a glossy film.

In this embodiment, the processing sequence is set taking into account that any type of recording medium is discriminated with the discriminating process through a comparable number of steps. As an alternative, when it is desired to quickly discriminate a particular type of the recording medium for the reason that the particular type of the recording medium is used at higher frequency, the discrimination may be executed in accordance with a different processing sequence. In such a case, the type of the recording medium can also be discriminated in a similar manner based on the discrimination map shown in FIG. 7.

For the areas that are not allocated in FIG. 7 as areas used for discriminating the recording medium to be a particular type of recording medium, e.g., for the area in which the intensity of the specular reflection light is larger than B1 and the number of reversals is not smaller than A1, but smaller than A2, the flowchart of FIG. 9 is designed so as to discriminate the type of the recording medium to be ink-jet coated paper. However, the flowchart may be modified such that, for those areas, the absence of any corresponding type of recording medium is discriminated and the process for discriminating the type of the recording medium is executed again. As an alternative, error processing to return an error signal indicating the absence of any type of recording medium may be executed, and an error screen for notifying the user of the absence of any type of recording medium may be displayed.

Figure 10:
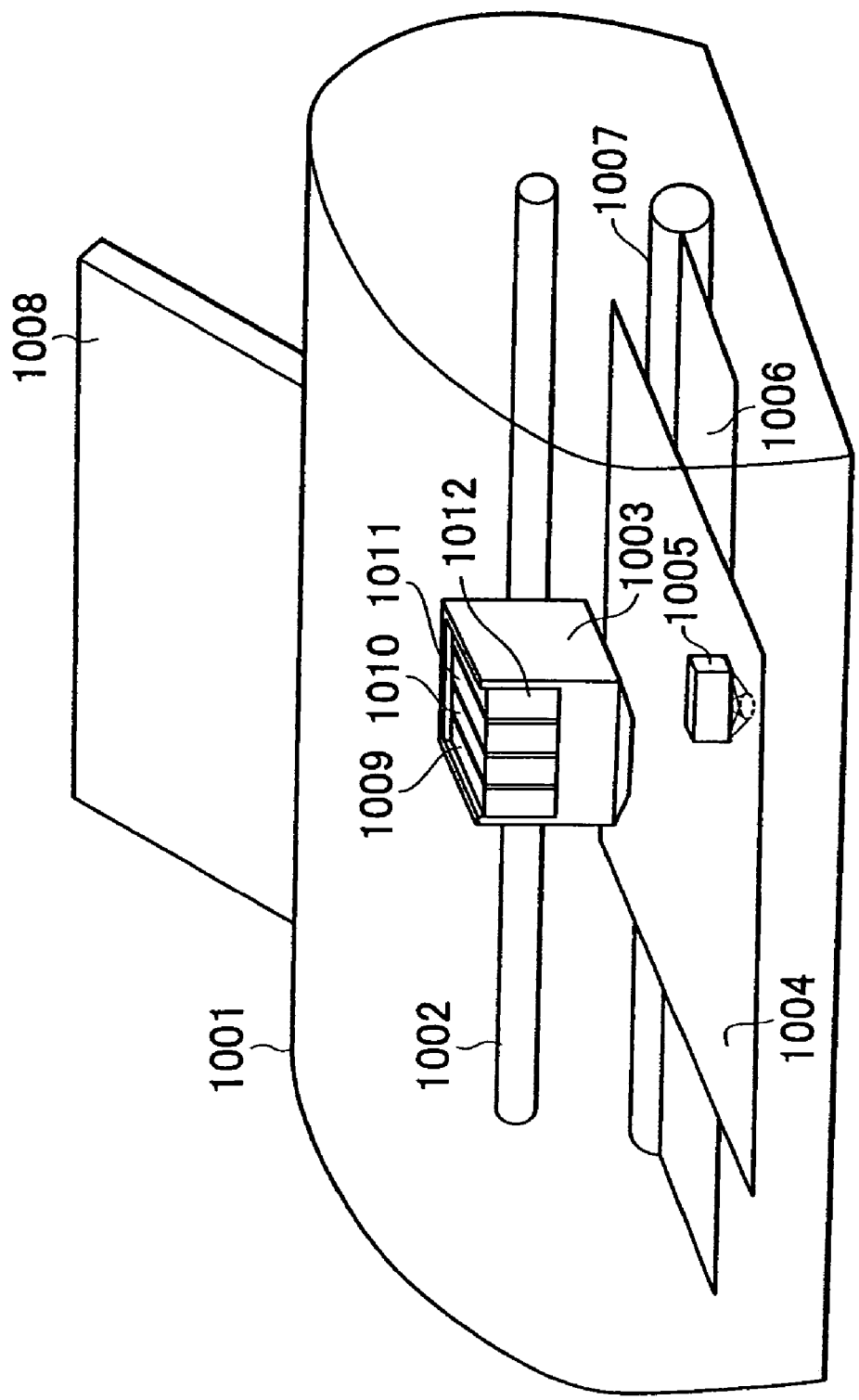
FIG. 10 is a schematic perspective view of a recording apparatus according the first embodiment.

FIG. 10 is a schematic perspective view showing one example construction of a recording apparatus according the first embodiment.

Numeral 1001 denotes a recording apparatus body. In this embodiment, the recording apparatus is assumed to be of the ink-jet type in the form of a serial printer. As shown in FIG. 10, the recording apparatus comprises a guide rail 1002, a carriage 1003, an optical sensor 1005, a platen 1006, a feed roller 1007, an auto-sheet feeder 1008, and so on.

The guide rail 1002 reciprocally scans the carriage 1003 in the direction of main scan. The carriage 1003 detachably mounts thereon cartridge-type recording heads 1009, 1010, 1011 and 1012 corresponding to ink tanks of plural colors (e.g., four colors of black (K), cyan (C), magenta (M) and yellow (Y)). Numeral 1004 denotes a recording medium on which an image is recorded by the recording apparatus 1001. For discriminating the type of the recording medium, the optical sensor 1005 comprises a sensor for measuring the intensity of a specular reflection light from the recording medium 1004, and an image sensor for producing image information regarding a surface of the recording medium 1004. The platen 1006 restricts the recording surface of the recording medium 1004 to be flat. The feed roller 1007 feeds the recording medium 1004 in the direction of sub-scan. For the recording medium 1004 fed by the feed roller 1007, the intensity of the specular reflection light is measured and the image information representing surface conditions is produced. The auto-sheet feeder 1008 supplies and advances the recording medium 1004 to a position at which an image is recorded.

The cartridge-type recording heads 1009, 1010, 1011 and 1012 correspond to the ink tanks of plural colors. These recording heads may have any one of various suitable structures. For example, the recording head may be separated into an ink tank containing ink as a recording agent and may be detachably attached to a cartridge body, and the recording head may be an ink-jet head cartridge supported on the cartridge body and it may have an ink ejection unit. In other words, the ink ejection unit and the ink tank may be separable from each other. With the ink ejection unit and the ink tank being separable from each other, only the ink tank can be solely replaced, for example, when the amount of ink remaining in the tank has become small. Alternatively, the structure may be modified such that only the ink ejection unit is constituted in the form of a cartridge and is supplied with ink through a tube or the like from the ink tank disposed in another position within the apparatus. It is also possible to employ, in addition to the recording heads having the above-mentioned structure, cartridges corresponding to plural kinds of ink of the same color, but having different densities. Further, a plurality of recording heads corresponding to different recording densities may be employed.

As shown in FIG. 10, the recording apparatus can be constructed such that the optical sensor 1005 is disposed in the recording apparatus body and has an additional function of discriminating the type of the recording medium based on the intensity of the specular reflection light and the image information, both of which are obtained from the optical sensor 1005.

Figure 11:
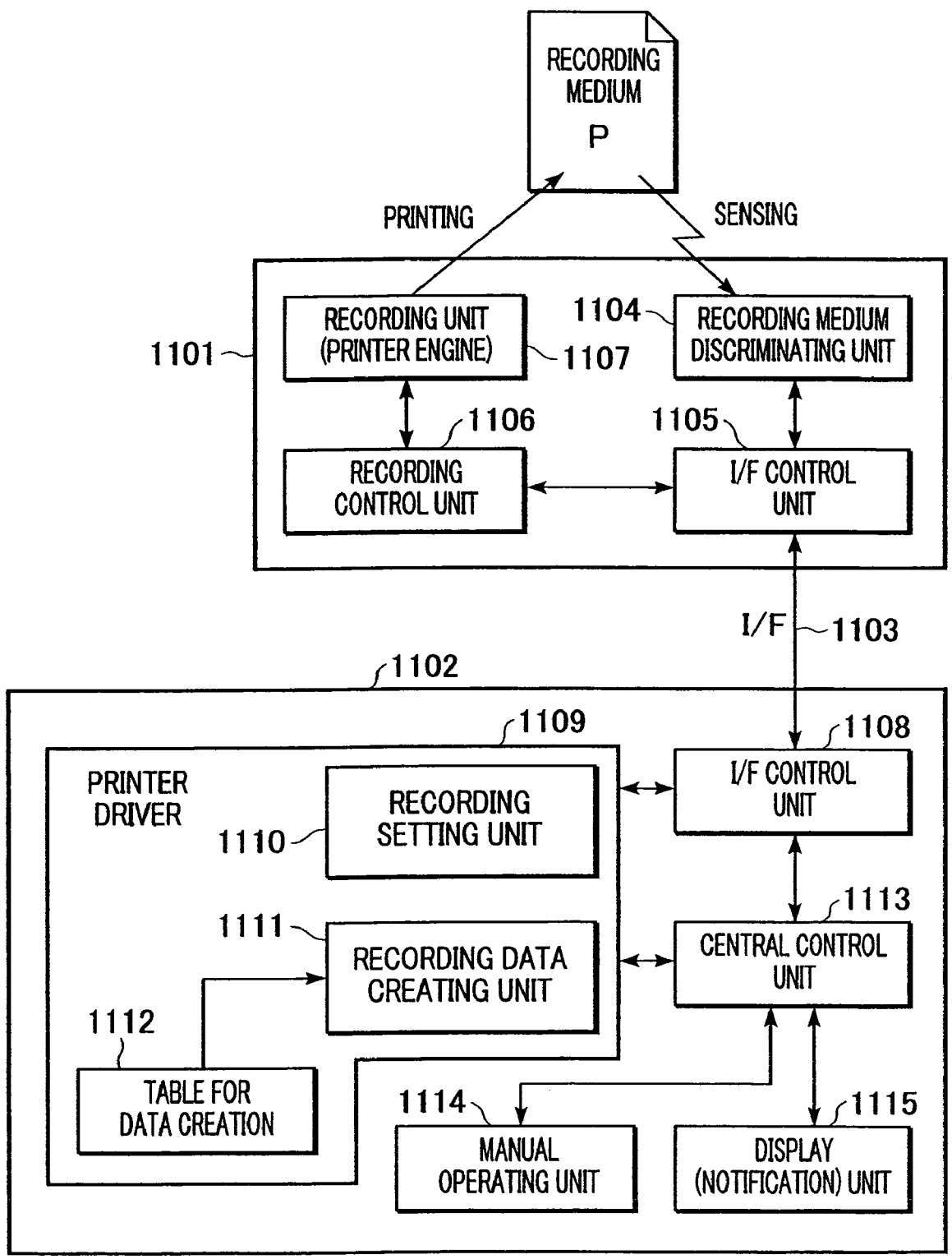
FIG. 11 is a functional block diagram showing the system configuration in the first embodiment.

FIG. 11 is a functional block diagram of a system configuration.

Numeral 1101 denotes an ink-jet color recording apparatus for forming an image and recording the image on a recording medium P. The color recording apparatus 1101 comprises functional blocks 1104 to 1107. A host 1102 is connected to the color recording apparatus 1101 and supplies recording data to be recorded on the recording medium. The host 1102 comprises functional blocks 1108 to 1115. Note that, of the configuration of the color recording apparatus 1101 and the host 1102, the functions which are regarded as not essential for explaining the features of this embodiment are omitted from the drawing.

A communication interface 1103 interconnects the recording apparatus 1101 and the host 1102. While there are various communication interfaces, such as IEEE1284, USB (Universal Serial Bus) and IEEE1394, USB is the assumed communication interface in this embodiment.

A recording medium type discrimination unit 1104 discriminates the type of the recording medium P. From the viewpoint of function, the unit 1104 is divided into an image information creating section for detecting the intensity of the specular reflection light from the recording medium P and creating image information regarding an arbitrary area in a surface of the recording medium P with the optical sensor 1005, and a recording medium type discrimination section for discriminating the type of the recording medium based on the created image information. The recording medium P is stacked in a paper supply tray or cassette equipped in the recording apparatus 1101.

An I/F control unit 1105 fulfills an interface function of the recording apparatus 1101. Because the interface is assumed to be USB in this embodiment, the I/F control unit 1105 is constituted by a controller on the side of a USB peripheral unit. Transmission of information regarding the type of the recording medium, transmission and reception of recording data and control commands, etc. are performed via the I/F control unit 1105. Also, status information indicating, e.g., an error, and a communication state occurring in the recording apparatus body, are returned to the host 1102 if requested.

A recording control unit 1106 receives recording data transmitted from the host 1102 and develops it in a printer engine. The recording control unit 1106 controls the printer engine in accordance with recording control commands contained in the recording data. More specifically, the host 1102 transmits, as the recording data, data comprising binary data for recording (or intermediate data before binary coding in some cases) and various commands for controlling the amount of jetted ink, the number of passes, the recording direction, and the feed amount of the recording medium.

Numeral 1107 denotes a recording unit that is also called a printer engine. The recording unit 1107 records an image on the recording medium P in accordance with the recording data developed in the recording control unit 1106. Since the color recording apparatus 1101 is of the ink-jet type, an image is formed with ejection of ink.

An I/F control unit 1108 fulfills an interface function of the host 1102. The I/F control unit 1108 is constituted by a controller on the USB host side and has functions as a USB host. Software, such as an OS and a driver, also constitute part of the USB host functions.

Numeral 1109 denotes a printer driver in the form of software for executing, in the host 1102, various settings for recording, creation of the recording data, and control of the recording apparatus. The printer driver 1109 comprises various functional blocks 1110 to 1112.

A recording setting unit 1110 executes various kinds of recording settings, such as setting of the recording medium and setting of recording quality. The recording setting unit 1110 has functions of receiving instructions and inputs from the user and displaying or notifying details of the setting. The recording setting unit 1110 may also have a function of automatically executing the recording setting based on the information regarding the type of the recording medium transmitted from the recording apparatus 1101.

A recording data creating unit 1111 creates the recording data. More specifically, in accordance with the recording setting made in the recording apparatus 1101 and the recording setting unit 1110, the recording data creating unit 1111 executes various kinds of image processing, such as color conversion and binary coding, and creates data for the recording and commands for the recording apparatus to perform recording control. These data for the recording and commands for the control are transmitted as the recording data to the recording apparatus 1101.

A table 1112 is used when creating the recording data in the recording data creating unit 1111. The table 1112 can be updated or added with new matter.

A central control unit 1113 controls the various functions of the host 1102. From the view of functions, a CPU corresponds to the central control unit 1113. Numeral 1114 denotes an input operating unit. The input operating unit 1114 comprises various input devices used for reflecting the user's intention for the recording setting. A display (notification) unit 1115 informs the recording setting to the user. The recording setting can be displayed or notified, for example, by employing a display, such as a monitor, or communicating it with voices.

Thus, the printing system of this embodiment comprises: a color recording apparatus which is provided with the optical sensor 1005 and has the function of discriminating the type of the recording medium; a data processor such as a host which has the function of creating the recording data and the control commands in accordance with instructions and selections by the user and with the information obtained regarding the type of the recording medium; and a two-way communication interface connecting the recording apparatus and the data processor. This embodiment has been described as an example of a system configuration in which the recording apparatus 1101 incorporates all of the functions of the recording medium type discriminating unit 1104 (which have been described in detail with reference to FIG. 1). However, a part or all of those functions may be incorporated in the data processor, i.e., the host. With at least a part of those functions incorporated in the data processor, the operation can be performed in a more flexible manner than when processing all of those functions in the recording apparatus body. More specifically, it is possible to easily correct and change the parameters for discriminating the type of the recording medium when a new type of the recording medium is added.

As described above, by obtaining a parameter indicated by the intensity of the specular reflection light from the recording medium and a parameter representing surface conditions of the recording medium derived from an image of a predetermined area of the recording medium surface, and then discriminating the type of the recording medium based on the obtained parameters, the discrimination of the type of the recording medium can be realized with higher accuracy. Particularly, it is possible to simultaneously realize the discrimination between plain paper and ink-jet coated paper, which has hitherto been difficult in the case of employing the reflection optical sensor, and the discrimination between photographic glossy paper and a glossy film, which has been difficult in the past with the use of the image sensor.

While this embodiment employs as the threshold for use in the binary coding the arithmetic mean value of the maximum and minimum brightness values, similar advantages can also be obtained using another parameter indicating the magnitude of unevenness of the recording medium surface, such as another kind of arithmetic mean value (i.e., a mean value resulting from summing brightness values of pixels contained in the image information and dividing the sum by the total number of the pixels making up the image), or the brightness value at a peak of the histogram.

While this embodiment employs the discrimination parameters 108 in discriminating the type of the recording medium, similar advantages can also be obtained by employing a discrimination table in which the types of recording media are related to the number of reversals of pixel values and the intensity of the specular reflection light based on the relationships shown in FIG. 7.

Furthermore, in this embodiment, the number of reversals is provided by counting both changes from the black pixel to the white pixel and from the white pixel to the black pixel. However, similar advantages can also be obtained by counting, as the number of reversals, only the change from the black pixel to the white pixel or only the change from the white pixel to the black pixel.

(Second Embodiment)

A second embodiment implementing the present invention will be described below in detail with reference to the drawings.

While in the first embodiment the type of the recording medium is discriminated using the intensity of the specular reflection light and the number of reversals after the binary coding, a recording medium discriminating method of this second embodiment discriminates the type of the recording medium by using the intensity of the specular reflection light and a run-length code amount.

Figure 12:
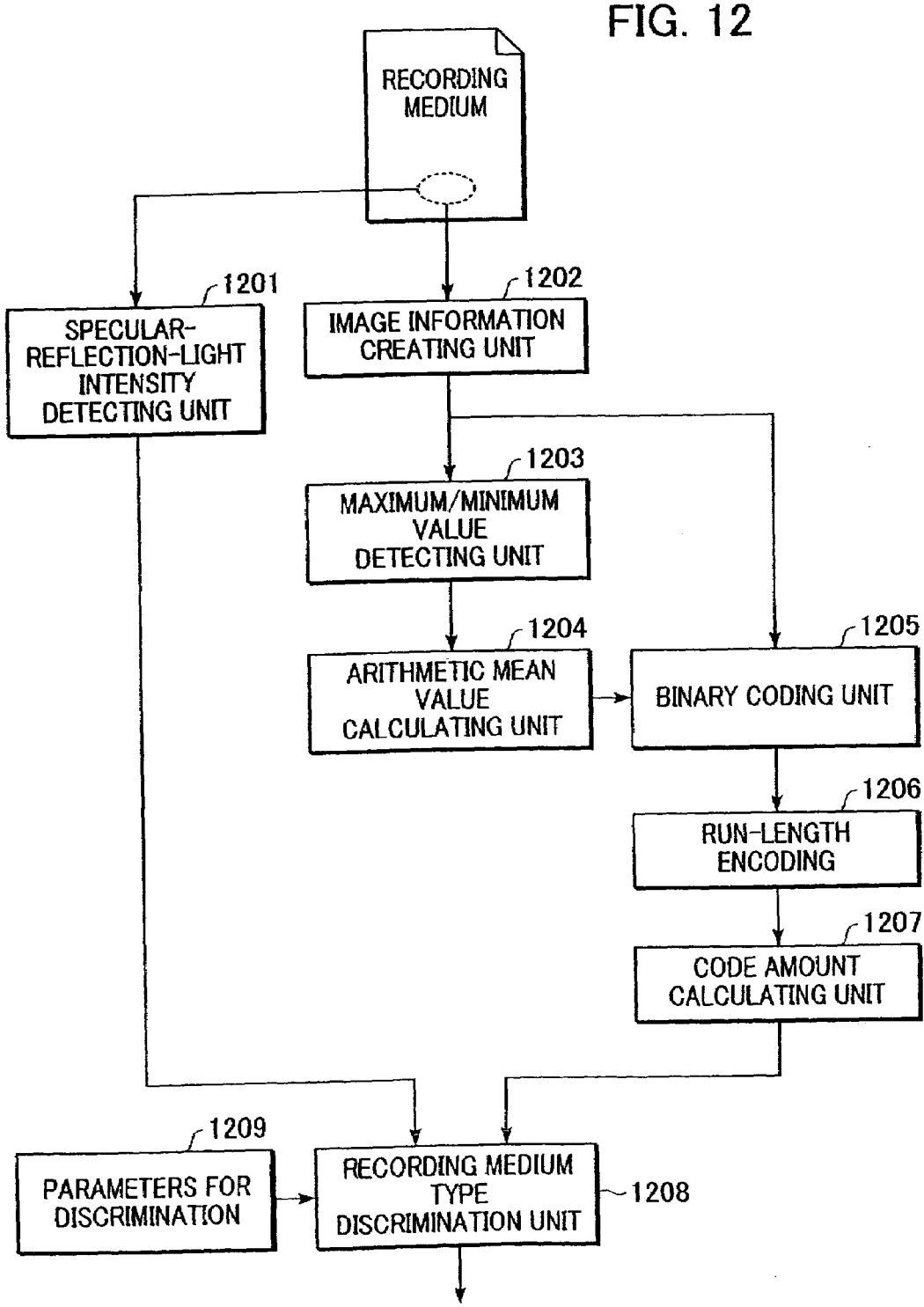
FIG. 12 is a functional block diagram showing a recording medium discrimination method according to a second embodiment of the present invention.

FIG. 12 is a functional block diagram showing the recording medium discriminating method according to the second embodiment.

A specular-reflection-light intensity detecting unit 1201 detects the intensity of one component of reflected lights from a surface of a recording medium, which is illuminated by a light source, i.e., the intensity of a specular reflection light having reflected at an angle of reflection equal to an angle of incidence is detected.

An image information creating unit 1202 creates image information from an arbitrary small area of the recording medium surface. A function of creating image information from a component of diffuse reflection light from the recording medium performed by the image information creating unit 1202, requirements for each pixel making up an image, etc. are similar to those of the first embodiment.

A maximum/minimum value detecting unit 1203 detects, from the image information made up of a plurality of pixels and obtained in the image information creating unit 1202, maximum and minimum values of brightness by referring to brightness values of the pixels. The pixels subjected to the detection of brightness values are all or a part of the pixels constituting the above-mentioned image of the small area used for the discrimination of the recording medium. An arithmetic mean value calculating unit 1204 calculates an arithmetic mean value of the maximum and minimum brightness values obtained in the maximum/minimum value detecting unit 1203 (i.e., a value resulting from adding the maximum and minimum values and dividing the sum by two).

A binary coding unit 1205 codes the image information obtained in the image information creating unit 1202 into binary values by employing, as a threshold, the arithmetic mean value obtained in the arithmetic mean value calculating unit 1204. A run-length encoding unit 1206 executes run-length encoding unit 1206 of a binary image (also called binary data) obtained in the binary coding unit 1205. Details of the run-length encoding unit 1206 will be described later with reference to FIG. 13. A code amount calculating unit 1207 calculates a code amount of the image, which has been encoded in the run-length encoding unit 1206. Details of the code amount calculating unit 1206 will be described later with reference to FIG. 13.

A recording medium type discrimination unit 1208 discriminates the type of the recording medium. The type of the recording medium is discriminated from both the intensity of the specular reflection light obtained in the specular-reflection-light intensity detecting unit 1201 and the run-length code amount obtained in the code amount calculating unit 1207. The discrimination of the type of the recording medium is performed using a table 1209 for discrimination, which is derived from a discrimination map prepared in advance and showing the relationships of various types of recording media versus the intensity of the specular reflection light and the run-length code amount. Details of a method for discriminating the type of the recording medium will be described below. Numeral 1209 denotes a table for discrimination, which is used in discriminating the type of the recording medium in the recording medium type discrimination unit 1208. In the table 1209 for discrimination, various types of recording media are related to the run-length code amount and the intensity of the specular reflection light.

Thus, the process flow comprises the steps of detecting the intensity of the specular reflection light from the recording medium, calculating the run-length code amount from the image information of the arbitrary small area of the recording medium surface, and then discriminating the type of the recording medium based on those results.

FIGS. 13A and 13B are representations for explaining run-length encoding executed in the run-length encoding unit 1206 and the code amount obtained in the code amount calculating unit 1207 shown in FIG. 12. It is assumed in FIGS. 13A and 13B that the image to be processed is given as information of a one-dimensional linear image.

FIG. 13A shows an example in which the run length is short. Numeral 1301 denotes a pixel at a certain position in an image after the binary coding. The pixel 1301 is a black pixel and has a value of 0. Also, numeral 1302 denotes a pixel at the 20-th position counted from the pixel 1301 at a certain position. The pixel 1302 is a white pixel and has a value of 1. FIG. 13B shows an example in which the run length is long. Numeral 1303 denotes a pixel at a certain position in an image after the binary coding. The pixel 1303 is a black pixel and has a value of 0. Also, numeral 1304 denotes a pixel at the 20-th position counted from the pixel 1303 at a certain position. The pixel 1303 is a black pixel and has a value of 0. In any of FIGS. 13A and 13B, the image after the binary coding is constituted by an array of white and black pixels. The white and black pixels are in fact pixels each having a value of 0 or 1.

The run-length encoding is now briefly described. The run-length encoding is an encoding scheme primarily used in facsimile machines, for example, in which, when the same data element frequently appears in continuation, attention is focused on a combination of that data element and the number of times which that data element appears. Codes are allocated such that a smaller code amount is allocated to a combination that frequently appears, and a larger code amount is allocated to a combination that rarely appears. As a result, a total code amount can be reduced. This second embodiment utilizes the fact that, by calculating the run-length code amount, a brightness difference and a period of changes in brightness among a plurality of pixels making up an image can be confirmed. In other words, features of surface roughness and surface shape of the recording medium can be obtained from the run-length code amount.

First, a description is made of FIG. 13A. In FIG. 13A, codes are allocated by using terminating codes for MH (Modified Huffman) coding that is used in facsimile machines. For example, when there is one black pixel alone, 3 bits of 010 are allocated. Likewise, when there is one white pixel alone, 6 bits of 000111 are allocated. Thus, by employing the encoding scheme in which a larger code amount is allocated to the image information in which the run length of pixels having the same value is short, i.e., the image information representing a shorter period of changes in the brightness value, a larger code amount than 21 pixels, which is the number of pixels to be processed, is allocated as shown in FIG. 13A. Generally, because 1 bit is required to indicate a state of each pixel in the binary image, 21 pixels can be expressed using 21 bits. However, when the run-length encoding is applied to data in which combinations of pixels of respective values continue with repetition of a shorter run length, as shown in FIG. 13A, a very large code amount of 45 bits is allocated.

Next, a description is made of FIG. 13B. In FIG. 13B, as with FIG. 13A, codes are allocated by using terminating codes for the MH (Modified Huffman) coding. For example, 0011 is allocated when five black pixels continue, 1111 is allocated when seven white pixels continue, and 000100 is allocated when nine black pixels continue. Thus, it is understood that, by allocating smaller code amounts to the image information representing a longer period of changes in the brightness value, the code amount representing 21 pixels shown in FIG. 13B is given by 14 bits, i.e., a value smaller than the number of pixels (21) to be processed.

Thus, by applying the run-length encoding to an array of pixels, it is possible to precisely and clearly confirm not only a tendency in respective numbers of white pixels and black pixels, but also an index representing continuation of pixels having the same value, the index being given by whether the run length is short or long.

While this embodiment employs the Huffman coding as one example of the run-length encoding, codes can be allocated with any other suitable specific coding to match with the number and tendency of pixels of the image to be processed. Also, what is here required is not a bit string after the coding, but an index representing the run length. Therefore, the intended function can be sufficiently realized merely by allocating the code amount, i.e., the number of bits, to a particular run length without allocating a terminating code to the particular run length.

In this embodiment of the present invention, two kinds of features of the recording medium surface are obtained as parameters, and the type of the recording medium is discriminated based on these parameters. By measuring the intensity of the specular reflection light described above, the feature regarding the magnitude of unevenness of the recording medium surface is obtained. Also, by calculating the run-length code amount corresponding to changes in brightness information in accordance with an array of successive pixels, the feature regarding the period of unevenness of the recording medium surface is obtained. Herein, the magnitude of unevenness of the recording medium surface is referred to as a "smoothness or gloss feature", and the period of unevenness of the recording medium surface is referred to as a "surface shape feature". A manner of discriminating the type of the recording medium based on those two features will be described below.

Figure 14:
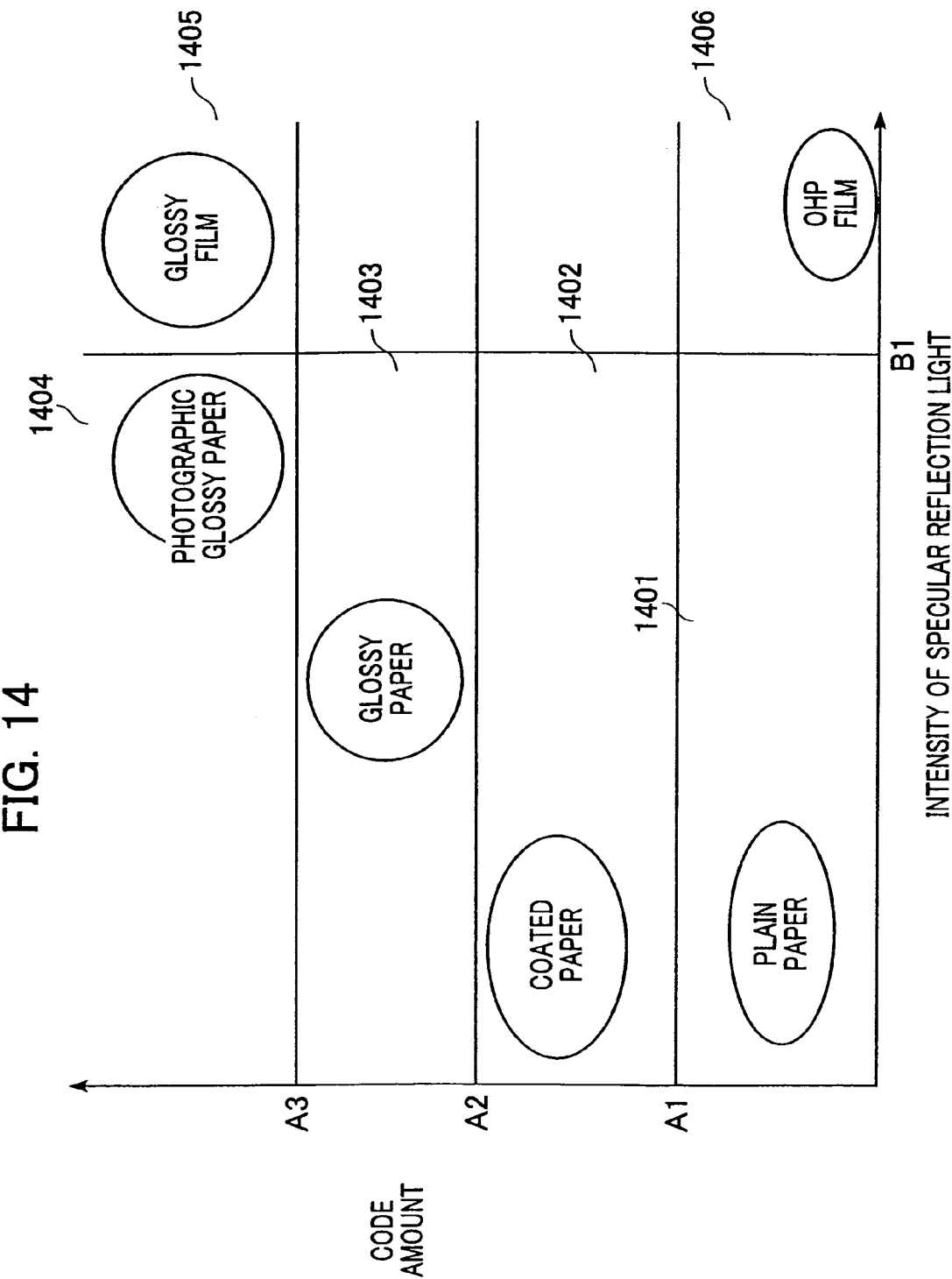
FIG. 14 is a discrimination map showing the relationships of various types of recording media versus a run-length code amount and the intensity of a specular reflection light in the second embodiment.

FIG. 14 is a discrimination map showing the relationships of various types of recording media versus the run-length code amount and the intensity of the specular reflection light. Circular regions in FIG. 14 each represent a set of points corresponding to the measured results, and discrimination areas are defined by dividing a map plane as shown based on the circular regions.

Numeral 1401 represents an area in which the recording medium under measurement is discriminated to be plain paper. Numeral 1402 represents an area in which it is discriminated to be ink-jet coated paper. Numeral 1403 represents an area in which it is discriminated to be glossy paper. Numeral 1404 represents an area in which it is discriminated to be photographic glossy paper. Numeral 1405 represents an area in which it is discriminated to be a glossy film. Numeral 1406 represents an area in which it is discriminated to be an OHP film.

The above-described relationships of the various types of recording media versus the run-length code amount and the intensity of the specular reflection light are summarized in Table 4 given below.

TABLE 4

| | Plain paper (a) | Coated paper (b) | Glossy paper (c) | Photographic glossy paper (d) | Glossy film (e) | OHP film (f) |
|---|---|---|---|---|---|---|
| Specular reflection light intensity | low | low | medium | high | higher than (d) | higher than (d) |
| Run-length code amount | small | medium | large | larger than (c) | larger than (c) | hardly appreciable |

As seen from Table 4, the run-length code amount shows a similar tendency to that of the number of reversals in the first embodiment.

Figure 15:
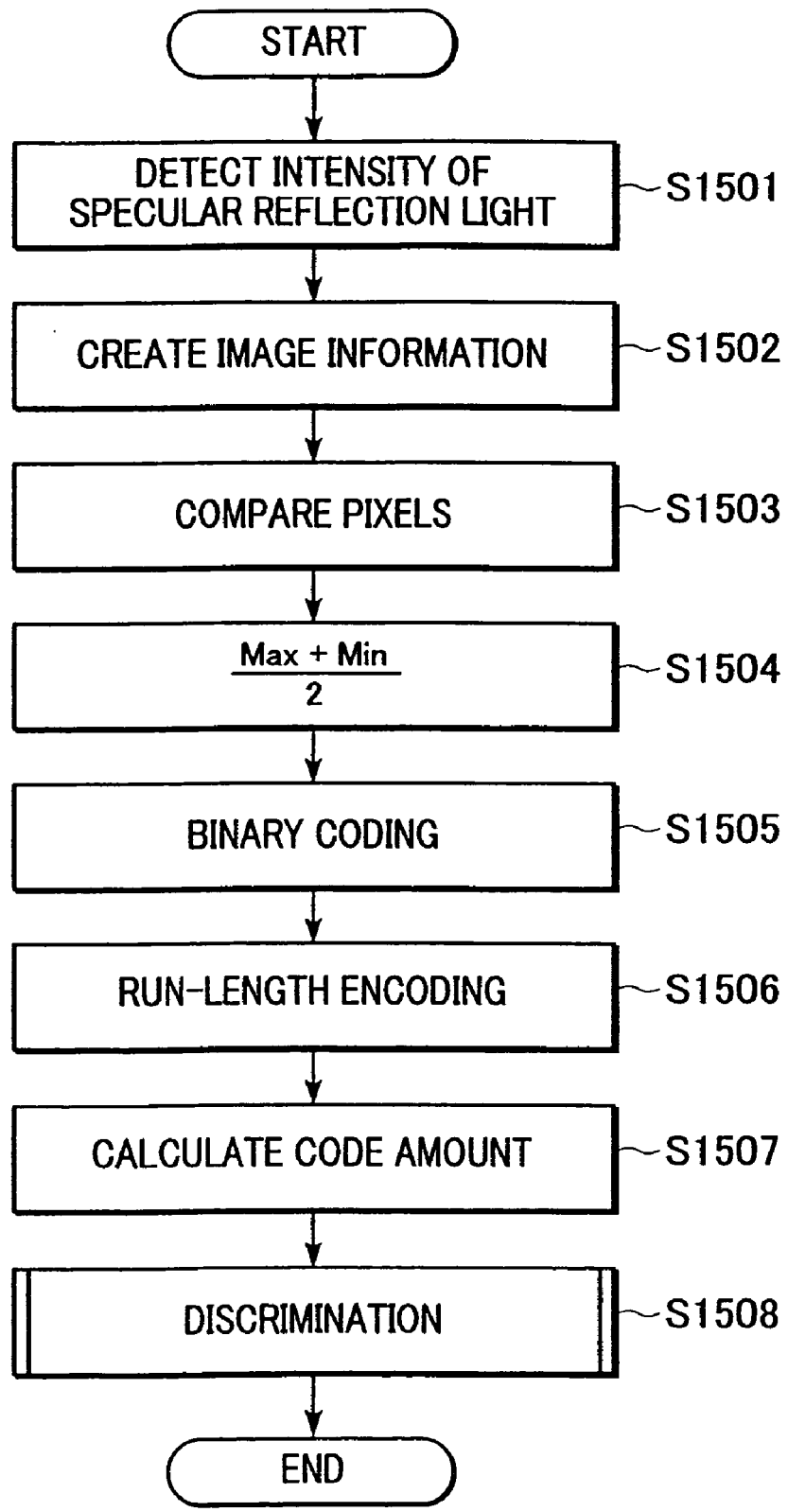
FIG. 15 is a flowchart showing a flow of a recording medium type discrimination process in the second embodiment.

FIG. 15 is a flowchart of a recording medium type discrimination process in this second embodiment.

In step 1501 (S1501), the intensity of the specular reflection light is detected. In step S1502, image information is created. In step S1503, pixels are compared with each other based on the image information obtained in step S1502. Specifically, maximum and minimum brightness values are detected. In step S1504, an arithmetic mean value of the maximum and minimum brightness values detected in step S1503 is calculated. In step S1505, binary coding is executed using, as a threshold, the arithmetic mean value calculated in step S1504. In step S1506, the run-length encoding is executed on an image obtained after the binary coding. In step S1507, the code amount resulting from the run-length encoding is calculated. In step S1508, the type of the recording medium is discriminated based on the intensity of the specular reflection light obtained in step S1501 and the run-length code amount obtained as a feature variable in step S1507.

In the flowchart of the recording medium type discrimination process shown in FIG. 15, the intensity of the specular reflection light is detected in step S1501, i.e., at the beginning of the process flow. However, it is only required that the intensity of the specular reflection light be detected before the type of the recording medium is discriminated in step S1508.

Figure 16:
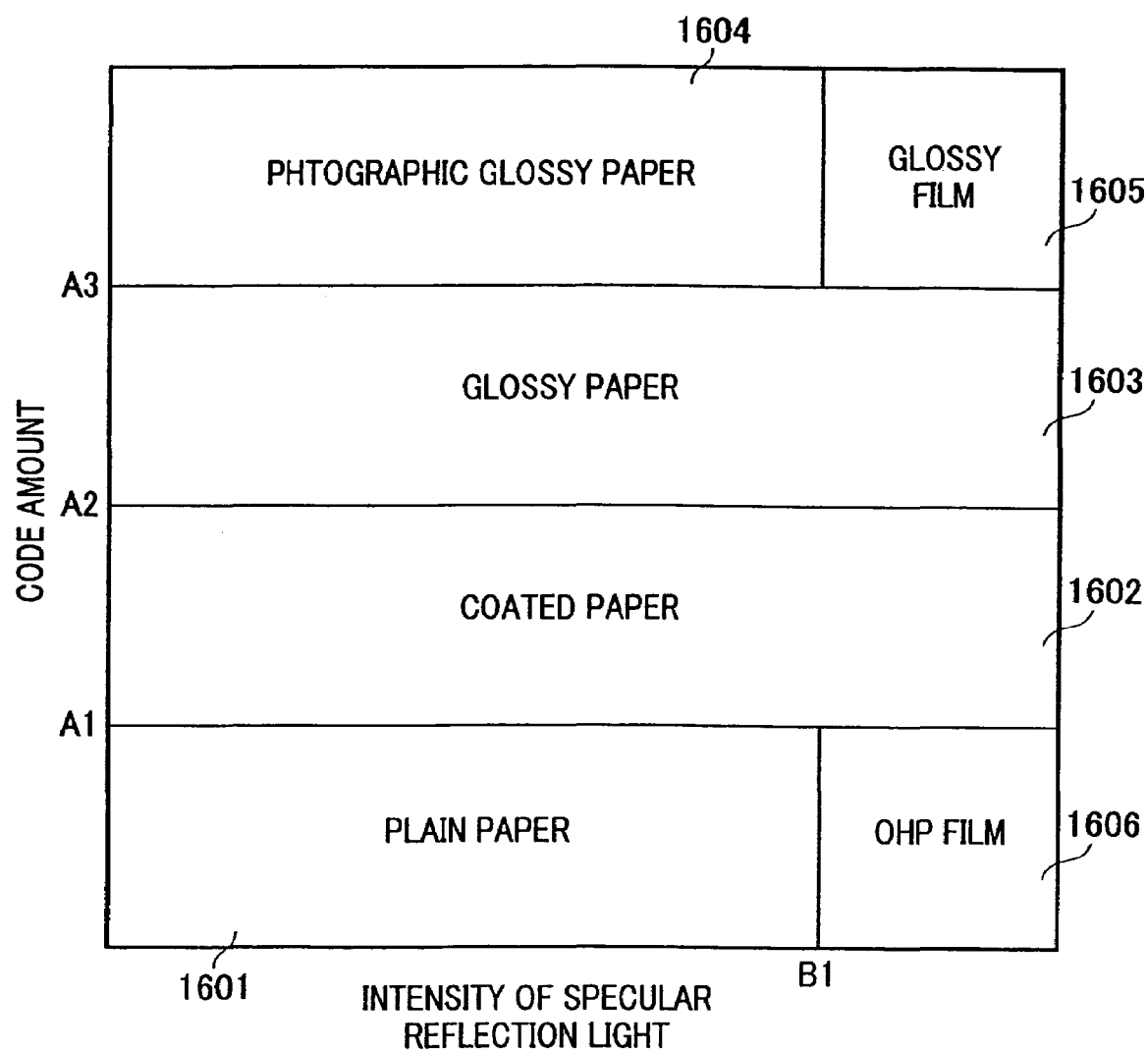
FIG. 16 is a recording medium type discrimination table in the second embodiment.

FIG. 16 is a discrimination table used for the type of the recording medium in step S1508 of FIG. 15. This discrimination table is prepared based on the discrimination map shown in FIG. 14.

Numeral 1601 represents an area in which the recording medium under measurement is discriminated to be plain paper. Numeral 1602 represents an area in which it is discriminated to be ink-jet coated paper. Numeral 1603 represents an area in which it is discriminated to be glossy paper. Numeral 1604 represents an area in which it is discriminated to be photographic glossy paper. Numeral 1605 represents an area in which it is discriminated to be a glossy film. Numeral 1606 represents an area in which it is discriminated to be an OHP film.

With this second embodiment, as with the first embodiment, features indicated by the intensity of the specular reflection light from the recording medium and representing surface conditions of the recording medium from an image of a predetermined area of the recording medium surface are obtained, and the type of the recording medium is discriminated based on the obtained features. By employing the run-length code amount when discriminating the type of the recording medium, the difference in the surface conditions of the recording medium can be made more noticeable, and the accuracy in discriminating the type of the recording medium can be improved. To that end, it is also possible to execute optimization so that codes are allocated based on a statistical process of an appearance pattern of the run length. With the optimization, the discrimination can be made using an index that enables the intention on the discriminating side, i.e., the intention of the user, to be more precisely reflected upon image features than the parameter obtained by totaling the number of recesses and projections in the uneven surface, e.g., the number of reversals used the first embodiment. Further, coarse and dense patterns in the pixel array can also be confirmed by paying attention to combinations of white and black run lengths.

Also, by employing the run-length code amount, an allowance error for the focal length of the image sensor can be increased. The reason is that, even if the distance between the image sensor and the recording medium is slightly changed and a blurred image results because of a focusing deviation, the effect of the focusing deviation can be alleviated because the run-length coding is applied to an image after the binary coding.

While this embodiment employs, as the threshold for use in the binary coding, the arithmetic mean value of the maximum and minimum brightness values, similar advantages can also be obtained using another parameter indicating the magnitude of unevenness of the recording medium surface, such as another kind of arithmetic mean value obtained from all the pixels, or the brightness value at a peak of the histogram.

While this embodiment employs the discrimination table 1209 in discriminating the type of the recording medium, similar advantages can also be obtained by employing a threshold based on distributions measured for the run-length code amount and the intensity of the specular reflection light of the various types of recording media.

(Third Embodiment)

A third embodiment implementing the present invention will be described below in detail with reference to the drawings.

A recording medium type discriminating method realizing this third embodiment is featured in discriminating the type of the recording medium based on the intensity of the specular reflection light and the number of isolated pixels. A process flow and a discrimination flow are substantially the same as those in the first embodiment, and hence a description thereof is omitted here.

Figure 17:
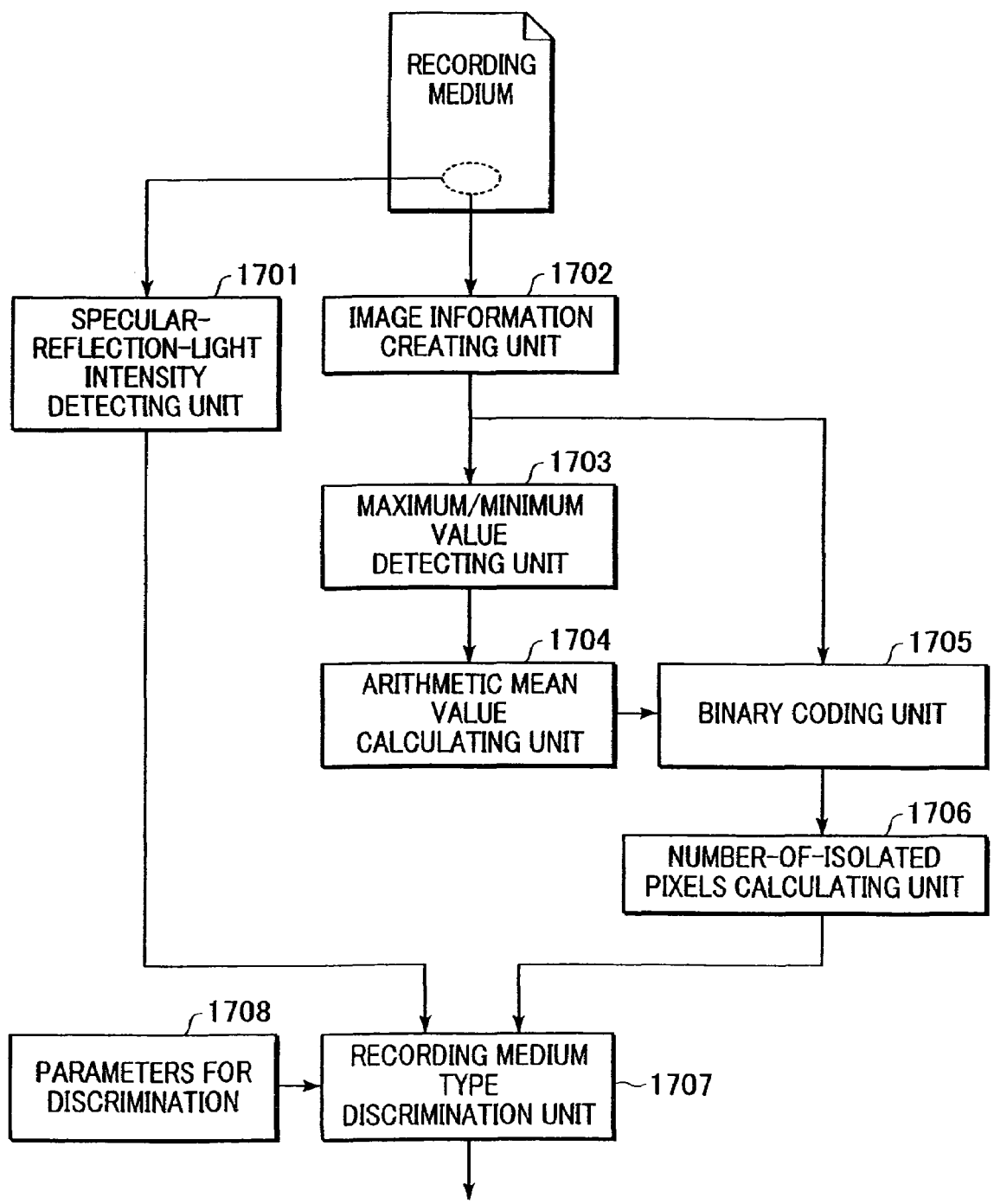
FIG. 17 is a functional block diagram of a recording medium discrimination method according to a third embodiment of the present invention.

FIG. 17 is a functional block diagram showing the recording medium discriminating method according to the third embodiment.

A specular-reflection-light intensity detecting unit 1701 detects the intensity of one component of reflected lights from a surface of a recording medium, which is illuminated by a light source, i.e., the intensity of a specular reflection light having reflected at an angle of reflection equal to an angle of incidence is detected.

An image information creating unit 1702 creates image information from an arbitrary small area of the recording medium surface. A function of creating the image information from a component of diffuse reflection light from the recording medium performed by the image information creating unit 1702, requirements for each pixel making up an image, etc. are similar to those of the first embodiment.

A maximum/minimum value detecting unit 1703 detects, from the image information made up of a plurality of pixels and obtained in the image information creating unit 1702, maximum and minimum values of brightness by referring to brightness values of the pixels. The pixels subjected to the detection of brightness values are all or a part of the pixels constituting the above-mentioned image of the small area used for the discrimination of the recording medium. An arithmetic mean value calculating unit 1704 calculates an arithmetic mean value of the maximum and minimum brightness values obtained in the maximum/minimum value detecting unit 1703 (i.e., a value resulting from adding the maximum and minimum values and dividing the sum by two).

A binary coding unit 1705 codes the image information obtained in the image information creating unit 1702 into binary values by employing, as a threshold, the arithmetic mean value obtained in the arithmetic mean value calculating unit 1704. A number-of-isolated pixels calculating unit 1706 calculates the number of isolated pixels, i.e., the number of pixels that are determined to be isolated pixels from values of adjacent pixels on both sides of the isolated pixel based on a binary image (also called binary data) obtained in the binary coding unit 1705. Details of the number-of-isolated pixels calculating unit 1706 will be described later with reference to FIG. 18.

A recording medium type discrimination unit 1707 discriminates the type of the recording medium. The type of the recording medium is discriminated from both the intensity of the specular reflection light obtained in the specularreflection-light intensity detecting unit 1701 and the number of isolated pixels obtained in the number-of-isolated pixel calculating unit 1706. The discrimination of the type of the recording medium is performed using parameters 1708 for discrimination, which are derived from a discrimination map prepared in advance and showing the relationships of various types of recording media versus the intensity of the specular reflection light and the number of isolated pixels. Numeral 1708 denotes parameters for discrimination, which are used in discriminating the type of the recording medium in the recording medium type discrimination unit 1707, i.e., thresholds decided based on distributions measured for the various types of recording media.

Thus, the process flow comprises the steps of detecting the intensity of the specular reflection light from the recording medium, calculating the number of isolated pixels from the image information of the arbitrary small area of the recording medium surface, and then discriminating the type of the recording medium based on those results.

Figure 18:
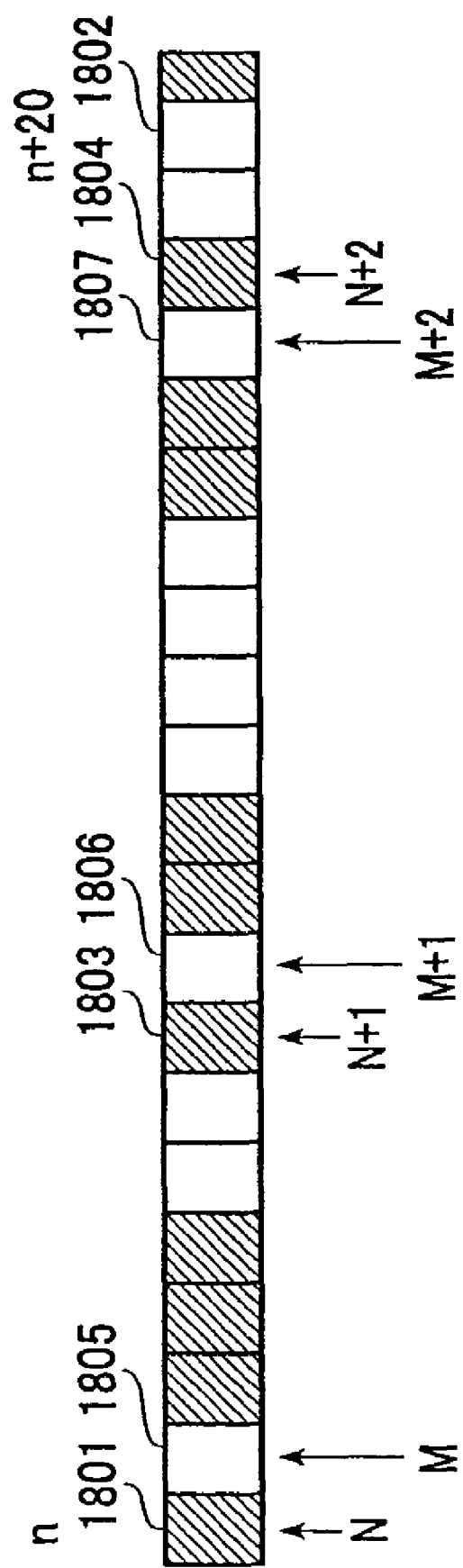
FIG. 18 is a representation for explaining the number of isolated pixels after binary coding in the third embodiment.

FIG. 18 is a representation for explaining the number of isolated black or white pixels after the binary coding executed in the number-of-isolated pixels calculating unit 1706 shown in FIG. 17. It is assumed in FIG. 18 that the image to be processed is given as information of a one-dimensional linear image.

Numeral 1801 denotes a pixel at a certain position in an image after the binary coding. The pixel 1801 is a black pixel and has a value of 0. Also, numeral 1802 denotes a pixel at the 20-th position counted from the pixel 1801 at a certain position. The pixel 1802 is a white pixel and has a value of 1. In the image shown in FIG. 18, there are some positions where the pixels on both sides of a certain black or white pixel are reversed to white or black pixels. A pixel at such a position is referred to as an isolated pixel. In this embodiment, the number of isolated pixels is employed as one of parameters for use in discriminating the type of the recording medium. The isolated black pixels, each having a value of 0, are a pixel 1803 at the seventh position and a pixel 1804 at the 18-th position counted from the pixel 1801. Also, taking a white pixel as a predetermined target pixel, the isolated white pixels are a pixel 1805 at the first position, a pixel 1806 at the eighth position, and a pixel 1807 at the 17-th position counted from the pixel 1801.

Assuming that the number of black isolated pixels before the pixel 1801 is N, since there are two black isolated pixels between the pixels 1801 and 1802, the number of black isolated pixels before the pixel 1802 is (N+2). Similarly, assuming that the number of white isolated pixels before the pixel 1805 is M, since there are two white isolated pixels between the pixels 1805 and 1802, the number of white isolated pixels before the pixel 1802 is (M+2).

The isolated pixels frequently appear in an area of the image in which brightness abruptly changes. Also, the isolated pixels noticeably appear in a recording medium having a higher smoothness and a smaller period of surface unevenness, such as glossy paper or a glossy film. In those recording media, therefore, the number of isolated pixels is increased. Conversely, in a recording medium having moderate changes in surface asperities, such as plain paper, pixels having the same value (e.g., black pixels) tend to continue, and hence the number of isolated pixels is reduced.

In this embodiment of the present invention, two kinds of features of the recording medium surface are obtained as parameters, and the type of the recording medium is discriminated based on the parameters. By measuring the intensity of the specular reflection light described above, the feature regarding the magnitude of unevenness of the recording medium surface is obtained. Also, by measuring the number of isolated pixels corresponding to changes in brightness information in accordance with an array of successive pixels, the feature regarding the period of unevenness of the recording medium surface is obtained. Herein, the magnitude of unevenness of the recording medium surface is referred to as a "smoothness or gloss feature", and the period of unevenness of the recording medium surface is referred to as a "surface shape feature". A manner of discriminating the type of the recording medium based on those two features will be described below.

Figure 19:
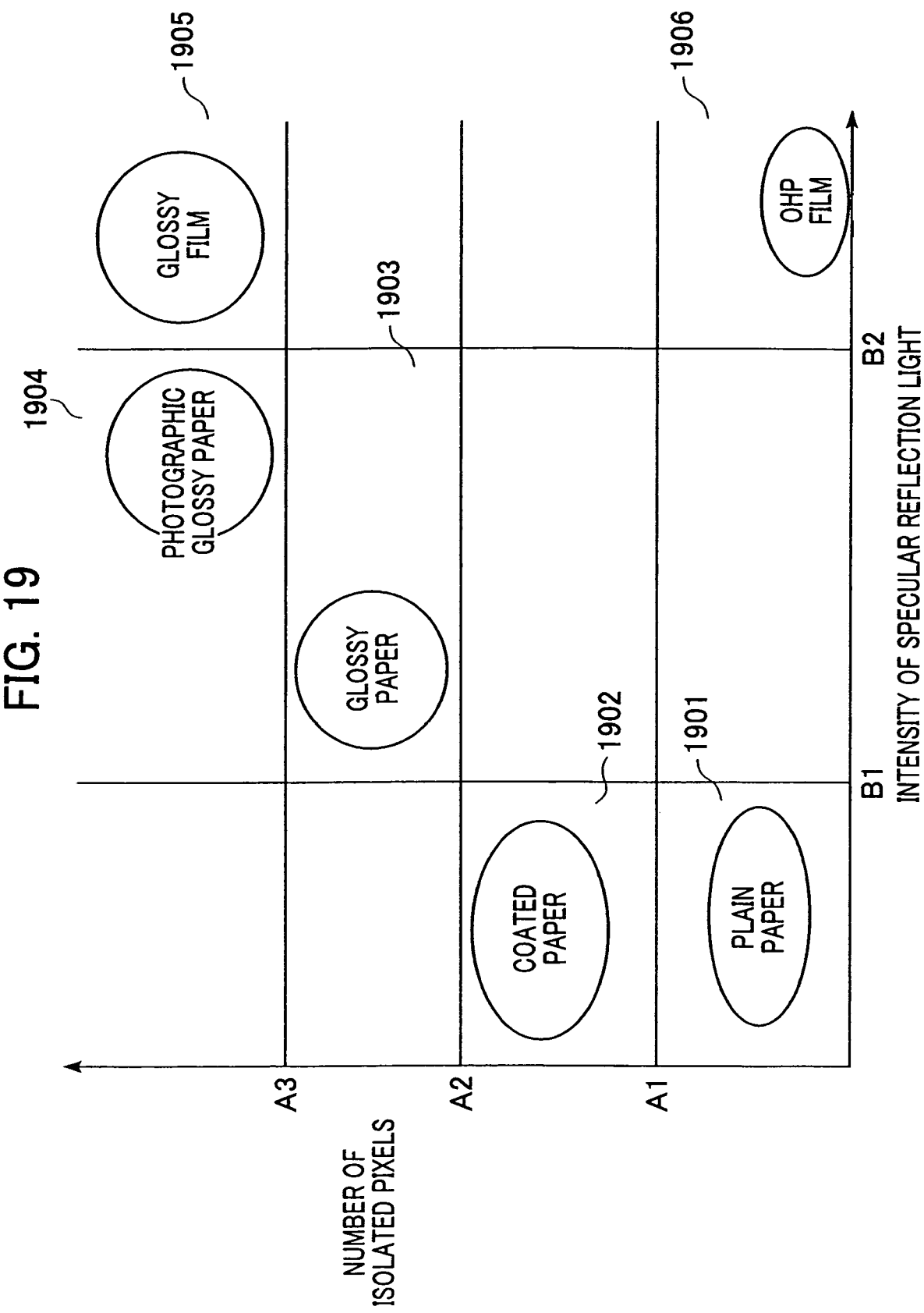
FIG. 19 is a discrimination map showing the relationships of various types of recording media versus the number of isolated pixels and the intensity of a specular reflection light in the third embodiment.

FIG. 19 is a discrimination map showing the relationships of various types of recording media versus the number of isolated pixels and the intensity of the specular reflection light.

Values denoted by A1 to A3, B1 and B2 in FIG. 19 are used as the parameters 1708 for discrimination shown in FIG. 17. Circular regions in FIG. 19 each represent a set of points corresponding to the measured results, and discrimination areas are defined by dividing a map plane as shown based on the circular regions.

Numeral 1901 represents an area in which the recording medium under measurement is discriminated to be plain paper. Numeral 1902 represents an area in which it is discriminated to be ink-jet coated paper. Numeral 1903 represents an area in which it is discriminated to be glossy paper. Numeral 1904 represents an area in which it is discriminated to be photographic glossy paper. Numeral 1905 represents an area in which it is discriminated to be a glossy film. Numeral 1906 represents an area in which it is discriminated to be an OHP film.

The above-described relationships of the various types of recording media versus the number of isolated pixels and the intensity of the specular reflection light are summarized in Table 5 given below.

TABLE 5

|  | Plain paper (a) | Coated paper (b) | Glossy paper (c) | Photographic glossy paper (d) | Glossy film (e) | OHP film (f) |
| --- | --- | --- | --- | --- | --- | --- |
| Specular reflection light intensity | low | low | medium | high | higher than (d) | higher than (d) |
| Number of isolated pixels | small | medium | large | larger than (c) | larger than (c) | hardly appreciable |

As seen from Table 5, the number of isolated pixels shows a similar tendency to the number of reversals in the first embodiment and the run-length code amount in the second embodiment.

With this third embodiment, as with the first and second embodiments, a parameter indicated by the intensity of the specular reflection light from the recording medium and a parameter representing surface conditions of the recording medium and derived from an image of a predetermined area of the recording medium surface are obtained, and the type of the recording medium is discriminated based on these obtained parameters. By employing the number of isolated pixels when discriminating the type of the recording medium, similar advantages can be realized with the process having a simpler system configuration and imposing a smaller load on the control system than the case of calculating the code amount with the run-length encoding in the second embodiment. Also, by employing the number of isolated pixels, similar advantages can be obtained with basically the same system configuration as that of the first embodiment in which the number of reversals of pixel values is calculated. In this regard, the number of discrimination parameters can be increased by one by paying attention to each of the white and black isolated pixels.

While this embodiment employs, as the threshold for use in the binary coding, the arithmetic mean value of the maximum and minimum brightness values, similar advantages can also be obtained using another parameter indicating the magnitude of unevenness of the recording medium surface, such as another kind of arithmetic mean value obtained from all the pixels, or the brightness value at a peak of the histogram.

While this embodiment employs the discrimination parameters 1708 in discriminating the type of the recording medium, similar advantages can also be obtained by employing a discrimination table in which the types of recording media are related to the number of isolated pixels and the intensity of the specular reflection light, as explained in the second embodiment.

(Fourth Embodiment)

A fourth embodiment implementing the present invention will be described below in detail with reference to the drawings.

A recording medium type discriminating method realizing this fourth embodiment is featured in discriminating the type of the recording medium based on the intensity of the specular reflection light and the number of reversals of positive and negative signs;of brightness values between adjacent pixels. The following description is made of primarily that latter feature of this fourth embodiment. A process flow and a discrimination flow are substantially the same as those in the first embodiment, and hence a description thereof is omitted here.

Figure 20:
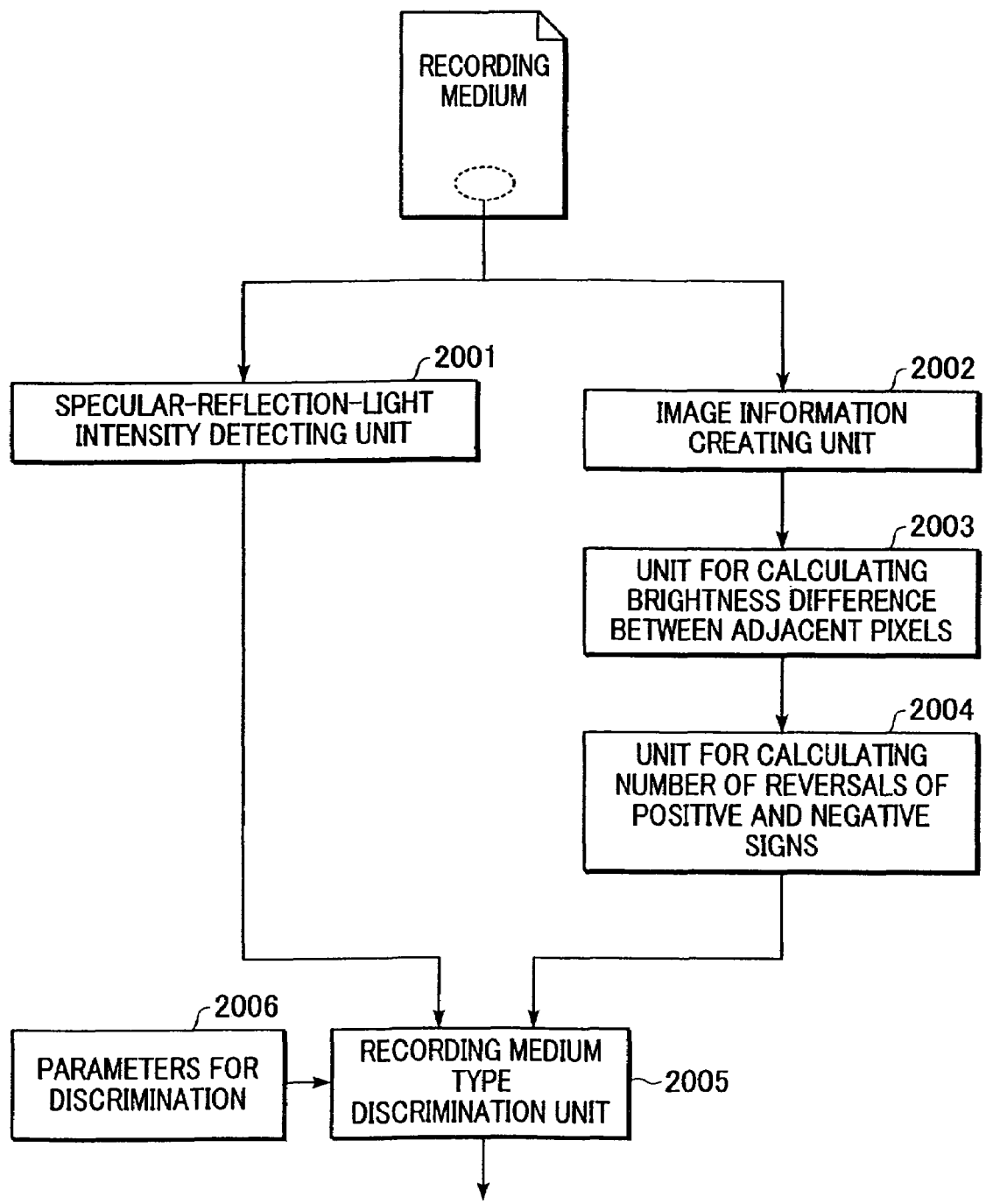
FIG. 20 is a functional block diagram showing a recording medium discrimination method according to a fourth embodiment of the present invention.

FIG. 20 is a functional block diagram showing the recording medium discriminating method according to the fourth embodiment.

A specular-reflection-light intensity detecting unit 2001 detects the intensity of one component of reflected lights from a surface of a recording medium which is illuminated by a light source, i.e., the intensity of a specular reflection light having reflected at an angle of reflection equal to an angle of incidence is detected.

An image information creating unit 2002 creates image information from an arbitrary small area of the recording medium surface. A function of creating the image information from a component of diffuse reflection light from the recording medium performed by the image information creating unit 2002, requirements for each pixel making up an image, etc. are similar to those of the first embodiment.

Numeral 2003 denotes a unit for calculating a brightness difference between adjacent pixels, which calculates the brightness difference between adjacent pixels from the image information obtained in the image information creating unit 2002. Details of the unit 2003 for calculating a brightness difference between adjacent pixels will be described later with reference to FIG. 21. Numeral 2004 denotes a unit for calculating the number of reversals of positive and negative signs, which finds signs of the brightness difference obtained in the unit 2003 for calculating a brightness difference between adjacent pixels and adds the number of times the sign is reversed from positive to negative or negative to positive. Details of the unit 2004 for calculating the number of reversals of positive and negative signs will also be described later with reference to FIG. 21.

A recording medium type discrimination unit 2005 discriminates the type of the recording medium. The type of the recording medium is discriminated from both the intensity of the specular reflection light obtained in the specular-reflection-light intensity detecting unit 2001 and the number of reversals of positive and negative signs obtained in the unit 2004 for calculating the number of reversals of positive and negative signs. The discrimination of the type of the recording medium is performed using parameters 2006 for discrimination, which are derived from a discrimination map prepared in advance and showing the relationships of various types of recording media versus the intensity of the specular reflection light and the number of reversals of positive and negative signs. Numeral 2006 denotes parameters for discrimination, which are used in discriminating the type of the recording medium in the recording medium type discriminating unit 2005, i.e., thresholds decided based on distributions measured for the various types of recording media.

Thus, the process flow comprises the steps of detecting the intensity of the specular reflection light from the recording medium, calculating the number of reversals of positive and negative signs from the image information of the arbitrary small area of the recording medium surface, and then discriminating the type of the recording medium based on those results.

Figure 21:
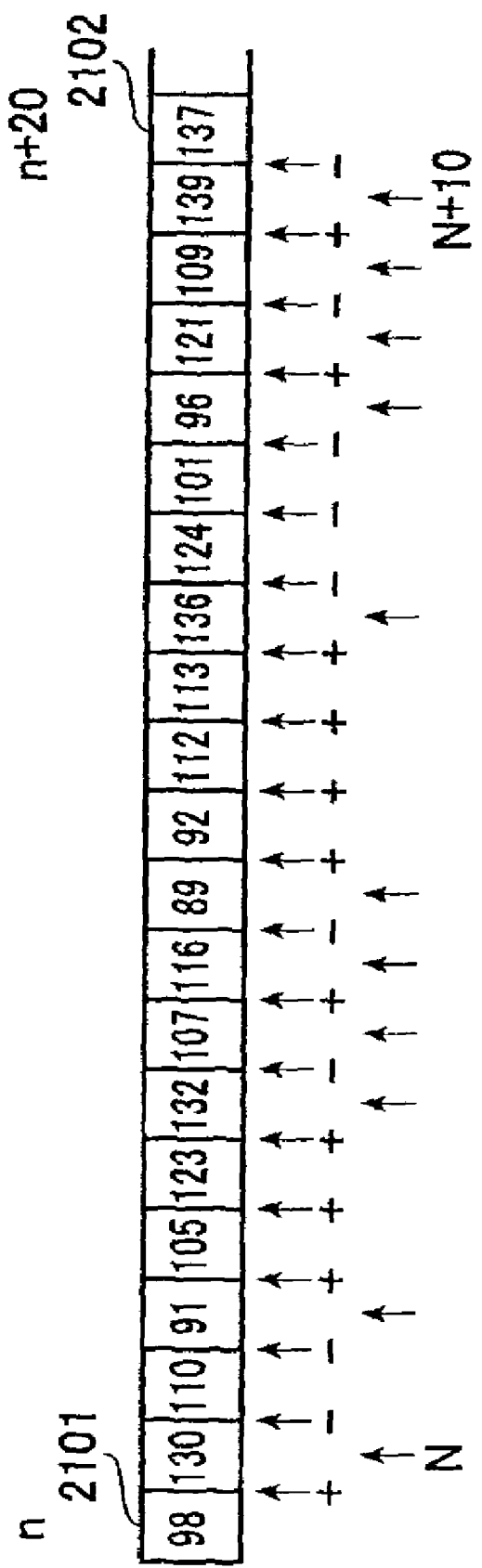
FIG. 21 is a representation for explaining the number of times positive and negative signs of a brightness difference between adjacent pixels reverse in the fourth embodiment.

FIG. 21 is a representation for explaining the number of reversals of positive and negative signs of the brightness difference between adjacent pixels, which is calculated in a combination of the unit 2003 for calculating a brightness difference between adjacent pixels and the unit 2004 for calculating the number of reversals of positive and negative signs, both shown in FIG. 20. It is assumed in FIG. 21 that the image to be processed is given as information of a one-dimensional linear image. Also, it is assumed that each pixel has an 8-bit brightness data.

Numeral 2101 denotes a pixel at a certain position in an image and has a brightness value of 98. Also, numeral 2102 denotes a pixel at the 20-th position counted from the pixel 2101 at a certain position and has a brightness value of 137.

The unit 2003 for calculating a brightness difference between adjacent pixels, shown in FIG. 20, calculates the brightness difference between a relevant pixel and an adjacent pixel on the right side as viewed in FIG. 20. Assuming that an m-th pixel has a brightness value of $Y_m$ and an adjacent (m+1)-th pixel has a brightness value of $Y_{m+1}$, the brightness difference between adjacent pixels is given by $Y_{m+1}-Y_m$. For example, the brightness difference between the pixel 2101 at a position of m=n and an adjacent pixel (having a brightness value of 130) on the right side as viewed in FIG. 20 is given by 130−98=+32. Likewise, the brightness differences between subsequent adjacent pixels are calculated as −20, −19, +13, and so on. Looking at signs of the brightness differences thus obtained, the signs of the brightness differences between the pixel 2101 and the adjacent pixel, between a next pair of adjacent pixels, and so on are positive, negative, negative, positive, and so on. Then, the unit 2004 for calculating the number of reversals of positive and negative signs, shown in FIG. 20, calculates the number of reversals of positive and negative signs, i.e., the number of times the sign is changed from positive to negative and the number of times the sign is changed from negative to positive.

In FIG. 21, each arrow in an upper stage indicates a boundary position between adjacent pixels for which the brightness difference is calculated, and a symbol (+ or −) under the arrow represents a sign of the brightness difference, and each arrow in a lower stage indicates a point at which the sign is changed from positive to negative or from negative to positive.

Assuming that the number of reversals of positive and negative signs before the pixel 2101 is (N−1), since the sign is reversed eleven (11) times, which corresponds to the number of arrows in the lower stage between the pixels 2101 and 2102, the number of reversals of positive and negative signs can be obtained by adding the number of those arrows. In the illustrated case, the number of reversals of positive and negative signs before the pixel 2102 is (N+10).

In this fourth embodiment, on condition that each pixel has a multi-value data, the number of reversals of positive and negative signs is used as a parameter for discriminating the type of the recording medium. When the multi-value data is converted into binary data, the binary data shows a similar tendency to that of the number of reversals of pixel values after the binary coding in the first embodiment. Stated another way, calculating the number of reversals of positive and negative signs can be said to be one of methods for extracting from the image information the index indicating changes in asperities, which represent one of the features of the surface shape of the recording medium. By executing the above-described process while holding the multi-value data greater than a one-bit value, it is possible to confirm a tendency of even relatively small changes in the surface shape of the recording medium, which cannot be regarded as reversals of the pixel value after the binary coding.

In this embodiment of the present invention, two kinds of features of the recording medium surface are obtained as parameters, and the type of the recording medium is discriminated based on the parameters. By measuring the intensity of the specular reflection light described above, the feature regarding the magnitude of unevenness of the recording medium surface is obtained. Also, by measuring the number of reversals of positive and negative signs corresponding to changes in brightness information in accordance with an array of successive pixels, the feature regarding the period of unevenness of the recording medium surface is obtained. Herein, the magnitude of unevenness of the recording medium surface is referred to as a "smoothness or gloss feature", and the period of unevenness of the recording medium surface is referred to as a "surface shape feature". A manner of discriminating the type of the recording medium based on those two features will be described below.

Figure 22:
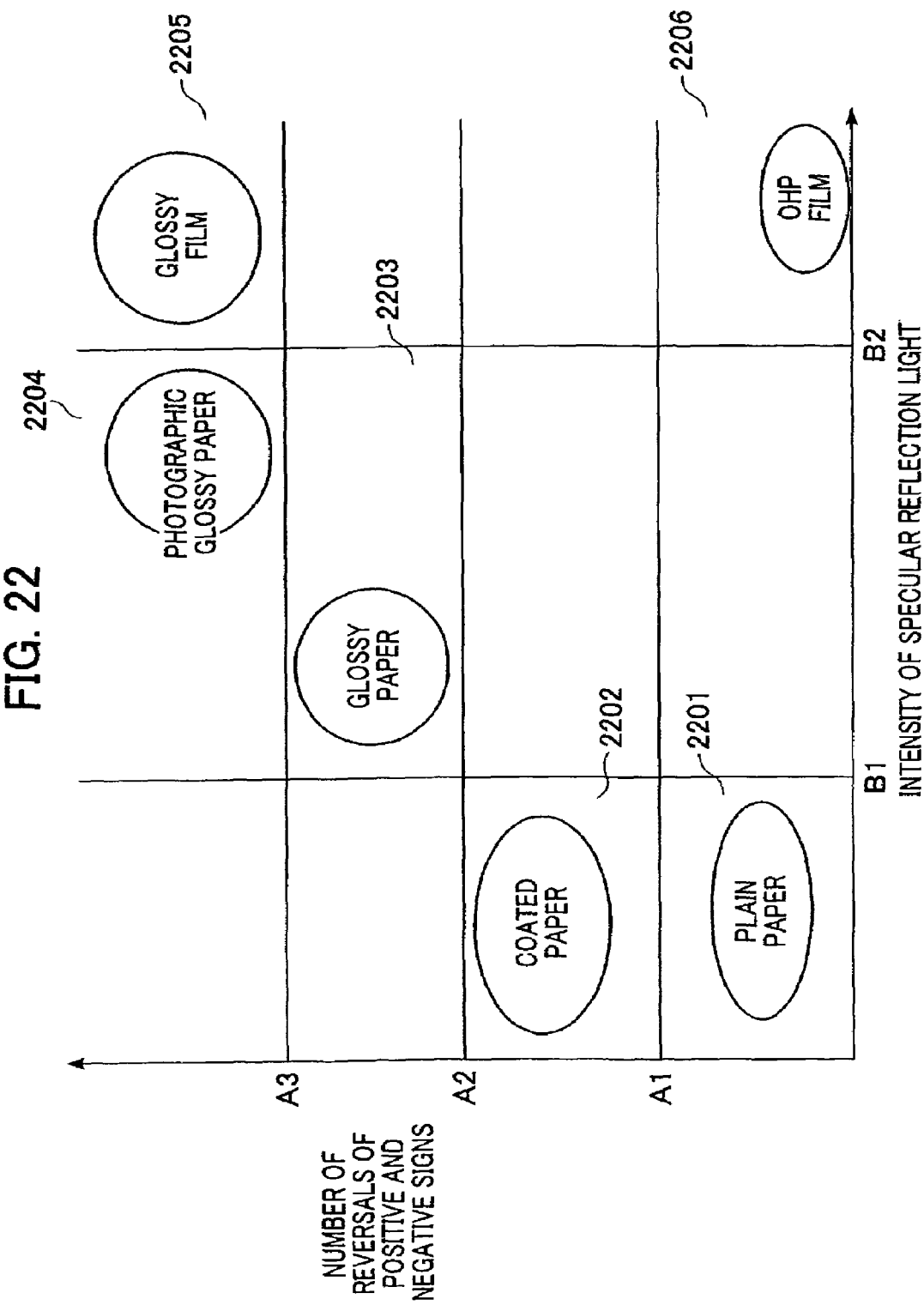
FIG. 22 is a discrimination map showing the relationships of various types of recording media versus the number of reversals of positive and negative signs and the intensity of a specular reflection light in the fourth embodiment.

FIG. 22 is a discrimination map showing the relationships of various types of recording media versus the number of reversals of positive and negative signs and the intensity of the specular reflection light. Values denoted by A1 to A3, B1 and B2 in FIG. 22 are used as the parameters 2006 for discrimination shown in FIG. 20. Circular regions in FIG. 22 each represent a set of points corresponding to the measured results, and discrimination areas are defined by dividing a map plane as shown based on the circular regions.

Numeral 2201 represents an area in which the recording medium under measurement is discriminated to be plain paper. Numeral 2202 represents an area in which it is discriminated to be ink-jet coated paper. Numeral 2203 represents an area in which it is discriminated to be glossy paper. Numeral 2204 represents an area in which it is discriminated to be photographic glossy paper. Numeral 2205 represents an area in which it is discriminated to be a glossy film. Numeral 2206 represents an area in which it is discriminated to be an OHP film.

The above-described relationships of the various types of recording media versus the number of reversals of positive and negative signs and the intensity of the specular reflection light are summarized in Table 6 given below.

TABLE 6

|  | Plain paper (a) | Coated paper (b) | Glossy paper (c) | Photographic glossy paper (d) | Glossy film (e) | OHP film (f) |
|---|---|---|---|---|---|---|
| Specular reflection light intensity | low | low | medium | high | higher than (d) | higher than (d) |
| number of reversals of (+) and (−) signs | small | medium | large | larger than (c) | larger than (c) | hardly appreciable |

As seen from Table 6, the number of reversals of positive and negative signs shows a similar tendency to those of the number of reversals after the binary coding in the first embodiment, the run-length code amount in the second embodiment, and the number of isolated pixels in the third embodiment.

With this fourth embodiment, as with the first, second and third embodiments, a feature indicated by the intensity of the specular reflection light from the recording medium and a feature representing surface conditions of the recording medium and derived from an image of a predetermined area of the recording medium surface are obtained, and the type of the recording medium is discriminated based on the obtained features. By employing the number of reversals of positive and negative signs when discriminating the type of the recording medium, it is possible to employ, as an index for discrimination, smaller changes in brightness than those in the case of using the parameters extracted after the binary coding, such as the number of reversals, as is done in the first to third embodiments.

While this embodiment employs the discrimination parameters 2006 in discriminating the type of the recording medium, similar advantages can also be obtained by employing a discrimination table in which the types of recording media are related to the number of reversals of positive and negative signs and the intensity of the specular reflection light as explained in the second embodiment.

While in this embodiment the number of reversals of positive and negative signs is given as the sum of the number of times the sign is reversed from positive to negative and the number of times the sign is reversed from negative to positive, similar advantages can also be obtained by employing only the number of times the sign is reversed from positive to negative or only the number of times the sign is reversed from negative to positive.

Further, in this embodiment, the brightness difference between adjacent pixels is calculated and a sign is assigned depending on the calculated brightness difference. However, variations and errors caused in the step of creating the image information can be absorbed by additionally executing a process in which a threshold is employed when assigning a sign depending on the brightness difference, i.e., a process for adjusting sensitivity.

(Fifth Embodiment)

A fifth embodiment implementing the present invention will be described below in detail with reference to the drawings.

A recording medium type discriminating method of this fifth embodiment is featured in discriminating the type of the recording medium based on the intensity of the specular reflection light and the number of pixels at a histogram peak. The following description is made of primarily that latter feature of this fifth embodiment.

Figure 23:
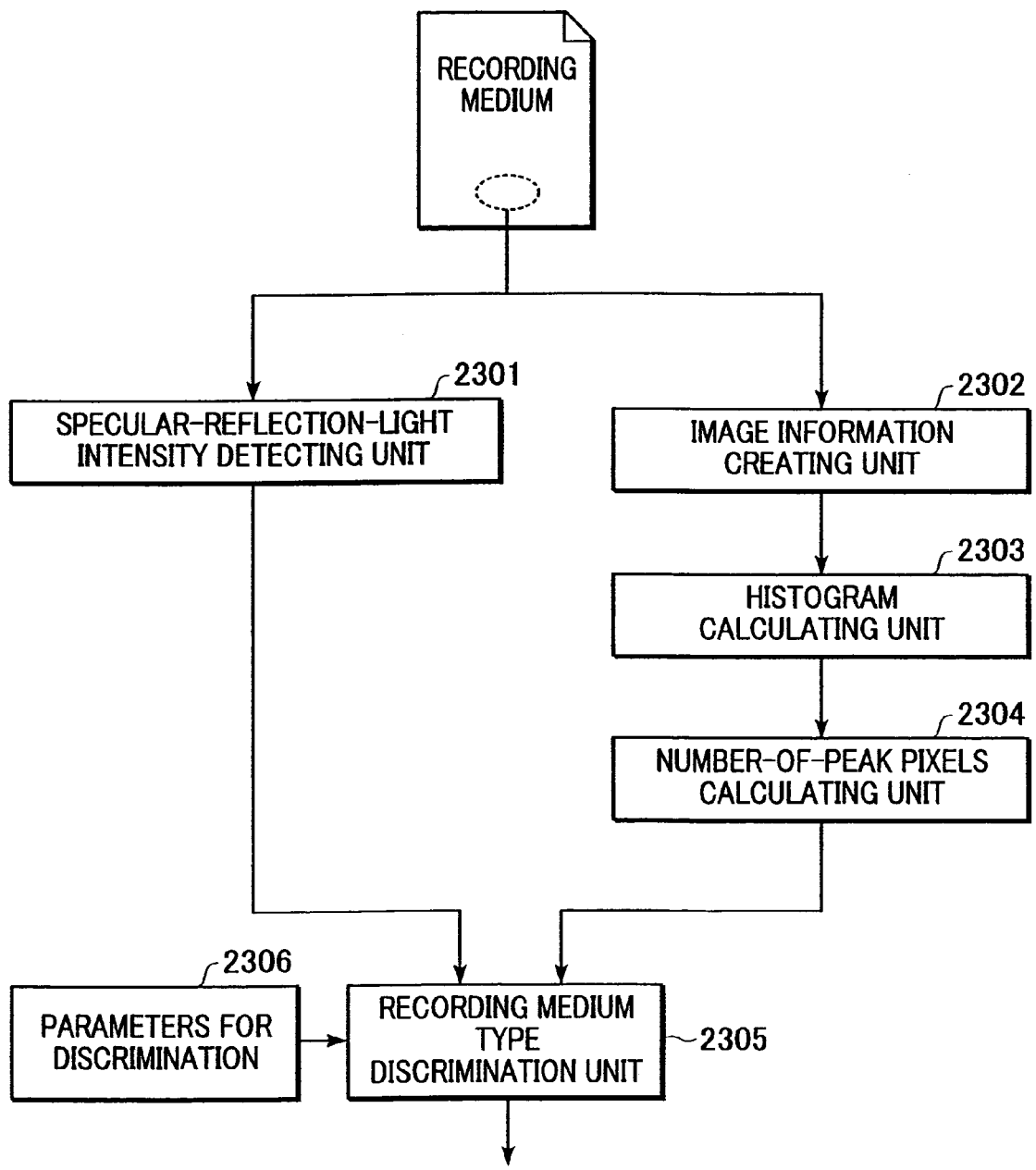
FIG. 23 is a functional block diagram of a recording medium discrimination method according to a fifth embodiment of the present invention.

FIG. 23 is a functional block diagram showing the recording medium discriminating method according to the fifth embodiment.

A specular-reflection-light intensity detecting unit 2301 detects the intensity of one component of reflected lights from a surface of a recording medium which is illuminated by a light source, i.e., the intensity of a specular reflection light having reflected at an angle of reflection equal to an angle of incidence is detected.

An image information creating unit 2302 creates image information from an arbitrary small area of the recording medium surface. A function of creating the image information from a component of diffuse reflection light from the recording medium performed by image information creating unit 2302, requirements for each pixel making up an image, etc. are similar to those of the first embodiment.

A histogram calculating unit 2303 calculates a histogram from the image information made up of a plurality of pixels and obtained in the image information creating unit 2302. Details of the histogram calculating unit 2303 will be described later with reference to FIG. 24. A number-of-peak (value) pixels calculating unit 2304 detects a brightness value at a peak of the histogram obtained in the histogram calculating unit 2303, and then calculates the number of pixels at the peak. Details of the number-of-peak pixels calculating unit 2304 will also be described later with reference to FIG. 24.

A recording medium type discrimination unit 2305 discriminates the type of the recording medium. The type of the recording medium is discriminated from both the intensity of the specular reflection light obtained in the specular-reflection-light intensity detecting unit 2301 and the number of peak pixels obtained in the number-of-peak pixels calculating unit 2304. The discrimination of the type of the recording medium is performed using parameters 2306 for discrimination, which are derived in advance and show the relationships of various types of recording media versus the intensity of the specular reflection light and the number of peak pixels. Numeral 2306 denotes parameters for discrimination, which are used in discriminating the type of the recording medium in the recording medium type discrimination unit 2305, i.e., thresholds decided based on distributions measured for the various types of recording media are used to discriminate the type of recording medium.

Thus, the process flow comprises the steps of detecting the intensity of the specular reflection light from the recording medium, calculating the number of peak pixels from the image information of the arbitrary small area of the recording medium surface, and then discriminating the type of the recording medium based on those results.

Figure 24:
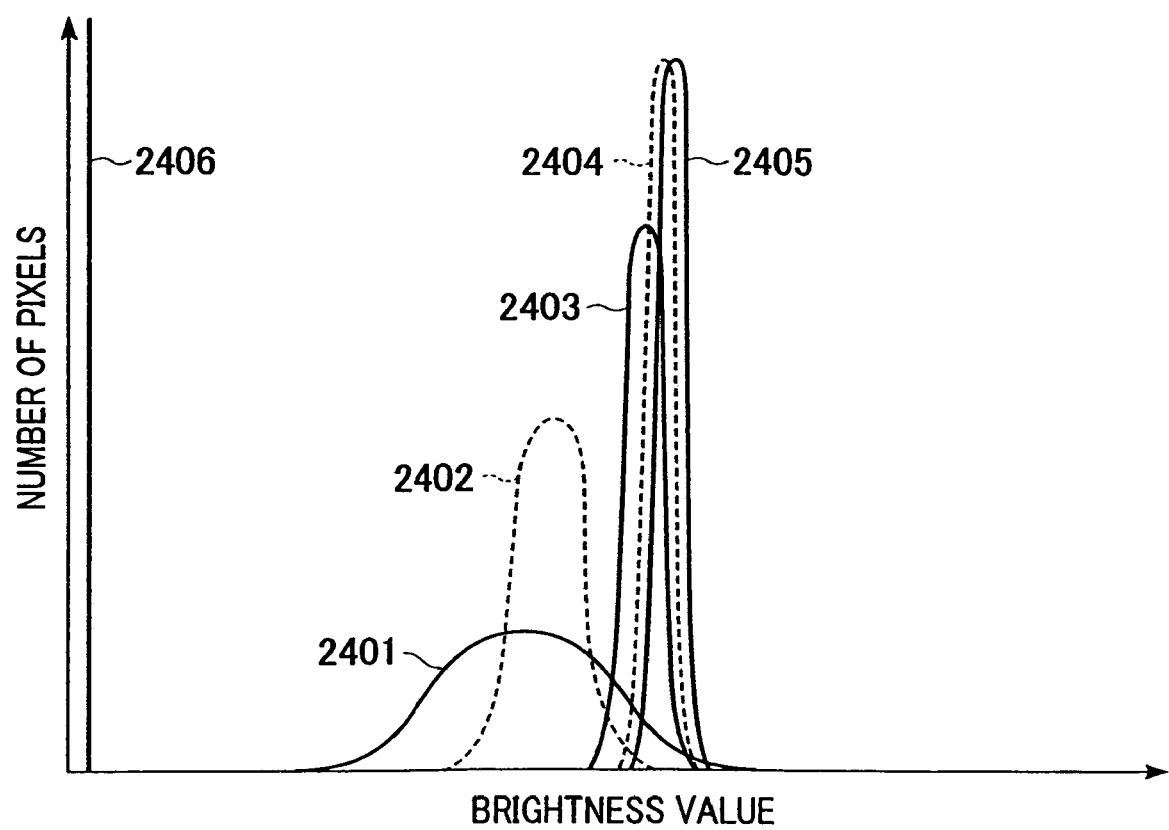
FIG. 24 shows histograms representing various types of recording media in the fifth embodiment.

FIG. 24 shows histograms of the various types of recording media. The horizontal axis represents brightness and the vertical axis represents the number of pixels having each value of the brightness. Each of the histograms shown in FIG. 24 is prepared by accumulating the number of pixels having a predetermined value of brightness in the histogram calculating unit 2303 based on the image information obtained in the image information creating unit 2302.

Numeral 2401 represents a histogram for plain paper. Numeral 2402 represents a histogram for ink-jet coated paper. Numeral 2403 represents a histogram for glossy paper. Numeral 2404 represents a histogram for photographic paper. Numeral 2405 represents a histogram for a glossy film. Numeral 2406 represents a histogram for an OHP film.

In this embodiment of the present invention, two kinds of features of the recording medium surface are obtained as parameters, and the type of the recording medium is discriminated based on these parameters. By measuring the intensity of the specular reflection light and the number of peak pixels resulting from a statistical process as described above, the features regarding the magnitude of unevenness of the recording medium surface are obtained. Herein, the magnitude of unevenness of the recording medium surface obtained from the intensity of the specular reflection light is referred to as a "smoothness or gloss feature", and the magnitude of unevenness of the recording medium surface obtained from the number of peak pixels is referred to as a "surface roughness feature". A manner of discriminating the type of the recording medium based on these two features will be described below.

A description is now briefly made of relationships between features of the six types of recording media to be detected in this embodiment and histograms.

Plain paper has a large magnitude of unevenness, which appears as a density difference in the image information, and therefore the histogram 2401 has broad distribution as shown. As a result, the plain paper provides a smaller number of peak pixels than the other types of recording media. Also, the peak brightness value of plain paper tends to have a relatively small value. The reason is that the peak brightness value shows substantially the same tendency as the degree of whiteness of the recording medium.

Ink-jet coated paper has a smaller magnitude of unevenness than plain paper, and therefore the histogram has a narrower distribution width than plain paper. Correspondingly, the ink-jet coated paper shows a larger number of peak pixels than plain paper. Also, the peak brightness value of ink-jet coated paper is substantially the same as that of plain paper in many cases.

Glossy paper has a narrower histogram distribution width and a larger number of peak pixels than ink-jet coated paper. Also, the peak brightness value of glossy paper is larger than those of plain paper and ink-jet coated paper.

Photographic glossy paper and a glossy film show substantially the same tendency as glossy paper, but they have an even narrower histogram distribution width and an even larger number of peak pixels. It is difficult to discriminate photographic glossy paper and glossy film based on their histograms.

Since an OHP film is formed so as to have substantially the same brightness value over its entire surface, the histogram distribution width is extremely narrow and it has the greatest number of peak pixels of the recording media to be detected. Most of a light illuminated from a light source passes through the recording medium, and hence the OHP film tends to show a minimum peak brightness value.

Figure 25:
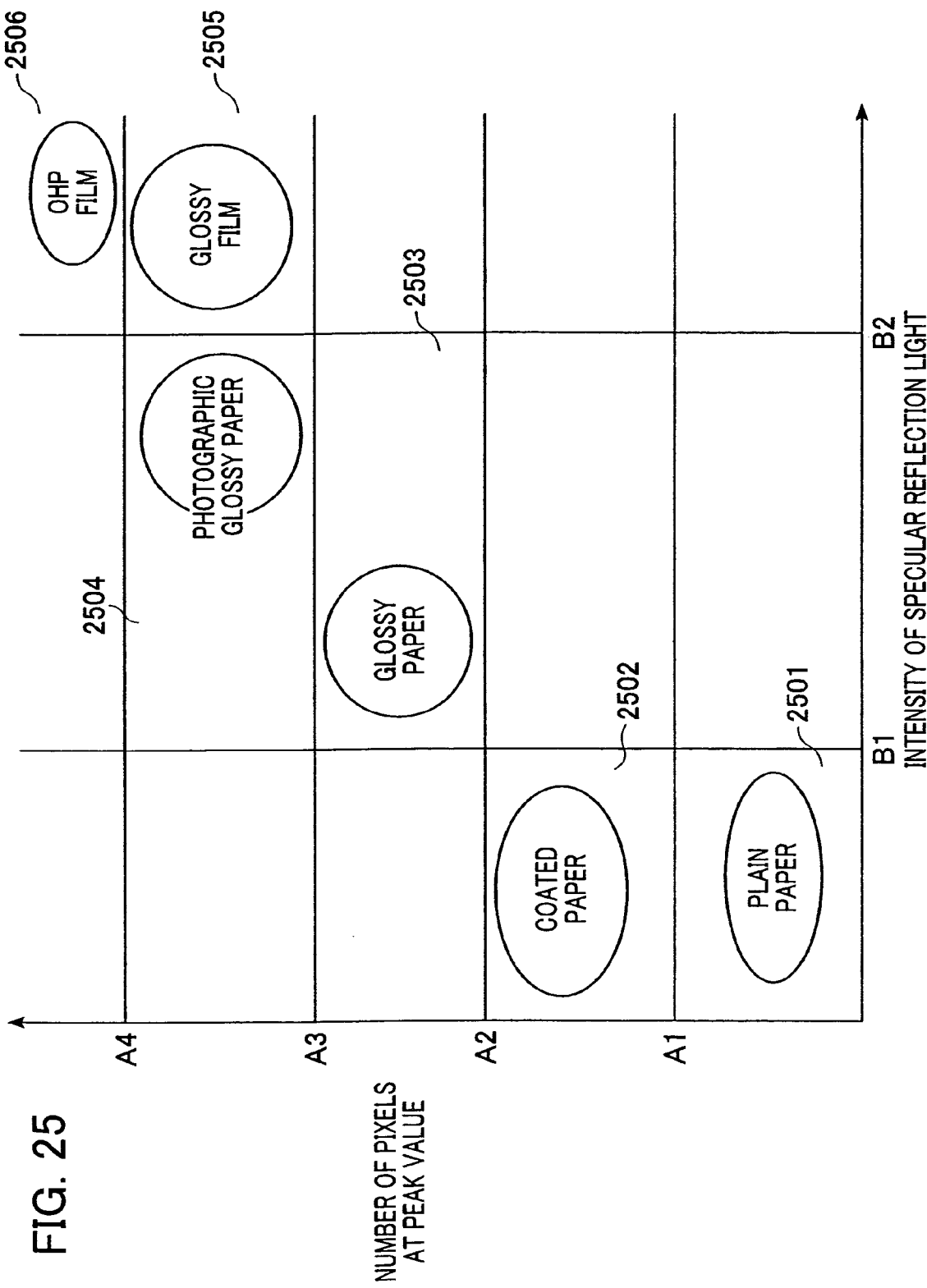
FIG. 25 is a discrimination map showing the relationships of various types of recording media versus the number of peak pixels and the intensity of a specular reflection light in the fifth embodiment.

FIG. 25 is a discrimination map showing the relationships of various types of recording media versus the number of peak pixels and the intensity of the specular reflection light. Circular regions in FIG. 25 each represent a set of points corresponding to the measured results, and discrimination areas are defined by dividing a map plane as shown based on the circular regions.

Numeral 2501 represents an area in which the recording medium under measurement is discriminated to be plain paper. Numeral 2502 represents an area in which it is discriminated to be ink-jet coated paper. Numeral 2503 represents an area in which it is discriminated to be glossy paper. Numeral 2504 represents an area in which it is discriminated to be photographic glossy paper. Numeral 2505 represents an area in which it is discriminated to be a glossy film. Numeral 2506 represents an area in which it is discriminated to be an OHP film.

The above-described relationships of the various types of recording media versus the number of peak pixels and the intensity of the specular reflection light are summarized in Table 7 given below.

TABLE 7

|  | Plain paper (a) | Coated paper (b) | Glossy paper (c) | Photo-graphic glossy paper (d) | Glossy film (e) | OHP film (f) |
|---|---|---|---|---|---|---|
| Specular reflection light intensity | low | low | medium | high | higher than (d) | higher than (d) |
| Number of peak pixels | small | medium | large | larger than (c) | larger than (c) | larger than (d), (e) |

Figure 26:
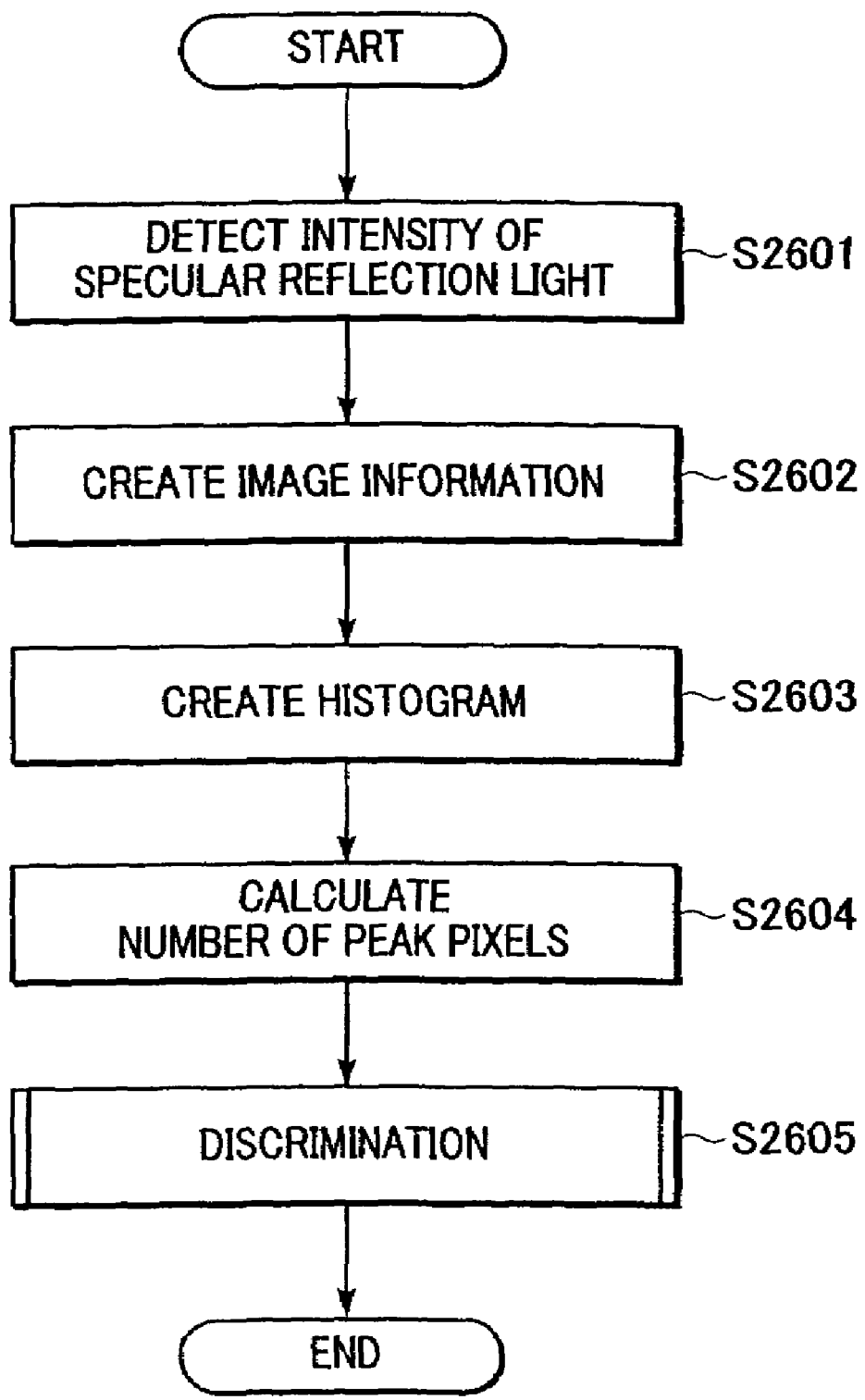
FIG. 26 is a flowchart showing a flow of a recording medium type discrimination process in the fifth embodiment.

FIG. 26 is a flowchart showing a flow of a recording medium type discriminating process in this fifth embodiment.

In step 2601 (S2601), the intensity of the specular reflection light is detected. In step S2602, image information is created. In step S2603, a histogram is created from the image information obtained in step S2602. In step S2604, a brightness value at a peak of the histogram created in step S2603 is detected, and the number of pixels at the peak is calculated. In step S2605, the type of the recording medium is discriminated based on the intensity of the specular reflection light obtained in step S2601 and the number of peak pixels obtained as a feature variable in step S2604.

In the flowchart of the recording medium type discriminating process shown in FIG. 26, the intensity of the specular reflection light is detected in step S2601, i.e., at the beginning of the process flow. However, it is only required that the intensity of the specular reflection light be detected before the type of the recording medium is discriminated in step S2605.

Figure 27:
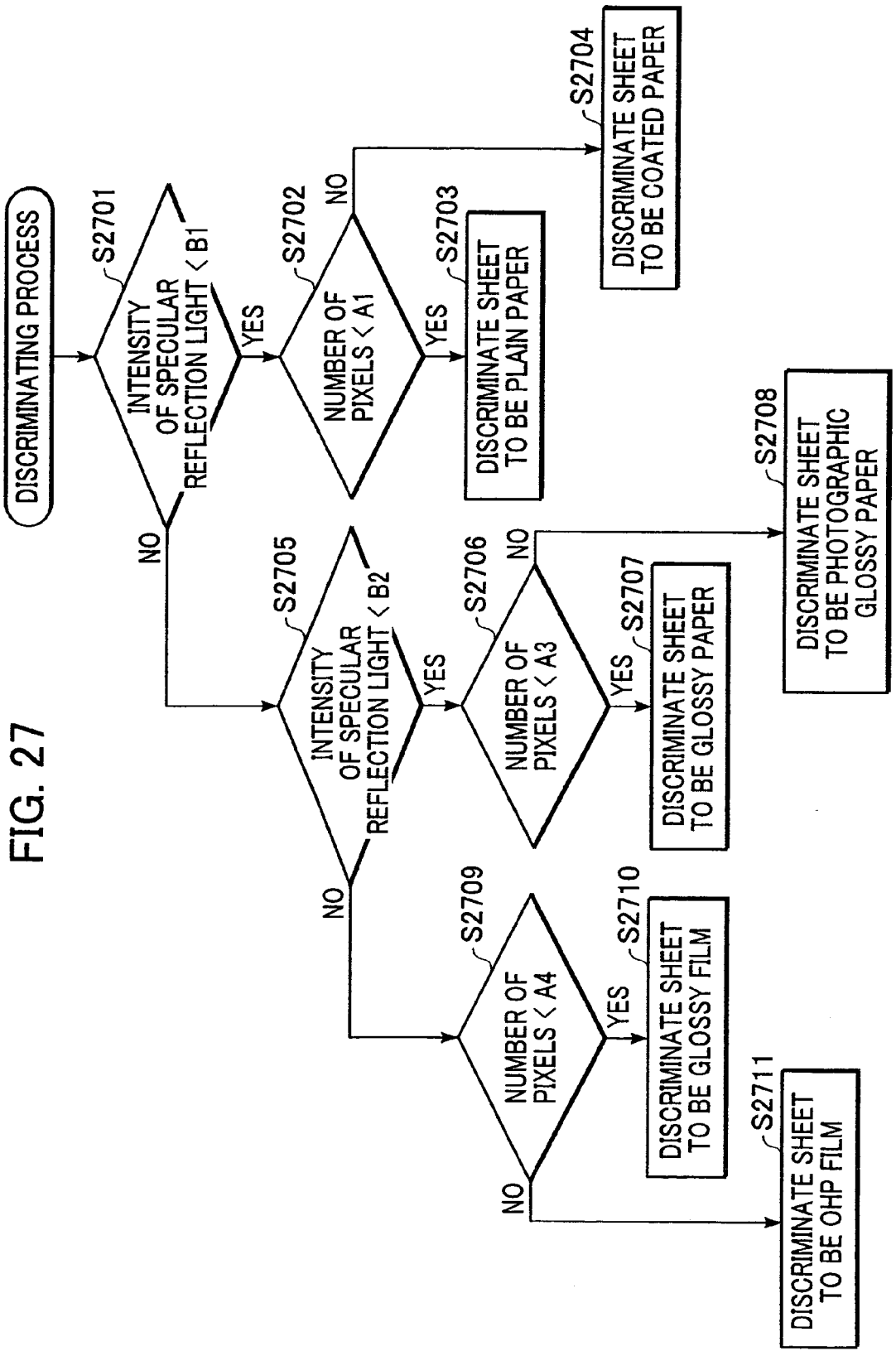
FIG. 27 is a flowchart showing a process flow for discrimination of the type of the recording medium in the fifth embodiment.

FIG. 27 is a flowchart showing a process flow for discrimination of the type of the recording medium in step S2605 shown in FIG. 26.

Based on the discrimination map shown in FIG. 25, the type of the recording medium is discriminated using the two obtained parameters as follows. For the following discussion, assume that the values A1, A2, A3, A4, B1 and B2 satisfy relationships given below. B1 and B2 are values representing the intensity of the specular reflection light and satisfy a relationship of B1<B2. Also, A1, A2, A3 and A4 are values representing the number of peak pixels and satisfy a relationship of A1<A2<A3<A4.

In step 2701 (S2701), it is determined whether the intensity of the specular reflection light is smaller than B1. If the intensity of the specular reflection light is smaller than B1, the process flow advances to step S2702, and if not, the process flow advances to step S2705.

In step S2702, it is determined whether the number of peak pixels is smaller than A1. If the number of peak pixels is smaller than A1, the process flow advances to step S2703, and if not, the process flow advances to step S2704.

In step S2703, the type of the recording medium is discriminated to be plain paper. In step S2704, the type of the recording medium is discriminated to be ink-jet coated paper.

In step S2705, it is determined whether the intensity of the specular reflection light is smaller than B2. If the intensity of the specular reflection light is smaller than B2, the process flow advances to step S2706, and if not, the process flow advances to step S2709.

In step S2706, it is determined whether the number of peak pixels is smaller than A3. If the number of peak pixels is smaller than A3, the process flow advances to step S2707, and if not, the process flow advances to step S2708.

In step S2707, the type of the recording medium is discriminated to be glossy paper. In step S2708, the type of the recording medium is discriminated to be photographic glossy paper.

In step S2709, it is determined whether the number of peak pixels is smaller than A4. If the number of peak pixels is smaller than A4, the process flow advances to step S2710, and if not, the process flow advances to step S2711.

In step S2710, the type of the recording medium is discriminated to be a glossy film. In step S2711, the type of the recording medium is discriminated to be an OHP film.

In the flowchart shown in FIG. 27, there are two processing steps to be executed until the type of the recording medium is discriminated to be plain paper. In a recording apparatus in which plain paper is used at high frequency, however, the process flow may be modified so as to promptly make the discrimination as to whether the type of the recording medium is plain paper. In such a situation, whether the type of the recording medium is plain paper can be discriminated first of all by paying attention only to the number of peak pixels and discriminating whether the number of peak pixels is smaller than A1 before discriminating in step S2701 whether the intensity of the specular reflection light is smaller than B1. In that case, the type of the recording medium can also be discriminated based on the discrimination map shown in FIG. 25 in a similar manner.

For the areas that are not allocated in FIG. 25 as areas used for discriminating the recording medium as a particular type of recording medium, e.g., for the areas in which the intensity of the specular reflection light is not smaller than B1 and the number of peak pixels is smaller than A2, the flowchart of FIG. 27 is designed so as to discriminate the type of the recording medium to be glossy paper or a glossy film. However, the flowchart may be modified such that for those areas, the absence of any corresponding type of recording medium is discriminated and the process for discriminating the type of the recording medium is executed again. As an alternative, error processing to return an error signal indicating the absence of any corresponding type of recording medium may be executed, and an error screen for notifying the user of the absence of any corresponding type of recording medium may be displayed.

With this fifth embodiment, as with the first, second, third and fourth embodiments, a parameter indicated by the intensity of the specular reflection light from the recording medium and a parameter representing surface conditions of the recording medium and derived from an image of a predetermined area of the recording medium surface are obtained, and the type of the recording medium is discriminated based on these obtained parameters. By using the number of pixels at a histogram peak when discriminating the type of the recording medium, similar advantages to those obtained in the case of employing the other parameters may be achieved. Also, the number of parameters used for the discrimination can be increased by additionally employing the other parameters obtained in connection with the creation of histograms such as a distribution width (equivalent to a brightness value) and a brightness value at the histogram peak. As a result, the discrimination can be realized with higher accuracy.

While in this embodiment the number of peak pixels is calculated as the total number of peak pixels having the brightness value at the histogram peak, a total number of pixels in a near-peak area, i.e., the number of pixels having the brightness values around the histogram peak may be calculated. This modification is effective in suppressing a variation in the measurement. As an alternative, it is also possible to measure a tendency of another feature and to use that feature as a parameter for the discrimination.

While this embodiment employs the discrimination parameters 2306 in discriminating the type of the recording medium, similar advantages can also be obtained by employing a discrimination table in which the types of recording media are related to the number of peak pixels and the intensity of the specular reflection light, as explained in the second embodiment.

(Sixth Embodiment)

A sixth embodiment implementing the present invention will be described below in detail with reference to the drawings.

sixth embodiment of a recording medium type discriminating method for discriminating the type of the recording medium discriminates based on the intensity of the specular reflection light and a brightness value given as a difference between maximum and minimum values of brightness of a plurality of pixels making up an image. The following description is made of primarily the latter feature of this sixth embodiment. A process flow and a discrimination flow are substantially the same as those of the first embodiment, and hence a description thereof is omitted here.

Figure 28:
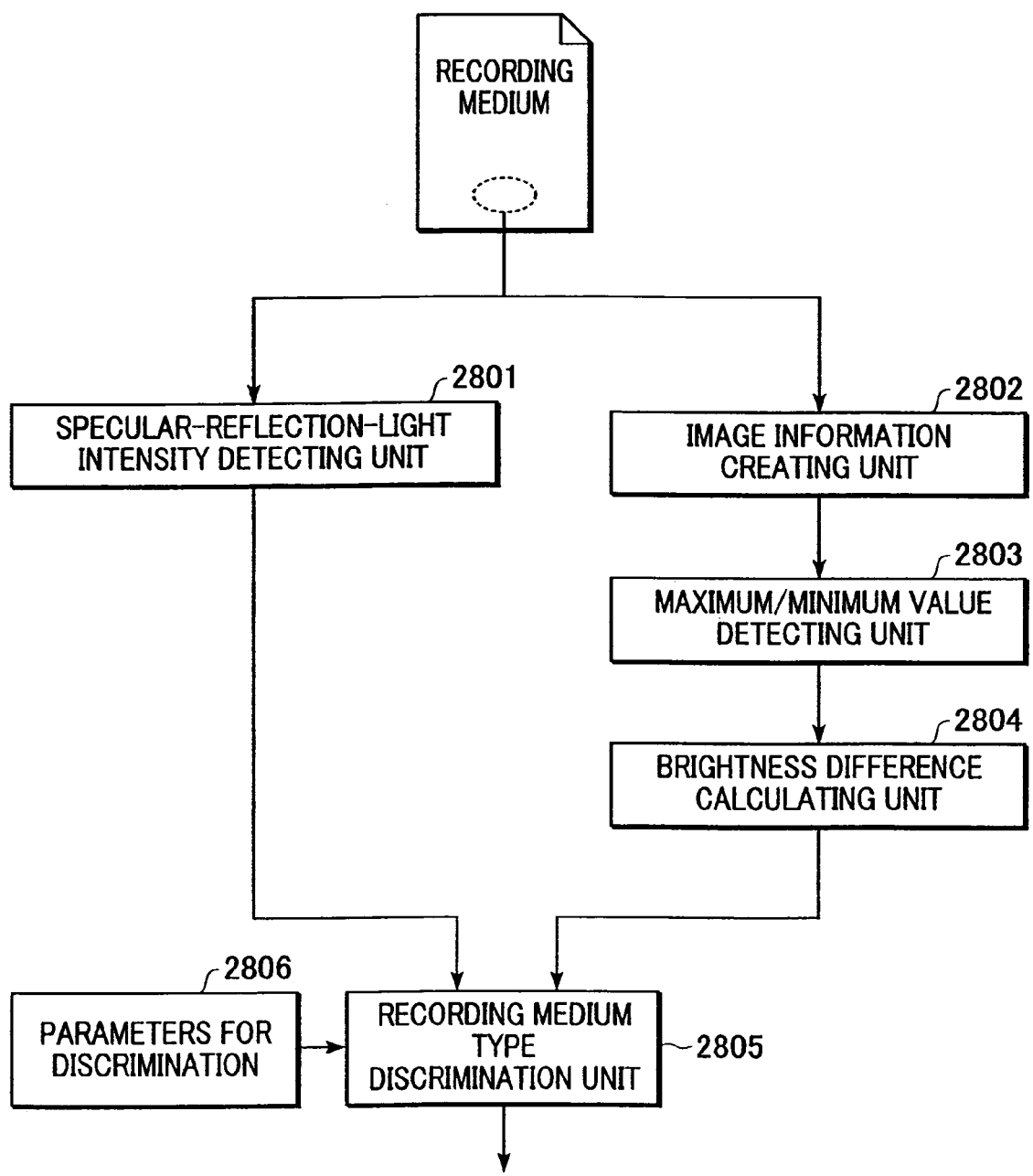
FIG. 28 is a functional block diagram of a recording medium discrimination method according to a sixth embodiment of the present invention.

FIG. 28 is a functional block diagram showing the recording medium discriminating method according to the sixth embodiment.

A specular-reflection-light intensity detecting unit 2801 detects the intensity of one component of reflected lights from a surface of a recording medium, which is illuminated by a light source, i.e., the intensity of a specular reflection light having reflected at an angle of reflection equal to an angle of incidence is detected.

An image information creating unit 2802 creates image information from an arbitrary small area of the recording medium surface. A function of creating the image information from a component of diffuse reflection light from the recording medium performed by the image information creating unit 2802, requirements for each pixel making up an image, etc. are similar to those of the first embodiment.

A maximum/minimum value detecting unit 2803 detects, from the image information made up of a plurality of pixels and obtained in the image information creating unit 2802, maximum and minimum values of brightness by referring to brightness values of the pixels. A brightness difference calculating unit 2804 calculates a brightness difference given as a difference between the maximum and minimum brightness values obtained in the maximum/minimum value detecting unit 2803.

A recording medium type discrimination unit 2805 discriminates the type of the recording medium. The type of the recording medium is discriminated from both the intensity of the specular reflection light obtained in the specular-reflection-light intensity detecting unit 2801 and the brightness difference obtained in the brightness difference calculating unit 2804. The discrimination of the type of the recording medium is performed using parameters 2806 for discrimination, which are derived from a discrimination map prepared in advance and showing the relationships of various types of recording media versus the intensity of the specular reflection light and the brightness difference. Numeral 2806 denotes parameters for discrimination, which are used in discriminating the type of the recording medium in the recording medium type discrimination unit 2805, i.e., thresholds calculated based on distributions measured for the various types of recording media are used as the parameters for discrimination.

Thus, the process flow comprises the steps of detecting the intensity of the specular reflection light from the recording medium, calculating the brightness difference from the image information of the arbitrary small area of the recording medium surface, and then discriminating the type of the recording medium based on those results.

Figure 29:
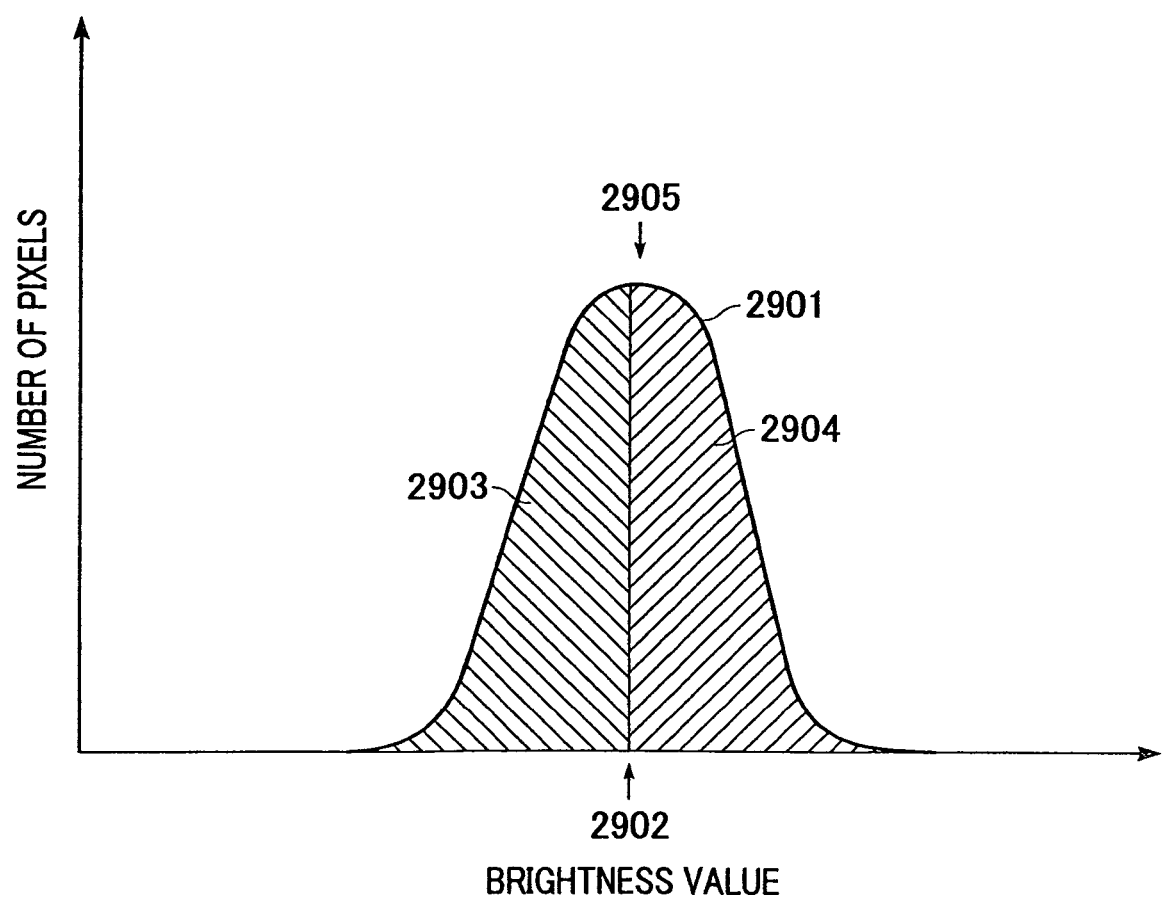
FIG. 29 is a histogram showing the relationship between the number of pixels and a brightness value for an image in the sixth embodiment.

FIG. 29 is a histogram showing the relationship between the number of pixels and a brightness value for an image. The horizontal axis represents the brightness value, and the vertical axis represents the number of pixels having respective brightness values.

Numeral 2901 denotes a histogram of the pixels constituting the image information in terms of brightness. The histogram ideally exhibits a normal distribution, as shown, when measuring an image made up of a number of pixels not smaller than a certain value. Numeral 2902 denotes an arithmetic mean value of brightness of the pixels making up the image. The arithmetic mean value is a value at which the total number of pixels constituting the histogram, i.e., an area of a hatched region in FIG. 29, is divided in half. Herein, such an arithmetic mean value is simply referred to as a "mean value". This average value represents a mean of the brightness of all the pixels, namely, the whiteness of the recording medium. Numerals 2903 and 2904 denote respective regions defined by dividing the area of the hatched region into two equal parts at the mean value. Numeral 2905 denotes a brightness value at a peak of the histogram. In an ideal condition, the arithmetic mean value between the maximum and minimum brightness values used in the first to third embodiments, the mean value in this sixth embodiment, and the brightness value at the peak coincide with each other. In this sixth embodiment, the value denoted by 2902 is referred to as a "mean value" and the value denoted by 2905 is referred to as a "brightness value at the peak (or peak brightness value)".

In this embodiment of the present invention, two kinds of features of the recording medium surface are obtained as parameters, and the type of the recording medium is discriminated based on these parameters. By measuring the intensity of the specular reflection light and the brightness difference resulting from a statistical process as described above, the features regarding the magnitude of unevenness of the recording medium surface are obtained. Herein, the magnitude of unevenness of the recording medium surface obtained from the intensity of the specular reflection light is referred to as a "smoothness or gloss feature", and the magnitude of unevenness of the recording medium surface obtained from the brightness difference is referred to as a "surface roughness feature". A manner of discriminating the type of the recording medium based on those two features will be described below.

Figure 30:
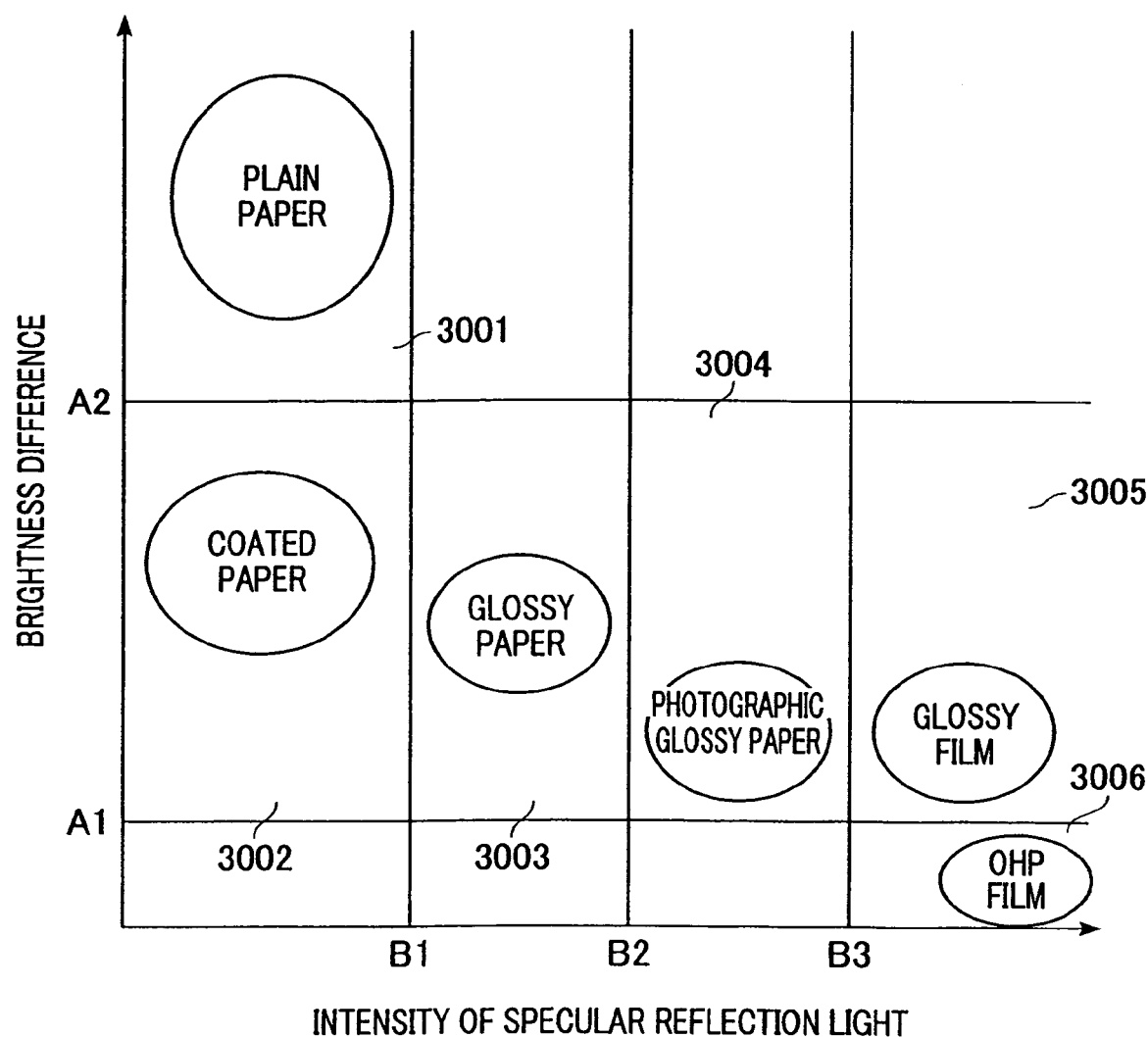
FIG. 30 is a discrimination map showing the relationships of various types of recording media versus a brightness difference and the intensity of a specular reflection light in the sixth embodiment.

FIG. 30 is a discrimination map showing the relationships of various types of recording media versus the brightness difference and the intensity of the specular reflection light. Circular regions in FIG. 30 each represent a set of points corresponding to the measured results, and discrimination areas are defined by dividing a map plane as shown based on the circular regions.

Numeral 3001 represents an area in which the recording medium under measurement is discriminated to be plain paper. Numeral 3002 represents an area in which it is discriminated to be ink-jet coated paper. Numeral 3003 represents an area in which it is discriminated to be glossy paper. Numeral 3004 represents an area in which it is discriminated to be photographic glossy paper. Numeral 3005 represents an area in which it is discriminated to be a glossy film. Numeral 3006 represents an area in which it is discriminated to be an OHP film.

A description is now briefly made of the relationships between features of the six types of recording media to be detected using the parameters of this embodiment, i.e., the intensity of the specular reflection light and the brightness difference.

In plain paper, pulp fibers forming the paper appear on a paper surface. Hence, there is a tendency that the plain paper has a larger magnitude of unevenness than the other types of recording media, and this unevenness appears as dark and light levels of brightness in the created image information. Correspondingly, the plain paper shows a lower gloss level. Also, a large difference between dark and light is related to a large brightness difference.

Ink-jet coated paper is a recording medium formed by coating a pigment, e.g., silica, on a surface of plain paper. Therefore, the ink-jet coated paper has a smaller magnitude of unevenness than plain paper, thus resulting in a smaller surface roughness. Accordingly, the brightness difference of the ink-jet coated paper is smaller than that of the plain paper. A gloss level of the ink-jet coated paper is comparable to or lower than that of the plain paper due to the effect of the pigment, e.g., silica, present on the recording medium surface.

Glossy paper is a recording medium formed by coating several layers of an ink accepting substance on a surface of paper serving as a base. The glossy paper has a smaller magnitude of unevenness than the plain paper and the ink-jet coated paper, and thus it has a higher smoothness and a higher gloss level. As a result, the glossy paper shows a smaller brightness difference.

Photographic glossy paper is a recording medium formed by processing the paper in a manner similar to the above-mentioned glossy paper process. In addition, various improvements are performed on a paper surface to realize an image quality and weatherability comparable to those of a photograph printed on photographic paper. The photographic glossy paper has a smaller magnitude of unevenness than the glossy paper, and thus it has a higher smoothness and a higher gloss level. As a result, the brightness difference of the photographic glossy paper is slightly smaller than that of the glossy paper.

A glossy film is a recording medium formed by coating an ink accepting layer on a surface of a film that is made of, e.g., white PET and serves as a base. The glossy film has a higher smoothness than the glossy paper, and its smoothness is comparable to that of the photographic glossy paper. As a result, the brightness difference of the glossy film is slightly smaller than that of the glossy paper. Also, since the gloss film uses a film as the base, the gloss level of the glossy film tends to be slightly higher than that of the photographic glossy paper.

An OHP film is a recording medium formed by coating an ink accepting layer on a surface of a transparent film serving as a base. Because most of a light illuminated from a light source passes through the recording medium without being reflected by the recording medium surface, the OHP film has a very small brightness value and hence the brightness difference is hardly noticeable. Further, the gloss level of the OHP film tends to be a much higher value than those of the other types of recording media.

The above-described relationships of the various types of recording media versus the brightness difference and the intensity of the specular reflection light are summarized in Table 8 given below.

TABLE 8

| | Plain paper (a) | Coated paper (b) | Glossy paper (c) | Photographic glossy paper (d) | Glossy film (e) | OHP film (f) |
|---|---|---|---|---|---|---|
| Specular reflection light intensity | low | low | Medium | high | higher than (d) | higher than (d) |
| Brightness difference | large | medium | medium | small | small | very small |

Figure 31:
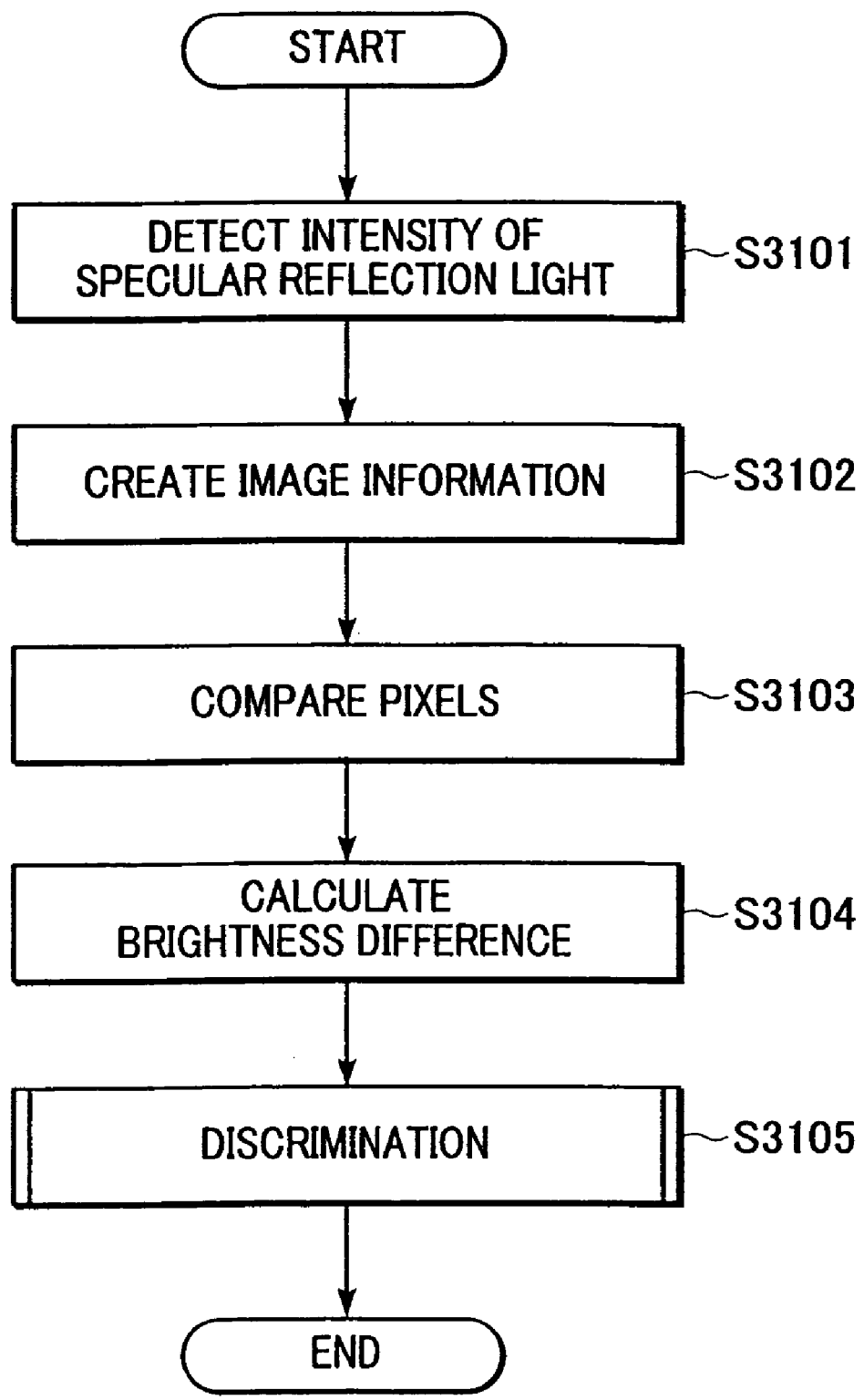
FIG. 31 is a flowchart showing a flow of a recording medium type discrimination process in the sixth embodiment.

FIG. 31 is a flowchart showing a flow of a recording medium type discriminating process in this sixth embodiment.

In step 3101 (S3101), the intensity of the specular reflection light is detected. In step S3102, image information is created. In step S3103, brightness values of pixels are compared with each other based on the image information obtained in step S3102. More specifically, maximum and minimum values of brightness are detected. In step S3104, a brightness difference is calculated as a difference between the maximum and minimum brightness values obtained in step S3103. In step S3105, the type of the recording medium is discriminated based on the intensity of the specular reflection light obtained in step S3101 and the brightness difference obtained as a feature variable in step S3104.

In the flowchart of the recording medium type discriminating process shown in FIG. 31, the intensity of the specular reflection light is detected in step S3101, i.e., at the beginning of the process flow. However, it is only required that the intensity of the specular reflection light is detected before the type of the recording medium is discriminated in step S3105.

Figure 32:
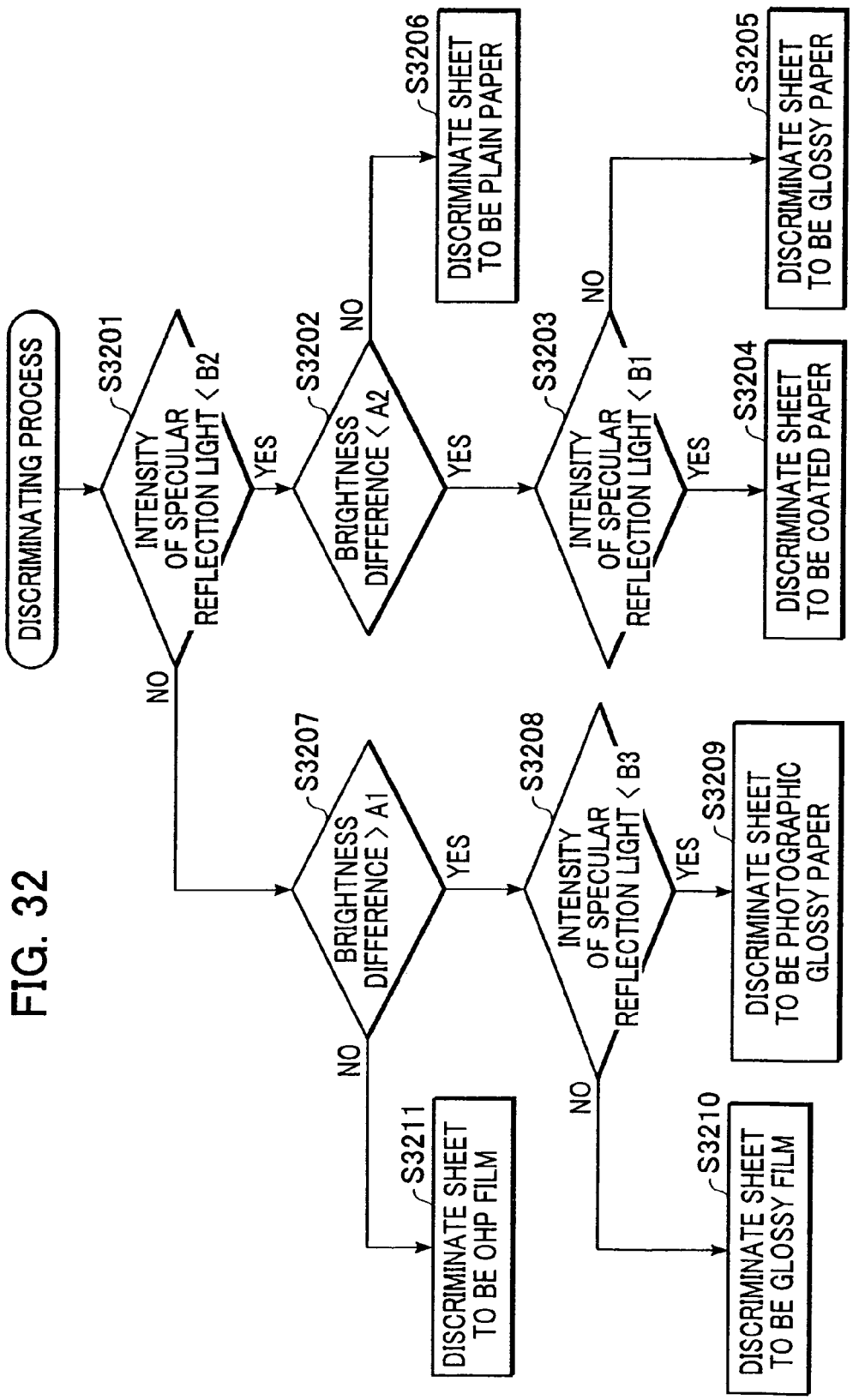
FIG. 32 is a flowchart showing a process flow for discrimination of the type of the recording medium in the sixth embodiment.

FIG. 32 is a flowchart showing a process flow for discrimination of the type of the recording medium in step S3105 shown in FIG. 31.

Based on the discrimination map shown in FIG. 30, the type of the recording medium is discriminated using the two obtained parameters as follows. For the following discussion, assume that the values A1, A2, B1, B2 and B3 satisfy the relationships given below. B1, B2 and B3 are values representing the intensity of the specular reflection light and satisfy a relationship of B1<B2<B3. Also, A1 and A2 are values representing the brightness difference and satisfy a relationship of A1<A2.

In step 3201 (S3201), it is determined whether the intensity of the specular reflection light is smaller than B2. If the intensity of the specular reflection light is smaller than B2, the process flow advances to step S3202, and if not, the process flow advances to step S3207.

In step S3202, it is determined whether the brightness difference is smaller than A2. If the brightness difference is smaller than A2, the process flow advances to step S3203, and if not, the process flow advances to step S3206.

In step S3203, it is determined whether the intensity of the specular reflection light is smaller than B1. If the intensity of the specular reflection light is smaller than B1, the process flow advances to step S3204, and if not, the process flow advances to step S3205.

In step S3204, the type of the recording medium is discriminated to be ink-jet coated paper. In step S3205, the type of the recording medium is discriminated to be glossy paper. In step S3206, the type of the recording medium is discriminated to be plain paper. Alternatively, if attention is paid only to the brightness difference, discriminating whether the type of the recording medium is plain paper can be done at the beginning of the process by determining whether the brightness difference is larger than A2.

In step S3207, it is determined whether the brightness difference is larger than A1. If the brightness difference is larger than A1, the process flow advances to step S3208, and if not, the process flow advances to step S3211.

In step S3208, it is determined whether the intensity of the specular reflection light is smaller than B3. If the intensity of the specular reflection light is smaller than B3, the process flow advances to step S3209, and if not, the process flow advances to step S3210.

In step S3209, the type of the recording medium is discriminated to be photographic glossy paper. In step S3210, the type of the recording medium is discriminated to be a glossy film. In step S3211, the type of the recording medium is discriminated to be an OHP film.

In the flowchart shown in FIG. 32, there are two processing steps to be executed until the type of the recording medium is discriminated to be plain paper. In a recording apparatus in which plain paper is used at high frequency, however, the process flow may be modified so as to promptly make the discrimination as to whether the type of the recording medium is plain paper. In such a situation, whether the type of the recording medium is plain paper can be discriminated by paying attention only to the brightness difference and discriminating whether the brightness difference is larger than A2 before discriminating in step S3201 whether the intensity of the specular reflection light is smaller than B2. In that case, the type of the recording medium can also be discriminated based on the discrimination map shown in FIG. 30 in a similar manner.

For the areas that are not allocated in FIG. 30 as areas used for discriminating the recording medium as a particular type of recording medium, e.g., for the areas in which the intensity of the specular reflection light is smaller than B3 and the brightness difference is not larger than A1, the flowchart of FIG. 32 is designed so as to discriminate the type of the recording medium to be ink-jet coated paper, glossy paper or an OHP film. However, the flowchart may be modified such that, for those areas, the absence of any corresponding type of recording medium is discriminated and the process for discriminating the type of the recording medium is executed again. As an alternative, error processing to return an error signal indicating the absence of any corresponding type of recording medium may be executed, and an error screen for notifying the user of the absence of any corresponding type of recording medium may be displayed.

With this sixth embodiment, as with the first, second, third, fourth and fifth embodiments, a parameter indicated by the intensity of the specular reflection light from the recording medium and a parameter representing surface conditions of the recording medium and derived from an image of a predetermined area of the recording medium surface are obtained, and the type of the recording medium is discriminated based on these obtained parameters. By using the brightness difference when discriminating the type of the recording medium, the accuracy in discriminating, particularly, plain paper and ink-jet coated paper from each other can be improved.

While this embodiment employs the discrimination parameters 2806 in discriminating the type of the recording medium, similar advantages can also be obtained by employing a discrimination table in which the types of recording media are related to each other by the brightness difference and the intensity of the specular reflection light as explained in the second embodiment.

(Seventh Embodiment)

A seventh embodiment implementing the present invention will be described below in detail with reference to the drawings.

Figure 33:
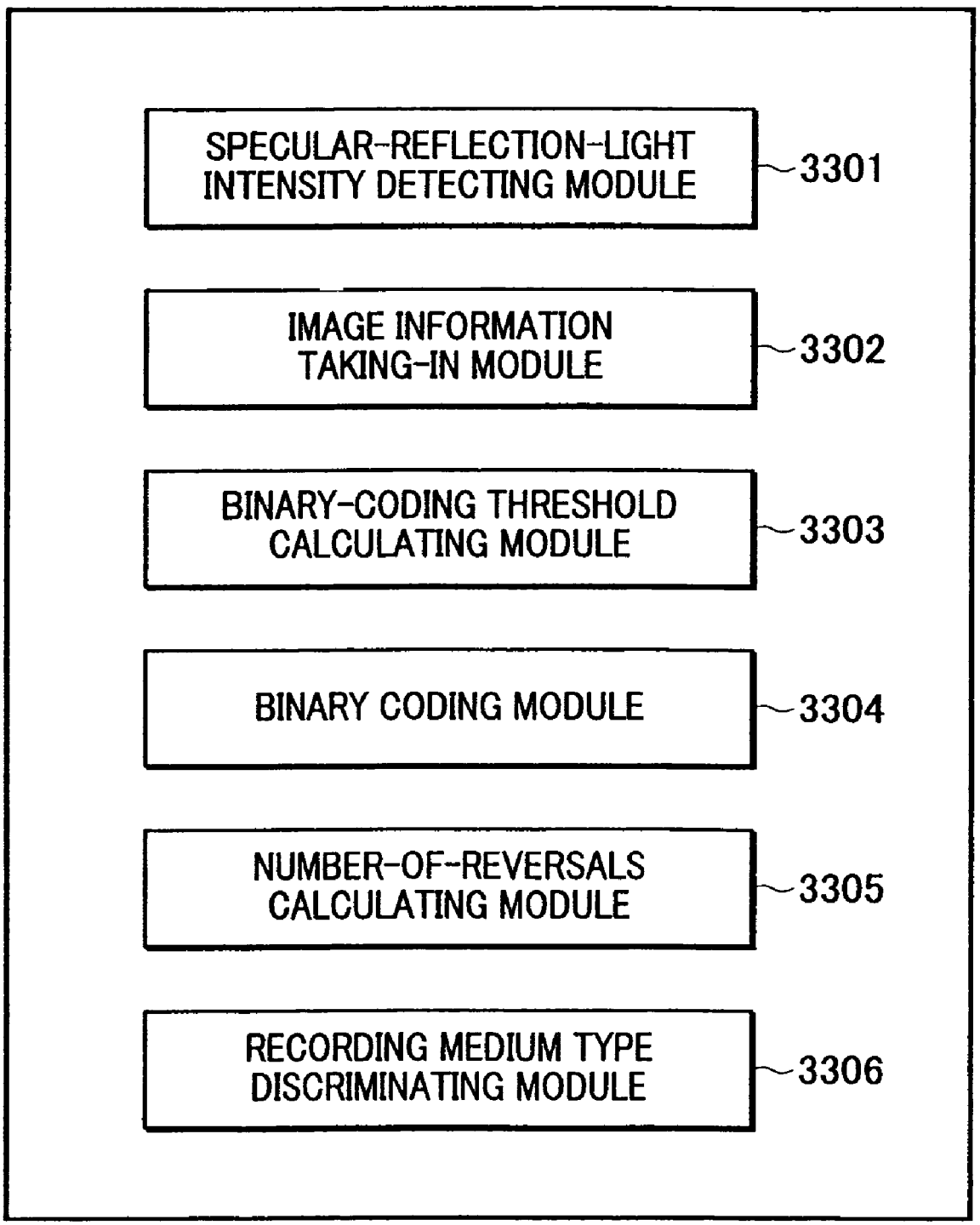
FIG. 33 shows a memory map of a storage medium for use in a seventh embodiment.

FIG. 33 shows a memory map of a storage product for use in the seventh embodiment.

With this embodiment, the type of the recording medium can be discriminated by connecting a storage medium, which stores program codes of software for realizing the functions of any of the above-described embodiments to an apparatus or a system, and causing a computer (CPU or MPU) in the apparatus or the system to read and execute the program codes stored in the storage medium. In that case, the program codes read out of the storage medium serve by themselves the functions of any of the above-described embodiments, and hence the storage medium storing the program codes and the program codes themselves constitute the present invention.

Storage media for storing the program codes may be, e.g., magnetic disks such as Floppy (trade name) disks, hard disks, optical disks such as CD-ROM, CD-R, CD-RW, DVD-RAM, DVD-R, DVD+R and DVD+RW, magneto-optical disks such as MO, magnetic tapes, and nonvolatile memory cards such as a flash memory, and ROMs.

Also, the functions of any of the above-described embodiments are realized not only by a computer executing program codes read out of the storage medium, but also by an Operating System (OS) or the like which is running on the computer and executes a part or the entirety of the actual processing in accordance with commands from the program codes, thereby realizing the functions of any of the above-described embodiments. Those cases are also of course included in embodiments of the present invention.

Further, the present invention involves a case in which program codes read out of the storage medium are written in a memory provided in a function add-on board inserted in the computer or a function add-on unit connected to the computer, and a CPU or the like incorporated in the function add-on board or unit executes a part or the entirety of the actual processing in accordance with commands from the program codes, thereby realizing the functions of any of the above-described embodiments.

When the present invention is applied to such a storage medium, the program codes corresponding to any of the flowcharts of FIGS. 8, 15, 26 and 31 showing the recording medium type discriminating process are stored in the storage medium. To briefly explain the embodiment in connection with the flowchart of FIG. 8 according to the first embodiment, modules shown in the memory of FIG. 33 are stored in the storage medium. More specifically, the storage medium is required to store therein at least programs codes defining a specular-reflection-light intensity detecting module 3301, an image information taking-in module 3302, a binary-coding threshold calculating module 3303, a binary coding module 3304, a number-of-reversals calculating module 3305, and a recording medium type discriminating module 3306. The binary-coding threshold calculating module 3303 may be a module for calculating at least one of the mean value of brightness of all pixels, the arithmetic mean value between the maximum and minimum brightness values, and the brightness value at the histogram peak. Also, corresponding to the other embodiments described above, the number-of-reversals calculating module 3305 may be replaced with a run-length code amount calculating module or a number-of-isolated pixels calculating module. Further, the binary-coding threshold calculating module 3303, the binary coding module 3304, and the number-of-reversals calculating module 3305 may be replaced with a number-of-reversals of positive and negative signs calculating module, a number-of-peak pixels calculating module, or a brightness difference calculating module.

As described above, even when the intended functions are realized by a storage medium storing computer-readable program codes or software in the form of program codes themselves, it is possible to obtain a feature indicated by the intensity of the specular reflection light from the recording medium and a feature representing surface conditions of the recording medium and derived from an image of a predetermined area of the recording medium surface, and then discriminate the type of the recording medium with high accuracy based on the obtained features.

(Other Embodiments)

Other embodiments realizing the present invention will be described below.

In the present invention, as described above, the image information of the recording medium surface is created and an image used for creating the image information may be one- or two-dimensional. However, some of the above embodiments have been described on an assumption that the parameters used for discriminating the type of the recording medium are extracted from a one-dimensional image. Hence, a processing method in the case of producing a two-dimensional image by an area sensor or the like will be briefly described below.

Figure 34:
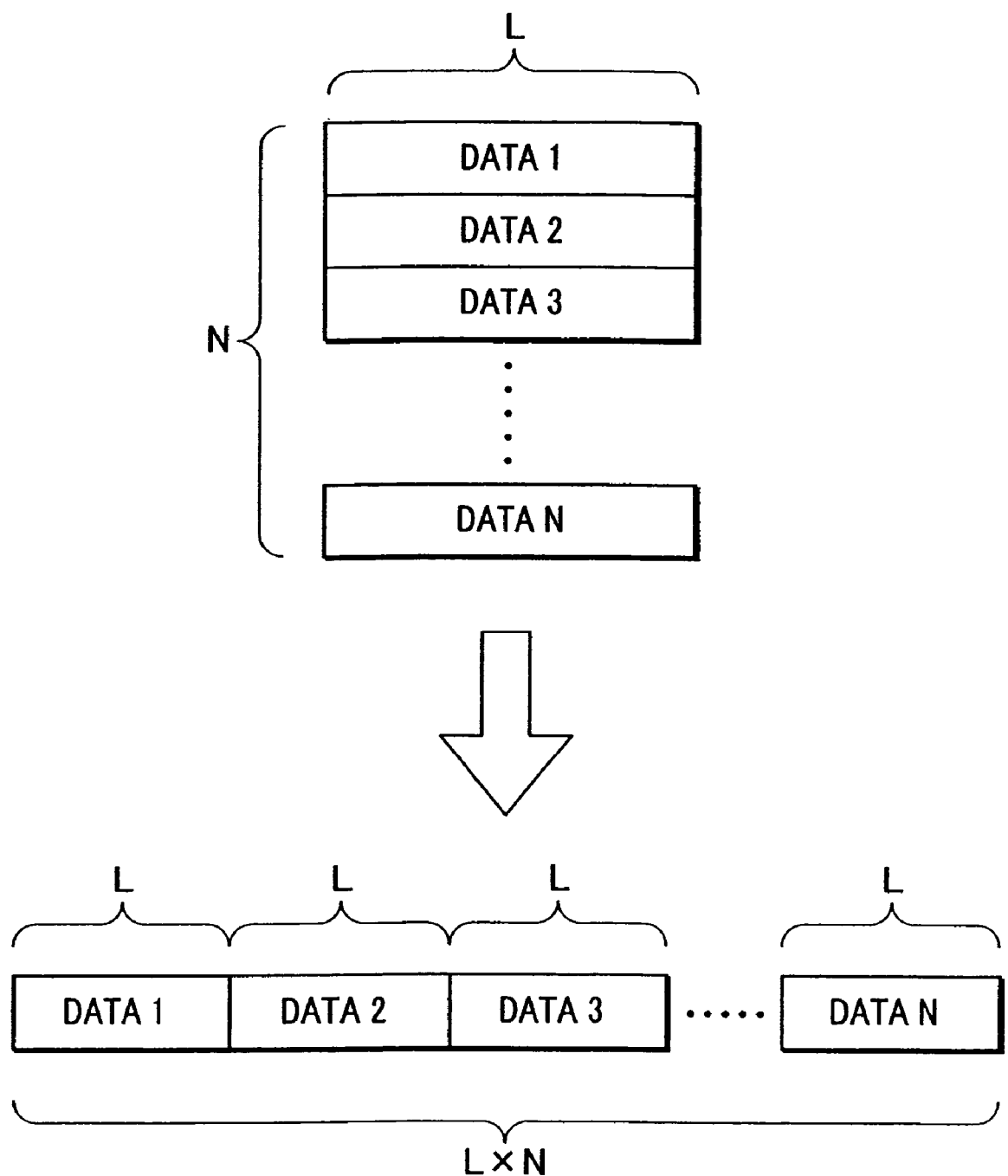
FIG. 34 is a representation showing conversion from two-dimensional image information into one-dimensional image information in still another embodiment.
Figure 35:
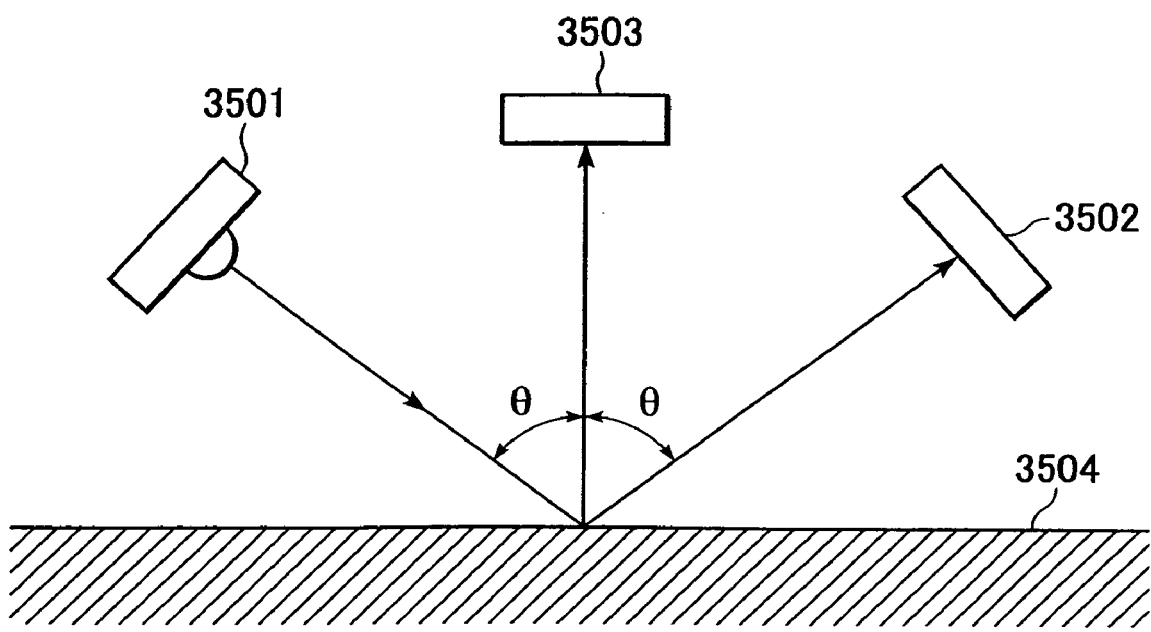
FIG. 35 is a schematic view showing one layout of a sensor in the related art.
Figure 36:
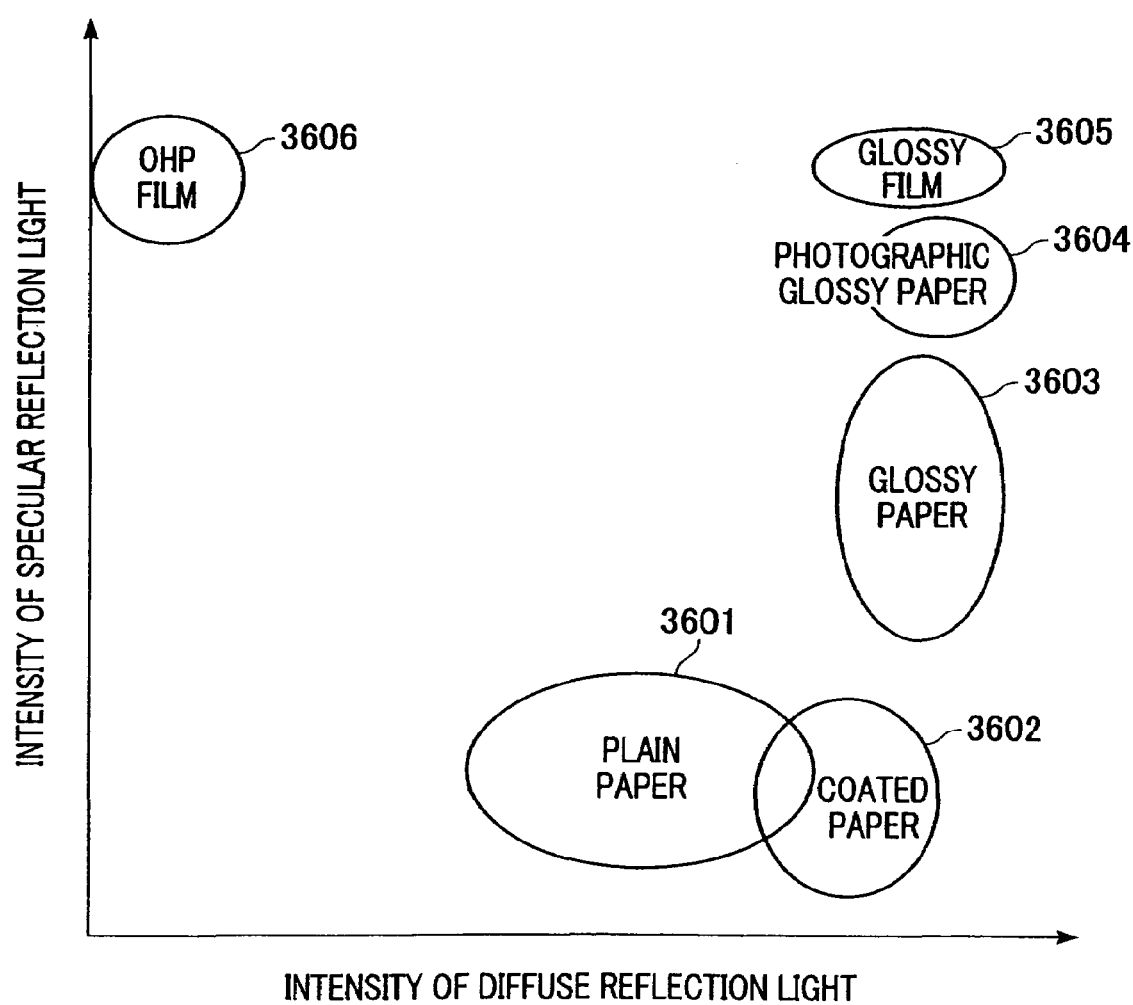
FIG. 36 is a discrimination map showing the relationships of various types of recording media versus the intensity of the specular reflection light and the intensity of a diffuse reflection light in the related art.
Figure 37:
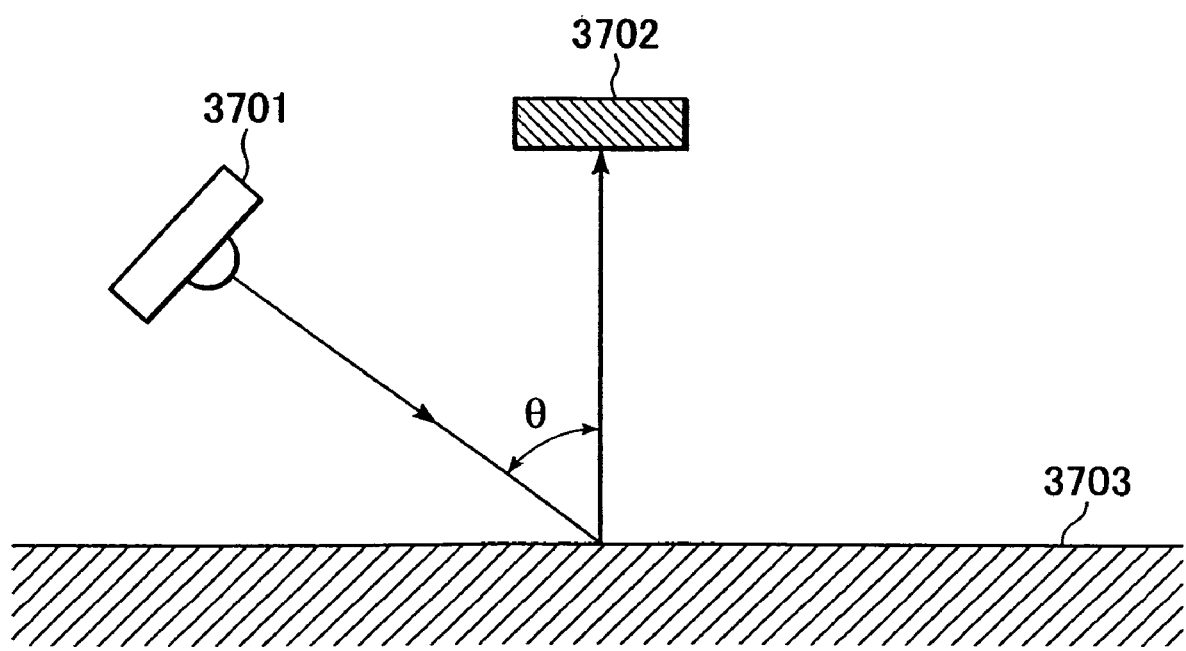
FIG. 37 is a schematic view showing another layout of a sensor in the related art.
Figure 38:
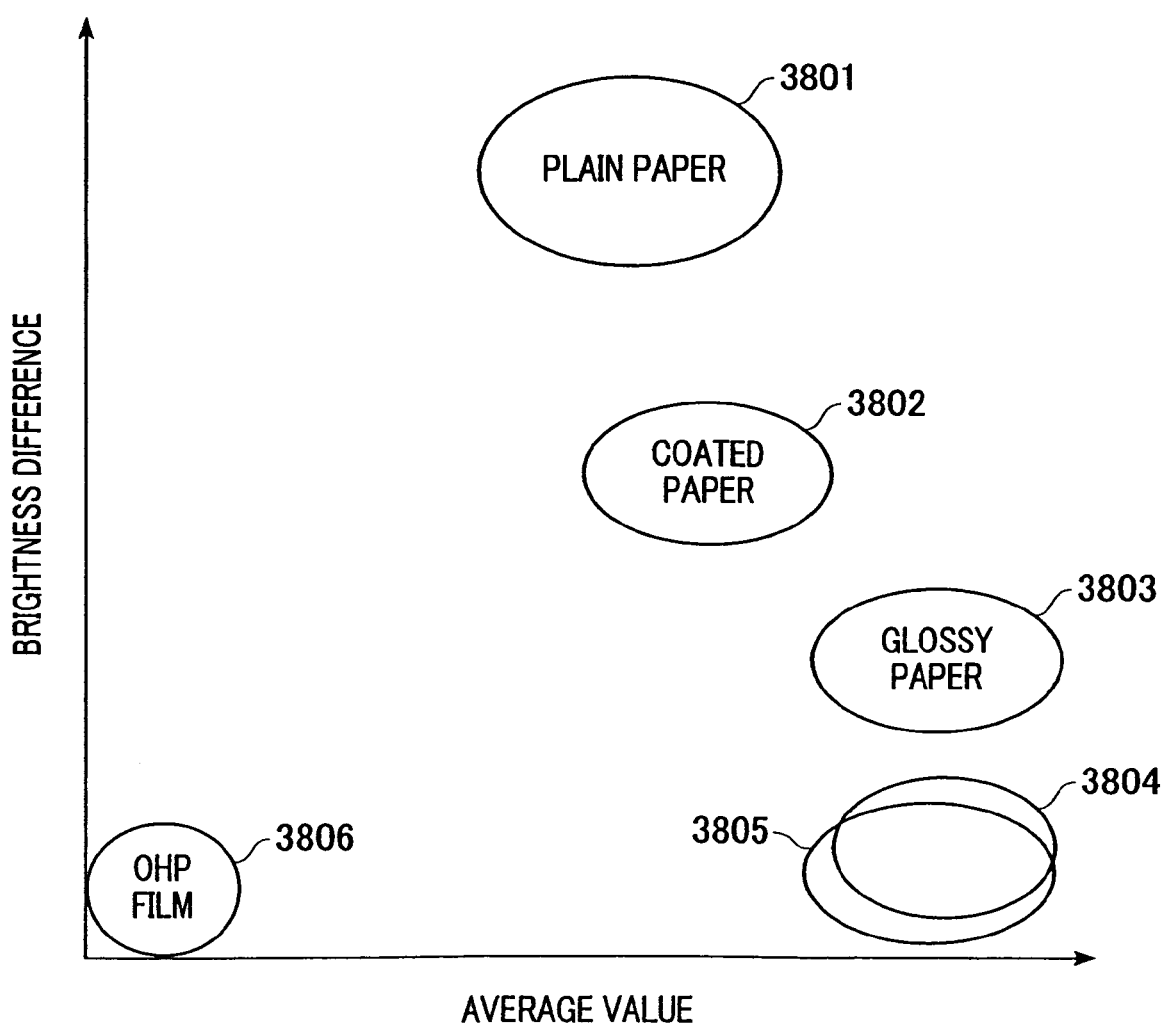
FIG. 38 is a discrimination map showing the relationships of various types of recording media versus a brightness difference and an average value of brightness in the related art.

FIG. 34 is a representation showing conversion from two-dimensional image information into one-dimensional image information.

Two-dimensional image information can be thought as being made up of, as shown in FIG. 34, N sets of one-dimensional image information each arranged in the form of a line having a length L. In this case, a total number of pixels is L×N. Here, data (image information) in the respective lines are referred to as "Data 1", "Data 2", and so on. The two-dimensional image information is converted into one-dimensional image information by joining the line data Data 1, Data 2, and so on, which constitute the two-dimensional image information, with each other in series. With the conversion, line data having a length of L×N is produced as one-dimensional image information.

While FIG. 34 schematically shows the conversion from two-dimensional image information into one-dimensional image information as a linear array for easier understanding, it is possible in practical processing that each line of data is subjected to processing, and processing results are accumulated and used as the parameter for discriminating the type of the recording medium. For example, Data 1 of the first line is subjected to binary coding, and the number of reversals is calculated from a resulting binary image. In a similar manner, Data 2 is subjected to binary coding, and the number of reversals is calculated. Then, similar processing is repeated on the data of the remaining lines. Finally, the numbers of reversals resulting from processing the data of the respective lines are added for the total number of lines. A total number of reversals thus obtained can be used as the parameter for discriminating the type of the recording medium.

Typically, the arithmetic mean value calculated from maximum and minimum values of brightness of all (L×N) pixels, the mean value of brightness of all the pixels, or the brightness value at the histogram peak is used as the threshold for the binary coding. For the purpose of reducing a processing load, however, the process flow may be modified so as to calculate a threshold and execute the binary coding in units of a line. To increase the accuracy in discriminating the type of the recording medium, it is desired that the brightness difference be calculated from all the pixels.

In each of the embodiments described above, two parameters, i.e., the intensity the specular reflection light and one of the number of reversals, the run-length code amount, etc., obtained from the image information of the recording medium surface are employed and the type of the recording medium is discriminated by utilizing the correlation between those two parameters. However, three or more of the parameters described in the above embodiments, for example, the intensity of the specular reflection light, the brightness difference, the number of reversals of pixel values after the binary coding, and the number of reversals of positive and negative signs, may be used in a combined way. By employing a combination of three or more parameters, it is possible to realize the discrimination with greater precision and higher accuracy.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A recording medium type discriminating method for discriminating the type of a recording medium, comprising the steps of:

creating, as image information indicating surface conditions of the recording medium, image information containing information for each of a plurality of pixels corresponding to a predetermined area of a recording medium surface;

detecting a gloss level by measuring an amount of a specular reflection light of lights reflected from the recording medium surface when the recording medium surface is illuminated;

obtaining, from the image information, a parameter regarding the surface conditions of the recording medium; and discriminating the type of the recording medium based on the gloss level and the parameter.

2. A recording medium type discriminating method according to claim 1, wherein the image information contains brightness information for each of the plurality of pixels, and
the parameter is obtained from the brightness information and represents a magnitude of unevenness of the recording medium surface.

3. A recording medium type discriminating method according to claim 2, wherein the parameter is obtained by a statistical process based on the brightness information.

4. A recording medium type discriminating method according to claim 1, wherein the image information contains brightness information for each of the plurality of pixels, and
the parameter is obtained from changes of the brightness information in accordance with an array of a successive plurality of pixels that represents a period of unevenness of the recording medium surface.

* * * * *

UNITED STATES PATENT AND TRADEMARK OFFICE
CERTIFICATE OF CORRECTION

PATENT NO. : 7,125,114 B2
APPLICATION NO. : 11/111955
DATED : October 24, 2006
INVENTOR(S) : Tsujimoto It is certified that error appears in the above-identified patent and that said Letters Patent is hereby corrected as shown below:

COLUMN 3:
Line 59, "more tightly" should read --sharper--.

COLUMN 5:
Line 21, "etc." should read --etc.,--.

COLUMN 9:
Line 19, "embodi-" should be deleted.
Line 20, "ment of the present invention." should be deleted.

COLUMN 10:
Line 5, "tion light" should read --tion-light--.
Line 41, "recording-medium" should read --recording medium--.

COLUMN 11:
Line 21, "outputted" should read --output--.
Line 23, "etc." should read --etc.,--.

COLUMN 14:
Line 5, "ZYGO)" should read --ZYGO).--.

COLUMN 19:
Line 46, "etc." should read --etc.,--.

COLUMN 21:
Line 65, "etc." should read --etc.,--.

COLUMN 25:
Line 50, "used the" should read --used in the--.

COLUMN 26:
Line 37, "etc." should read --etc.,--.

COLUMN 29:
Line 30, "signs;of" should read --signs of--.

COLUMN 33:
Line 20, "etc." should read --etc.,--.

UNITED STATES PATENT AND TRADEMARK OFFICE
CERTIFICATE OF CORRECTION

PATENT NO. : 7,125,114 B2
APPLICATION NO. : 11/111955
DATED : October 24, 2006
INVENTOR(S) : Tsujimoto It is certified that error appears in the above-identified patent and that said Letters Patent is hereby corrected as shown below:

COLUMN 37:
Line 28, "sixth" should read --The sixth--.
Line 54, "etc." should read --etc.,--.

COLUMN 43:
Line 4, "programs" should read --program--.

COLUMN 44:
Line 26, "intensity the" should read --intensity of the--.

Signed and Sealed this

Fifteenth Day of July, 2008

JON W. DUDAS
*Director of the United States Patent and Trademark Office*